(12) United States Patent
Kohr et al.

(10) Patent No.: US 10,227,853 B2
(45) Date of Patent: *Mar. 12, 2019

(54) MICROBIAL ENHANCED OIL RECOVERY METHOD

(71) Applicant: GEO FOSSIL FUELS, LLC, Golden, CO (US)

(72) Inventors: William J. Kohr, Gig Harbor, WA (US); David J. Galgoczy, San Francisco, CA (US); Zhaoduo Zhang, Pleasanton, CA (US)

(73) Assignee: Geo Fossil Fuels, LLC, Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/833,929

(22) Filed: Dec. 6, 2017

(65) Prior Publication Data

US 2018/0112504 A1 Apr. 26, 2018

Related U.S. Application Data

(63) Continuation of application No. 14/917,871, filed as application No. PCT/US2014/055256 on Sep. 11, 2014, now Pat. No. 9,869,166.

(60) Provisional application No. 61/877,068, filed on Sep. 12, 2013.

(51) Int. Cl.
*E21B 43/20* (2006.01)
*C09K 8/582* (2006.01)
*C12N 1/26* (2006.01)
*C12P 19/06* (2006.01)
*C12P 7/64* (2006.01)

(52) U.S. Cl.
CPC .............. *E21B 43/20* (2013.01); *C09K 8/582* (2013.01); *C12N 1/26* (2013.01); *C12P 19/06* (2013.01); *C12P 7/6463* (2013.01)

(58) Field of Classification Search
None
See application file for complete search history.

(56) References Cited

U.S. PATENT DOCUMENTS

| 2,660,550 | A | 11/1953 | Updegraff et al. |
| 2,907,389 | A | 10/1959 | Hitzman |
| 2,975,835 | A | 3/1961 | Bond |
| 3,032,472 | A | 5/1962 | Hitzman |
| 3,332,487 | A | 7/1967 | Jones |

(Continued)

FOREIGN PATENT DOCUMENTS

| WO | WO-199213172 A1 | 8/1992 |
| WO | WO-2012116230 A1 | 8/2012 |

OTHER PUBLICATIONS

Ghafoor et al., "Role of exopolysaccharides in Pseudomonas aeruginosa biofilm formation and architecture," (2011) Appl. Envir. Microbio. 77(15):5238-46.

(Continued)

*Primary Examiner* — Anuradha Ahuja
(74) *Attorney, Agent, or Firm* — Benjamin C. Pelletier; Alissa H. Faris; Venable LLP

(57) ABSTRACT

The present invention provides methods for increasing the viscosity of the drive fluid for displacing oil from a subterranean formation by the use of microorganisms selected or modified for the ability to produce cell free polymers without the formation of any significant bioplugging biofilm or capsule.

13 Claims, 3 Drawing Sheets

Specification includes a Sequence Listing.

Alkaliphile ML2-9 recovered from sand packed column with (left) or without oil (right)

(56) References Cited

U.S. PATENT DOCUMENTS

| | | | | |
|---|---|---|---|---|
| 4,006,058 | A * | 2/1977 | Savins | C12N 1/32 435/101 |
| 4,475,950 | A | 10/1984 | Finlayson | |
| 4,558,739 | A | 12/1985 | McInerney et al. | |
| 4,799,545 | A | 1/1989 | Silver et al. | |
| 4,800,959 | A | 1/1989 | Costerton et al. | |
| 4,905,761 | A * | 3/1990 | Bryant | C09K 8/58 166/246 |
| 4,971,151 | A | 11/1990 | Sheehy | |
| 5,163,510 | A | 11/1992 | Sunde | |
| 5,297,625 | A * | 3/1994 | Premuzic | C09K 8/58 166/246 |
| 6,543,535 | B2 * | 4/2003 | Converse | C09K 8/58 166/246 |
| 6,546,962 | B1 | 4/2003 | Sunde | |
| 7,472,747 | B1 | 1/2009 | Brigmon et al. | |
| 8,316,933 | B2 * | 11/2012 | Kohr | C09K 8/582 166/246 |
| 8,357,526 | B2 | 1/2013 | Keeler et al. | |
| 9,869,166 | B2 | 1/2018 | Kohr et al. | |
| 2001/0045279 | A1 * | 11/2001 | Converse | C09K 8/58 166/246 |
| 2009/0029879 | A1 * | 1/2009 | Soni | C09K 8/582 507/201 |
| 2011/0067856 | A1 * | 3/2011 | Kohr | C09K 8/582 166/246 |
| 2011/0268846 | A1 | 11/2011 | Nair et al. | |
| 2012/0261117 | A1 * | 10/2012 | Pavia | C09K 8/582 166/246 |
| 2012/0273189 | A1 | 11/2012 | Alsop et al. | |
| 2013/0062053 | A1 | 3/2013 | Kohr et al. | |
| 2014/0315765 | A1 * | 10/2014 | McDaniel | C09K 8/582 507/201 |
| 2017/0064966 | A1 * | 3/2017 | Opatowsky | A01N 63/02 |

OTHER PUBLICATIONS

Robleto et al., "Genetic analysis of the AdnA regulon in Pseudomonas fluorescens: nonessential role of flagella in adhesion to sand and biofilm formation," (2003) J. Bacteriology 185(2):453-60.
O'Toole et al., "Initiation of biofilm formation in Pseudomonas fluorescens WCS365 proceeds via multiple, convergent signaling pathways: a genetic analysis," (1998) Mol. Microbiol. 28(3):449-61.
Branda et al., "A major protein component of the Bacillus subtilis biofilm matrix," (2006) Mol. Microbiol. 59(4):1229-38.
Chu et al., "Targets of the master regulator of biofilm formation in Bacillus subtilis," (2006) Mol. Microbiol. 59(4):1216-28.
Colvin et al., "The Pel and Psl polysaccharides provide Pseudomonas aeruginosa structural redundancy within the biofilm matrix," (2012) Environ. Microbiol. 14(8):1913-28.
Darzins et al., "Clustering of mutations affecting alginic acid biosynthesis in mucoid Pseudomonas aeruginosa," (1985) J. Bacteriol., 164:516-24.
Dogsa et al., "Exopolymer diversity and the role of levan in Bacillus subtilis biofilms," (2013) PLoS One 2013 8(4):e62044.
Hay et al., "Impact of alginate overproduction on attachment and biofilm architecture of a supermucoid Pseudomonas aeruginosa strain," (2009) Appl. Environ. Microbiol. 75(18):6022-25.
Katzen et al., "Promoter analysis of the *Xanthomonas campestris* pv. *campestris* gum operon directing biosynthesis of the xanthan polysaccharide," (1996) J. Bacteriol. 178(14):4313-18.
Kim and Kim, "Application of LFH-PCR for the disruption of SpoIIIE and SpoIIIG of *B. subtilis*," (2000) Biotechnol. Bioprocess Eng. 5(5):327-31.
Makarove and Koonin, "Comparative genomics of Archaea: how much have we learned in six years, and what's next?" (2003) Genome Biology, 4(8) article 115 (17 pages).
Mathee et al., "Mucoid conversion of *Pseudomonas aeruginos* by hydrogen peroxide: a mechanism for virulence activation in the cystic fibrosis lung," (1999) Microbiology 145(6):1349-57.
Pollock, et al., "Production of xanthan gum by *Sphingomonas* bacteria carrying genes from *Xanthomonas campestris*," (1997) J. Ind. Microbiol. Biotech. 19:92-7.
Romero et al., "Amyloid fibers provide structural integrity to *Bacillus subtilis* biofilms," (2010) PNAS 107(5):2230-34.
Karatan et al., "Signals, Regulatory Networks, and Materials that Build and Break Bacterial Biofilms," (2009) Microbiol Mol Biol Rev 73(2):310-47.
Ma, "The Roles of Biofilm Matrix Polysaccharide Psl in Mucoid *Pseudomonas Aeruginosa* Biofilms," (2012) FEMS Imuunol Med Microbiol 65:377-380.
Mann et al., "*Pseudomonas* Biofilm Matrix Composition and Niche Biology," (2012) FEMS Microbiol Rev 36:893-916.
Vlamakis et al., "Sticking Together: Building a Biofilm the *Bacillus Subtilis* Way," (2013) Nature Review Microbiology 11:157-68.
Suppiger et al., "The DSF Type Quorum Sensing Signalling Systems RpfF/R Regulates Diverse Phenotypes in the Opportunistic Pathogen Cronobacter," (2016) Nature, Scientific Reports, p. 1-8.

* cited by examiner

Figure 1    Microbial penetration

Alkaliphile ML2-9 recovered from sand packed column with (left) or without oil (right)

Post Column Analysis for Determination of Adhered Cells:

Figure 3  Bio-plugging
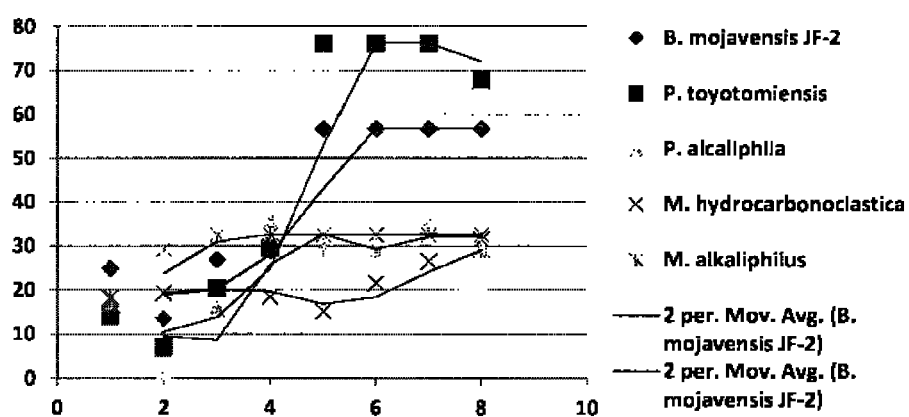
Back pressure in inch profile over 10 days incubation at room temperature

MICROBIAL ENHANCED OIL RECOVERY METHOD

CROSS REFERENCE TO RELATED APPLICATIONS

This application is a continuation of U.S. application Ser. No. 14/917,871, filed Mar. 9, 2016, which is a national stage entry filed under 35 USC § 371 of PCT Application No. PCT/US2014/055256, filed Sep. 11, 2014, which claims benefit of priority under 35 USC § 119(e) of provisional application No. 61/877,068, filed Sep. 12, 2013, the entire disclosures of which are hereby incorporated by reference in their entirety.

SEQUENCE LISTING

The instant application contains a sequence listing which has been submitted electronically in ASCII format and is hereby incorporated by reference in its entirety. Said ASCII copy, created on Sep. 26, 2017, is named GFF-0004C1-US_SL.text and is 49,937 bytes in size.

FIELD OF THE INVENTION

The present invention concerns a microbial enhanced oil recovery method. In particular, this invention relates to the in situ production of bio-polymers and biosurfactants for the enhanced recovery of petroleum. More specifically, microorganisms are selected and/or modified for their ability to produce soluble exopolymers of high molecular weight that increase the viscosity of the waterflood drive fluid without the extensive formation of biofilms that greatly reduce permeability.

BACKGROUND OF THE INVENTION

The demand for crude oil has exceeded the existing production in the United States for more than 30 years. This has led to increasing demand for more imported oil and a dependency on foreign suppliers. The growth of emerging economies is rapidly increasing the demand for oil in the global market. It has been estimated that more than half of all conventional oil (oil that can be produced with current technology) has been produced. Most of the remaining conventional oil is located in the Eastern Hemisphere or in environmentally sensitive areas such as the North Pole. The lack of conventional oil supplies could keep oil prices so high that oil dependent nations such as the United States would be unable to fund the development of alternative energy technologies and be forced into dependency on foreign alternative energy as well. Therefore any new technology that could increase the efficiency of oil recovery would be of great benefit to countries such as the U.S. that have large amounts of unrecoverable oil in place (OIP) in older exiting oil fields.

Most petroleum is found in sandstone, siltstone or carbonate. Porosities vary from 5% to 30%. The porous rock, covered with an impermeable layer, collects oil from organic matter in lower source rock. It is a process that takes millions of years. The maturation process converts it to a complex mixture of hydrocarbons of about 82 to 87% carbon and 12 to 15% hydrogen. The oil moves into the porous rock in low concentrations with water. To become a reservoir the porous rock must have some type of impermeable cap-rock that traps the oil. Most traps are anticlinal upfolds of strata that are oval shape, however, fault-traps and salt-domes are also common. Oil near the surface often encounters descending meteoric water that brings in oxygen and bacteria that degrade the oil to heavy oil or tar. Oil is usually not found below 4,900 meters because the high temperature of deep rock will degrade the petroleum into natural gas. Therefore, most oil is less than 4,900 m deep.

Unlike natural gas, the recovery of petroleum oil is not efficient. The existing conventional oil production technologies are able to recover only about one-half of the oil originally in place in a reservoir of light oil. For heavy oil, the recovery is often less than 10%. Tar sands are so heavy that they will not flow at all and no oil can be recovered by conventional drilling and pumping. A technology that could recover a greater percentage of this residual oil could increase oil production from existing reservoirs and reduce the need of the U.S. to imported oil. The additional oil recovered from existing oil producing reservoirs could reduce the need to explore and develop wilderness areas that are potential new oil fields. This additional recovery of existing oil could bridge the gap needed for the development of alternative renewable energy sources.

The Original Oil In Place (OOIP) is the petroleum present in the oil reservoir when first discovered. The volume of the reservoir is determined by the size and porosity of the carbonate or sand stone. The porosity of the rock is a measure of the amount of small chambers or micro-traps within the rock that can hold water or oil. The oil is generally pushed up to the surface with the existing oil reservoir pressures at first. The pressure in the oil well drops with time and there is a need to create overpressure with other means such as water injection or a gas injection for secondary recovery of the OOIP. The choice of a specific secondary recovery technique depends on the type of the hydrocarbon accumulation and the nature of the reservoir. Water injection or "water sweep" or "waterflooding" is a common secondary recovery technique. In waterflooding, pressurized water is injected into the oil-bearing formation rock. Ideally, the injected water displaces the residual oil and moves it to a producing well. Generally in waterflooding, crude oil free of water is recovered first, and then subsequently a mixture of crude oil and water are recovered from the production wells. At some point, the percentage of water in the oil-water mixture (referred to as the water cut) from this technique becomes so high that it is uneconomical to continue pumping oil from the well. The problem, with using water as a "drive fluid", is that water and oil are immiscible. The lower viscosity water will flow over the oil and by-pass large amounts of oil. Therefore, even after secondary recovery, a significant portion of crude oil remains in the formation, in some cases up to 75% of the OOIP.

Highly fractured reservoirs represent an additional problem for recovering by waterflooding. The influence of faulting and natural fractures within the reservoir formation will cause high flow zones of fluid migration. This will lead to the drive fluid to bypass the most of the less permeable oil saturated formation. These "thief" zones require selective plugging before waterflooding can effectively be used.

The fraction of unrecoverable crude oil is typically highest for heavy oils, tar, and large complex hydrocarbons. In the U.S. this residual OIP in old oil wells could be as much as 300 billion barrels of light oil. World-wide, the estimate of unrecoverable oil is 2 trillion barrels. There are an additional 5 trillion barrels of heavy oil, most of which is unrecoverable. Much of this remaining oil is in micro-traps due to capillary forces or adsorbed onto mineral surfaces (irreducible oil saturation) as well as bypassed oil within the rock formation.

Enhanced Oil Recovery

Oil recovery by injection of fluids not normally found in the reservoir is referred to as Enhanced Oil Recovery (EOR). It is a subset of Improved Oil Recovery (IOR), which can include operational strategies such as infill drilling and horizontal drilling. Although it is sometimes referred to as tertiary recovery, it can be implemented along with secondary processes. Many types of EOR have been proposed and used over the years. Technical complexity and the high cost of chemicals have prevented the widespread use of EOR to where it only represents about 10% of total United States oil production.

There have been two major EOR approaches; thermal and non-thermal.

Thermal Processes

Thermal processes work by heating the reservoir rock and the oil to reduce viscosity of the heavy oil. In general, the lower the viscosity of the oil, the better its recovery will be. The most widely used thermal process is steam injection in which the temperature of the reservoir and the remaining oil is increased by heat energy of steam. Hot water may also be used, but it is not as efficient at transferring heat to the oil and rock in the reservoir. Unfortunately, in both processes, most of the heat energy is lost to the surroundings and does not go to heating the oil. In situ combustion of the oil is much more efficient than steam because it only heats the reservoir and not all the pipes and overburden rock. However, in situ combustion is difficult to control and is seldom used. Typically, it requires the energy equivalent of a half a barrel of oil to recover a barrel of oil with a steam injected thermal process. However, this depends on the oil saturation and the configuration of the reservoir. Because most of the energy carried by the steam is given up to the pipes, wall rock, and reservoir, it is best to use only on reservoirs with a high oil content so as to recover as much oil as possible with the steam used to heat the reservoir rock. Generally, thermal methods are used on heavy oil because it reduces the viscosity of the oil and increases the mobility of the oil and the mobility ratio (mobility of displacing fluid to mobility of displaced fluid or oil). Typically, recoveries are in the range of 50 to 60% for a thermal process, but the net energy gain is much less than that because of the large amount of energy needed to make steam.

Non-Thermal Processes

Several non-thermal processes have been experimented with or used over the years. These rely on a combination of reducing the oil viscosity and decreasing the interfacial tension (IFT) between the oil and displacing fluid. Ideally, the mobility of the displacing fluid should not be higher than the oil. The mobility ratio (mobility of displacing fluid over mobility of displaced fluid) should be low. The mobility of the oil can be increased by viscosity reduction and by IFT reduction. As the IFT is decreased, the oil becomes more miscible with the fluid until it becomes one phase and the IFT is zero. This decreases the mobility ratio and increases the oil recovery. Alternatively, the viscosity of the displacing fluid can be increased by adding polymers to "thicken" the liquid. Non-thermal methods require less energy and are best suited for light oil of 100 cp or less. However, most non-thermal methods require considerable laboratory experimentation and process optimization.

Microbial Enhanced Oil Recovery (MEOR)

One special type of EOR technique uses microorganisms such as bacteria and archaea to dislodge the micro-trapped or adsorbed oil from the rock. The goal of this technique, which is known as microbial enhanced oil recovery (MEOR), is to increase oil recovery of the original subsurface hydrocarbons using bacteria rather than the more costly chemical recovery processes. These biological processes typically use microorganisms to achieve similar results as the chemical methods in that they reduce IFT and reduce the mobility ratio of the water drive fluid to oil. Of all the EOR processes, MEOR is presently considered the lowest cost approach, but is generally the least often used. The main reason this biological process is not more widely used, is that it is not always successful or predicable. Furthermore, bacteria in oil wells, pipes and tanks are known to cause problems. In fact, it is believed that high viscosity heavy oil such as oil sands are the result of bacteria consuming the lighter weight petroleum components and leaving behind the high molecular weight fractions which are less readily consumed by the bacteria. Therefore many petroleum engineers sec bacteria as a problem, not a solution. In fact, if not used correctly, the growth of bacteria could degrade the oil or increase the hydrogen sulfide concentration in the reservoir.

Numerous microorganisms have been proposed for achieving various microbial objectives in subterranean formations. Early MEOR techniques involved injection of an exogenous microbial population into old and low producing oil wells. The inoculating culture was supplied with nutrients and mineral salts as additives to the water pumped into wells for oil recovery. The development of exogenous microorganisms has been limited by the conditions that prevail in the formation. Physical constraints, such as the small and variable formation pore sizes together with the high temperature, salinity and pressure of fluids in the formation and the low concentration of oxygen in the formation waters severely limit the types and number of microorganisms that can be injected and thrive in the formation. Later, it became apparent that indigenous microbes stimulated by the nutrients were playing the major role in oil recovery. Accordingly, many attempts at biological oil recovery do not inject bacteria at all, but rely on indigenous microorganisms exiting in the extreme environment of the oil reservoir.

Methods of enhanced microbial oil recovery are disclosed, for example, in U.S. Pat. No. 8,316,933 and in U.S. Patent Publication Nos. 20130062053 and 20110268846.

Petroleum reservoirs are generally not uniform in permeability or oil saturation. A common type of oil reservoir will be comprised of high and low permeable layers that vary in oil saturation, type of oil and connectivity to one another. If brine is pumped into injection wells to drive the residual oil toward a production well the fluid flow will be difficult to control. Fluid flows along the path of least resistance, which tends to first sweep the oil from the most permeable zone or the zone with the lowest viscosity resident fluid. These zones then become even more permeable as they fill with lower viscosity fluids as a result of extensive water flooding. This further increases the flow of waterflood brine through these high permeable zones and by-passing the oil saturated strata. Therefore any technology that could selectively plug up these high flow zones would be useful for increasing oil recovery because it would redirect the flow of drive fluid into the oil saturated zones. This is particularly important for heavy or moderately heavy oil wherein the viscosity of the oil is much higher than the waterflood drive fluid.

Microorganisms are believed to achieve increased oil recovery by one or more of the following mechanisms: (a) reducing viscosity by degrading higher molecular weight hydrocarbons, (b) producing carbon dioxide which is dissolved into the remaining in-situ oil, (c) producing organic acids which dissolve cementing materials in the formation thereby creating flow passages, (d) producing surfactants that reduce interfacial tension or (e) physically displacing the oil adhering to particles of sand in the formation. These mechanisms have been proposed, among others, in early U.S. patents and publications. For example, U.S. Pat. No. 2,907,389, Hitzman; U.S. Pat. No. 3,032,472, Hitzman; U.S. Pat. No. 2,660,550, Updegraff, et al. have all reported that many types of bacteria can increase oil recovery by a number of not completely understood mechanisms.

One possible mechanism that has been proposed is the production of biopolymers and biofilms that can decrease permeability of the porous reservoir material so much so that it prevents flow into the affected zone. Many of the natural bacteria indigenous to oil bearing formations are capable of forming biofilms. The ability of bacteria to produce a biofilm is believed to give the bacteria an added survival advantage over non-biofilm formers as a way of controlling its environment and maintaining moisture during dehydrating conditions.

Blocking of the affected zone will redirect the flow of fluids into other regions of the formation which contain unrecovered oil. If this bioplugging occurs in a high water swept zone the decrease in permeability will result in more flow into the oil saturated zone. This redirection of flow can increase oil production. Therefore the use of microorganisms to enhance sweep efficiency in waterfloods has been proposed wherein the microorganisms would plug the most porous portions of the reservoir, thereby reducing the tendency of water to "finger" (move through the porous material in an irregular pattern with some streams of fluid penetrating ahead of others) through the high flow zones of the reservoir and leave oil behind.

Placement of Microbes in the Thief Zones of the Formation

Microorganisms that can be stimulated to plug high flow zones may be indigenous native microorganisms preexisting in the formation. The term "native microorganisms", as used herein, refers to a variety of microorganisms that naturally exist in the subterranean target site. "Exogenous or injected microorganisms" refers to microorganisms that are grown outside of the subterranean target site and are then introduced into the site. This may include microorganisms that were isolated from the target or other subterranean site and then grown outside of the subterranean site before introduction. In one mode specialized cultures of natural, mutated or microbes genetically altered by methods of genetic engineering may be injected into the reservoir. Naturally-occurring microorganisms are known to exist in oil bearing formations, so that any existing microorganisms in such formations have invaded as contaminants of the water used in waterfloods, or as contaminants of the water in active aquifers underlying the oil bearing formation which invades the formation at some time in its existence. Numerous proposals have been made to introduce microorganisms into oil-bearing formations either to supplement existing microorganisms or to colonize the formation. However, these techniques have been unsuccessful because the microorganisms tend to be filtered out at or near the formation face, resulting in severe flow restriction into the formation, or plugging close to the point of injection. Although the goal of injecting microbes may include plugging the high flow zones or thief zones, it is necessary to penetrate far into the formation to reach the thief zone. Therefore penetration of exogenous microorganisms deep into the formation is an important issue for MEOR that employs exogenous microorganisms.

An early method was high pressure injection to open the reservoir by hydro-fracturing. Bond in U.S. Pat. No. 2,975,835 disclosed a method of fracturing the formation with high pressure fluid containing bacteria to reach the remote portions of the formation. Later when it became apparent that many petroleum containing formations contained dormant microorganisms L. Brown in U.S. Pat. No. 4,475,590 suggested simply injecting nutrients to stimulate indigenous microbes already well distributed throughout the reservoir, but, that are dormant because the bacteria lack of proper nutrients for growth. In another approach, Sheehy in U.S. Pat. No. 4,971,151 disclosed a method of analyzing the type of indigenous microbes to select a nutrient that simulated growth. Nutritionally the oil and formation brine are deficient in usable sources of both nitrogenous- and phosphorus-containing compounds. This lack of nutrients tends to prevent growth of most microorganisms, or at best permits growth at a very slow rate. Since microorganisms require water and are generally holophytic (they require their nutrients in solution), and since crude oil is not miscible with water, growth of microorganisms must take place primarily at the oil-water interface. All necessary elements and water must be present for growth and metabolism to take place. An adequate carbon and energy source is readily available in the reservoir in the form of crude oil, so that if proper nutrients are provided growth of the microorganisms can be stimulated. These two methods are limited to indigenous microorganisms and may be unpredictable and difficult to control.

A factor in the penetration of injected microorganisms is the size and cell surface of the organism being injected. Smaller bacteria may penetrate the formation easier than larger bacteria. Cells making extracellular polymers are more likely to adhere to the rock surface. The spores of different bacteria may be used for injection to penetrate even deeper. Spores penetrate a reservoir formation easier and become lodged in these highly permeable zones. When they are stimulated to grow by a nutrient solution, they will then start to grow that then plugs more pores more effectively and deeper into the formation. Some inventors have disclosed injecting bacterial spores downhole followed by a nutrient solution [see U.S. Pat. Nos. 4,558,739 and 4,799,545. Others have used non-spore forming bacteria that become very small when starved by limiting the nutrients during fermentation. These bacteria do not make biofilms because they are nutrient limited when injected. Later, after they have penetrated deep into the reservoir, the nutrients are injected [see U.S. Pat. No. 4,800,959]. Recently Alsop et al. in U.S. Patent Application Publication Number 20120273189 disclosed that a nutrient mixture containing lactate could prevent biofilm formation at the injection well and that a later change to acetate could promote biofilm formation in certain select bacteria as a means for delaying the production of biofilm for bioplugging.

There are a number of methods known in the art that utilize the biomass of the bacteria and the biofilm produced by the bacteria as effective means for closing off zones of high permeability and thereby changing it to a very low permeability zone. However, none of these methods are able to control bacteria to produce cell free or soluble polymer that is not attached to the bacteria cells and that can flow with the drive fluid and increase its viscosity as it moves into the oil saturated zone, without the formation of plugging biofilm. In this mode it is preferred that none of the microorganisms in the reservoir formation produce a plugging biofilm that could restrict the flow of the waterflood drive fluid into the oil saturated zone. Also in the preferred mode, the native bacteria are prevented from producing a biofilm that sequesters the soluble extracellular polymers produced by the exogenous microorganisms into the biofilm.

SUMMARY OF THE INVENTION

The present invention provides methods for increasing the viscosity of the drive fluid for displacing oil from a subterranean formation by the use of microorganisms selected or modified for the ability to produce cell free polymers without the formation of any significant bioplugging biofilm or capsule. The means for obtaining useful oil recovery microbes are described herein, including the isolation, selection, random mutation and engineered site-directed mutation of natural microbes from petroleum containing environment or other natural environments. The microorganisms of the present invention are extracellular-polymer producing organisms that remain motile, and only produce some of the components of the biofilm and not the full bio-plugging matrix of exopolymers attached to cells. These microorganisms thereby increase the viscosity of the drive fluid without forming flow stopping bio-mass of cells and extracellular-polymers.

In one aspect, the invention concerns a method of enhancing oil recovery comprising introducing into an oil reservoir a microorganism capable of growing in an environment of waterflood fluid wherein said microorganism is deficient in its ability to produce a flow restricting bioplug.

In one embodiment, the oil reservoir is selected from the group consisting of underground reservoirs, producing wells, non-producing wells, experimental wells, exploratory wells, oil sands and other sources of heavy oil.

In another embodiment, the growth of said microorganism is able to produce soluble biopolymers.

In yet another embodiment, the microorganism is an archaeon or a bacterium.

In a further embodiment, the microorganism is present in a culture of microorganisms comprising a plurality of microorganisms that are deficient in their ability to produce the flow restricting bioplug.

In a still further embodiment, the plurality of microorganisms are able to produce the soluble biopolymers.

In a different embodiment, the microorganism has the ability to produce surfactants.

In other embodiments, the microorganism is inhibited in acquiring the ability to produce said flow restriction bioplugs from microorganisms indigenous or contaminating the reservoir.

In another embodiment, the microorganism has the ability to utilize simple carbons, such as those selected from the group comprising glucose, sucrose, mannose, starch, glycerin, organic acids, and other simple sugars.

In yet another embodiment, the microorganism is present in a culture of microorganisms comprising a plurality of microorganisms that have the ability to produce surfactants.

In a further embodiment, the microorganism has the ability to produce the soluble biopolymers wherein the soluble biopolymer is a polysaccharide.

In a still further embodiment, the microorganism (i) contains functional genes for the metabolism of carbohydrate and conversion into high molecular weight polysaccharides; (ii) lacks functional genes for the formation of a biofilm; (iii) contains functional genes for the production of surfactants; and (iv) is regulated to express said functional genes and grow in the chemical and physical environment of the waterflood fluid.

In all embodiments, the method may further comprise the step of injecting a nutrient mixture into the reservoir.

In all embodiments, the method may further comprise the step of water-flooding the reservoir with a fluid containing a compound toxic to the indigenous microorganism to reduce the concentration of indigenous bioplug forming microorganisms that have the ability to produce a flow restricting bioplug.

In all embodiments, the microorganism may be naturally deficient in its ability to produce said flow restricting bioplug, and/or may be mutated or engineered to become deficient (or more deficient) in its ability to produce a flow restricting bioplug.

BRIEF DESCRIPTION OF THE DRAWINGS

FIG. 3 illustrates the process for determining the increase in backpressure due to microorganism growth on the sandpack surface.

DETAILED DESCRIPTION OF THE INVENTION

Definitions

Figure 1:
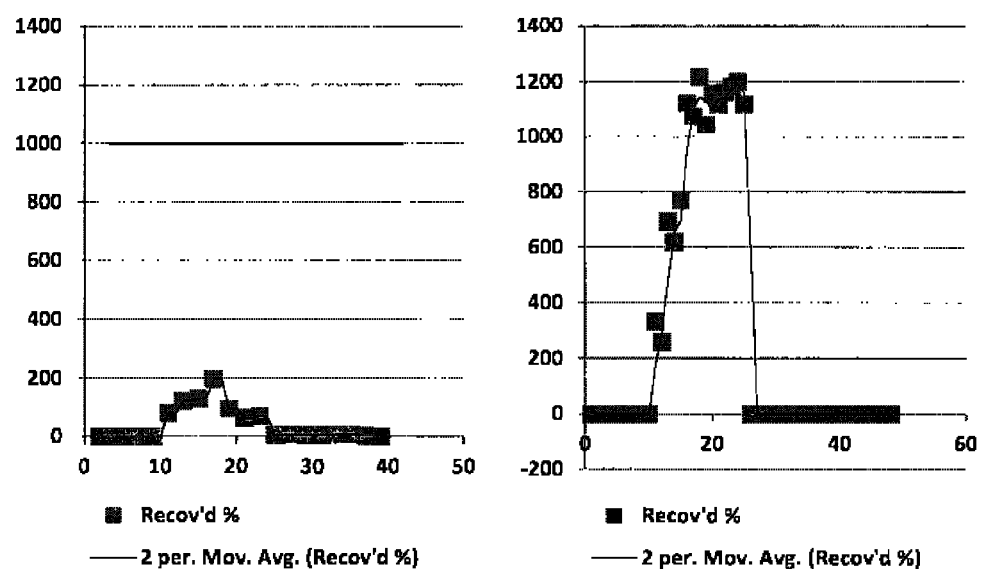
FIG. 1 illustrates a process of determining the increase retention of cells by a sandpack column containing residual oil as compared to a similar sandpack column containing no residual oil.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

It must be noted that as used herein and in the appended claims, the singular forms "a", "and", and "the" include plural referents unless the context clearly dictates otherwise.

Throughout this specification and claims, the word "comprise," or variations such as "comprises" or "comprising," will be understood to imply the inclusion of a stated integer or group of integers but not the exclusion of any other integer or group of integers.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

The term "biofilm" means a complex structure comprising biopolymers, proteins, DNA and bacteria in a "biomass layer" of microorganisms. Biofilms are often embedded in extracellular polymers, which adhere to surfaces submerged in, or subjected to, aquatic environments. Biofilms consist of a matrix of a compact mass of microorganisms with structural heterogeneity, which may have genetic diversity, complex community interactions, and an extracellular matrix of polymeric substances.

The term "plugging biofilm" means a biofilm that is able to alter the permeability of a porous material, and thus retard the movement of a fluid through a porous material that is associated with the biofilm.

The term "bioplugging" refers to making permeable material less permeable due to the biological activity, particularly by a microorganism.

The term "oil reservoir" is used herein in the broadest sense and includes all forms of hydrocarbon deposits, including, without limitation, underground reservoirs, producing wells, non-producing wells, experimental wells, exploratory wells, oil sands and other sources of heavy oil and the like, which may be accessible by any means, such as, for example, one or more wellbores.

The term "crude oil" refers to a naturally occurring, flammable liquid found in rock formations and comprises a complex mixture of hydrocarbons of various molecular weights, plus other organic compounds. Without limitation, the crude oil may contain, for example, a mixture of paraffins, aromatics, asphaltenes, aliphatic, aromatic, cyclic, polycyclic and/or polyaromatic hydrocarbons. The crude oil may be generic or may be from a reservoir targeted for enhanced oil recovery in accordance with the present invention.

The terms "well" and "reservoir" may be used herein interchangeably and refer to a subterranean or seabed formation from which oil may be recovered. The terms well and reservoir include the physical/chemical composition of the soil-rock-sediment structure of the reservoir below the surface.

The term "environmental sample" means any substance exposed to hydrocarbons, including a mixture of water and oil comprising microorganisms. As used herein, environmental samples include water and oil samples that comprise indigenous microorganisms and/or populations of microorganisms of varying genus and species. The environmental samples may comprise a microbial consortium unique to a geographic region or target reservoir, or, alternatively the microbial consortium may be adaptable to other environment sites, geographics and reservoirs.

The terms "microorganism" and "microbe" are used interchangeably and in the broadest sense, including all types of microorganisms, including bacteria, fungi, archaea, and protists, and microscopic animals, such as plankton, planarian and amoeba. Preferred microbes for the purpose of the present invention are bacteria and archaea.

The term "microbial consortium" is used herein to refer to multiple interacting microbial populations. Members of a consortium communicate with one another. Whether by trading metabolites or by exchanging dedicated molecular signals, each population or individual detects and responds to the presence of others in the consortium. This communication enables a division of labor within the consortium. The overall output of the consortium rests on a combination of tasks performed by constituent individuals or sub-populations.

Archaea comprise one of the three distinct domains of life, with bacteria and eukaryotes. For a review, see, e.g. Makarove and Koonin, Genome Biology 4:115 (2003).

The term "halophile" is used herein to refer to an extremophile that thrives in environments with very high concentrations, typically at least about 5% (50,000 ppm), or at least about 10%, or at least about 15% of salt.

The term "obligatory halophile" is used herein to refer to an extremophile whose growth is obligatory dependent on high salt concentrations, typically at least about 5% (50,000 ppm), or at least about 10%, or at least about 15% of salt.

The terms "repression" and "inhibition" with reference to gene expression are used herein interchangeably and refer to any process which results in a decrease in production of a gene product, regardless of the underlying mechanism. A gene product can be either RNA or protein. Gene repression includes processes which decrease transcription of a gene and/or translation of mRNA. Thus, specifically included in this definition are processes that inhibit the formation of a transcription initiation complex along with those that decrease transcription rates and those that antagonize transcriptional activation is gene repression. These repressions can be either reversible or irreversible, both of which are specifically included in this definition.

The term "lateral gene transfer" is used herein in the broadest sense and refers to the transmission of genetic information from one genome to another.

The term "surfactant" as used herein means microbially produced surface-active agents, including, but not limited to, glycolipids (e. g. sophorose lipid or rhamnose lipid), lipoproteins, polysaccharide-fatty acid complexes, mono- and diglycerides, lipoheteropolysaccharides, peptidolipids, neutral lipids, corynomycolic acids, trehalose dimycolates and polysaccharide-protein complexes.

The term "hydrocarbon" is used herein in the broadest sense to describe any organic compound that contains only carbon and hydrogen. The term specifically includes, without limitation, straight and branched chained saturated hydrocarbons (alkanes), straight and branched chained unsaturated hydrocarbons (including alkenes and alkynes), cycloalkanes, and aromatic hydrocarbons (arenes).

A "short chained alkane", as defined herein, contains 1 to 4 carbon atoms.

A "high molecular weight hydrocarbon", as defined herein, is a hydrocarbon having at least about 40 carbons, for example, a hydrocarbon having between about 40 and about 60, or between about 40 and about 80, or between about 40 and about 100, or between about 40 and about 120 carbons.

DETAILED DESCRIPTION

A process is disclosed for better and more reliable microbial enhanced oil recovery (MEOR) that makes use of a species of microorganism or group of microorganisms that produces little or no biofilm. In the preferred mode, the selected microbes remain in the planktonic state, but still produce soluble (non cell attached) exopolymer. Biofilms, which are often comprised of significant amounts of multiple types of polymer, are inhibited or prevented from being formed. The synthesis of biopolymers is highly regulated because bacterial survival in a natural wild environment will be compromised if an unnecessary expenditure of metabolic energy synthesizing such large molecules occurs at a time, for example, when energy must be directed to growth. Moreover, the regulation of exopolysaccharide synthesis and assembly is very complex because a large number of proteins are required to create and export these macromolecules. A typical biofilm is comprised of several individually produced biopolymers. In addition, the complex structure of the biofilm may require proteins and DNA polymers that strengthen the structure and facilitate the attachment to the rock surface. Each of these biofilm elements are coded for and controlled by groups of sequences of DNA or genes in the cell's genome. Therefore, by a number of gene deletions or changes, biofilm producing microorganisms that may have been used for MEOR in prior art methods can now be converted to a new strain of microorganism with attenuated biofilm formation capabilities. Furthermore, by use of a laboratory screening method, each of these gene and gene cluster changes can be evaluated for its effect on the cells' ability to increase viscosity of the media, adherence to rock surfaces, or formation of a biofilm that plugs porous material such as a sand pack column or a reservoir core sample.

A useful step in the selection of a wild-type, randomly mutated or engineered site-directed mutations deletions and gene additions for improved oil recovery (IOR) is a fast laboratory scale screening test. In a preferred mode, the screening assay selects for soluble polymer production, migration of cells through porous media, lack of attachment to solid surfaces and lack of biofilm formation. A preferred screening test selects cells that have undergone change in phenotype related to biofilm/bioplugging and soluble biopolymer production. Preferably, the screening test is fast and able to screen a large number of mutants. It is expected that relatively few altered cells will be able to grow, produce soluble biopolymer and not produce a full strength biofilm.

One commonly used laboratory method is to spread a small volume of bacteria out on an agar plate so that each colony formed is the result of a single cell. Cell colonies that are producing extracellular polymers (mucoid) will have a different phenotype (domed and shining or glistening) than those cells that do not produce extracellular polymers (non-mucoid and dense). Colonies of biofilm forming cells also have a wrinkled appearance and grow to more height than non-biofilm forming microorganisms (see Aamir Ghafoor, et al. (2011) AEM 77(15):5238-5246). By this method or similar colonies screening methods known to those skilled in the art of microbiology, one can isolate a few single strain colonies that can produce extracellular polysaccharides and not lull biofilms from hundreds or thousands of single cell colonies.

In this mode microbes are selected or are modified at the genetic level to reduce their ability to build a biofilm or to form a bioplug in porous material. A new and non-bioplugging microbe that can grow without producing a biofilm allows for penetration of the microbe deeper into the reservoir than previously reported for biofilm capable microbes. This is an advantage for its use in MEOR because of its ability to penetrate more deeply will still in active growth. The non-bioplugging microbe is selected or genetically modified such that soluble and cell free polymers are continually formed or regulated in its production within the reservoir. In situ polymer production will improve mobility control by increasing the viscosity of the drive fluid as it becomes diluted by the resident water within the reservoir.

An important element of this invention is production of cell free and soluble polymers within the reservoir and not the production of a biofilm or capsule which can unduly restrict the flow of fluid into the formation. The benefits of production of biopolymers within a reservoir are described in MEOR prior art, but in the context of biofilms/bioplugging. Most microorganisms that can form a biofilm will also make cell free and soluble polysaccharides. However, the soluble polysaccharides and biopolymers can become associated with the biofilm structure. In that mode, the bound biopolymers are not as effective at increasing the viscosity of the drive fluid. In the preferred mode the soluble polymers flow just ahead of the bacteria with the drive fluid to displace the oil and form an "oil bank" (a zone of displaced oil at the front edge of the waterflood). The invention presented here makes a distinction between biopolymer formation in biofilms that can result in plugging and the decrease of flow in a high flow zone and the production of soluble (cell-free) biopolymer for increase of drive fluid viscosity.

From a practical standpoint, it may be difficult to inject sufficient quantities of actively growing microorganisms into a formation to effect appreciable change. Sand filters are highly efficient in removing polysaccharide producing microorganisms in water purification plants, and the sand in a typical reservoir formation would probably filter out a large portion of the microorganisms at or near the formation face at the wellbore. However, microorganisms that are spores or are attenuated in the ability to form a biofilm and have increased motility due to lack of attached biofilm are more likely to penetrate deeper into a reservoir than biofilm forming contaminating microorganisms. Therefore microorganisms that have been selected or mutated to not produce a biofilm have an advantage in that they can penetrate further into a reservoir while being given sufficient quantities of nutrient for growth. For example, it is believed that the first step in the transition from motile or planktonic state to a biofilm is an attachment to a solid surface. Therefore, some of the genes that are needed for the change from a planktonic state to a sessile state code for proteins or biopolymers that mediate attachment to solid surfaces. If these genes are inactivated a mutant form of the microorganism could be less able to attach to the sand surface and would stay in the supernatant or flow through a small sand pack column. The propensity of individual cells to adhere to solid surfaces can be screened in a fast and high through-put mode by a small scale mixing with sand or passing through a small sand pack column. This method or a procedure similar to this could be used to enrich for non-adherent mutants.

However, indigenous microorganisms that are biofilm producers can pose a problem in the method of the present invention. The injection of new fluids may cause introduced growth due to the injection of growth nutrients. Oil-degrading microorganisms are capable of sustaining a minimal population in most underground petroleum formations but do not flourish. Crude oil provides adequate carbon and energy, but is nutritionally deficient in both nitrogen and phosphorus. Most microorganisms are known to occur in microbial populations which are in a state of starvation. In the case of microorganisms existing in a subterranean hydrocarbon-bearing formation, the nutritional deficiencies are primarily nitrogen- and phosphorus-containing compounds, not carbonaceous materials. The injection of those compounds in amounts that is nutritionally sufficient for the injected attenuated biofilm soluble biopolymer producing microbial population can result in the growth of the indigenous microorganisms. This is a potential problem because the indigenous microbes are generally able to produce biofilms. The production of a biofilm mass can form a permeability reducing bioplug regardless of whether it is from indigenous microbe or injected microbes. Microbial utilization of crude oil by indigenous microbes can also chemically change the nature of hydrocarbon constituents of the crude oil and thereby change the properties of the oil. The depletion of short chain aliphatic compounds, for example, may increase the viscosity of the oil.

Therefore, to prevent the interference of indigenous microorganisms that are capable of producing plugging biofilms and/or degrading short chain hydrocarbons and increasing the viscosity of the oil, a step can be added to kill or suppress the indigenous microbes. One method of suppressing growth of indigenous microbes that will favor the growth of injected microbes is disclosed in U.S. Pat. No. 8,316,933 (Kohr). Another method is disclosed by in U.S. Patent Application Publication No. 20130062053 (Kohr et al.). Both methods are hereby incorporated by reference. These methods rely on a drive fluid that is chemically different than aqueous fluid that has existed in the oil reservoir prior to oil production. Furthermore, the high salinity, pH or concentration of toxic chemical elements will kill or suppress the growth of the indigenous microorganisms. The objects of those inventions are to give the host or recipient organism a competitive advantage for the specially modified environment of the hydrocarbon resource reservoir before and/or during a waterflood oil recovery process. This process kills indigenous microorganisms that can interfere with the injected microbes. The injected microorganisms are adapted to the injected fluid and benefit from the environmental and chemical changes that result from introducing a new fluid into the oil containing formation. That is, the modified microorganisms are designed to thrive in the new reservoir environment of chemical waterflooding not in the preexisting environment. In a non-limiting example, the new conditions can be a higher pH, salinity, or temperature or a compound that is toxic to most of the indigenous bacteria but that is not toxic to the injected microbes.

For the purposes of this invention, the exact identity of the specific microorganisms is unimportant as long as they have been selected, mutated and/or genetically altered to produce soluble polymers and/or surfactants without the ability to form cell restricting bioplugs and enhanced adhesion to the rock surface. Representative microorganisms, which may be present either singly or in combination, are represented by microorganisms that comprise classes of aerobes, facultative anaerobes, obligate anaerobes and denitrifiers. Various species of microorganisms (bacteria and fungi) that can be used to improve sweep efficiency and enhance oil recovery include, but are not limited to, the genera: *Pseudomonas, Bacillus, Geobacillus, Sphingomonas, Actinomycetes, Acinetobacter, Arthrobacter, Halomonas, Diomarina, Schizomycetes, Clostridium, Corynebacteria, Achromobacteria, Arcobacter, Enterobacteria, Nocardia, Saccharomycetes, Schizosaccharomyces, Vibrio, Shewanella, Thauera, Petrotoga, Microbulbifer, Marinobacteria, Fusibacteria*, and *Rhodotorula*. The terms "genus" and "genera", as used herein, refer to the category of microorganisms ranking below a "family" and above a "species" in the hierarchy of taxonomic classification of microorganisms. The term "species" refers to a group of microorganisms that share a high degree of phenotypic, biochemical and genotypic similarities. The oil-degrading microorganisms utilized in the experiments reported herein were isolated from crude oil environments or other environments using conventional microbiological techniques.

Isolation of a small fraction of a diverse population of microorganisms can be done by relying on a phenotypic or functional difference that the subpopulation displays. In one non-limiting example microorganisms are isolated that lack the ability to form a strong adhesion to a solid sand surface. In this example, a strain of *Bacillus* or *Pseudomonas* that is known to be capable of forming a biofilm is treated under conditions that are known to produce mutations. A 100 to 500 ml culture of log phase microbes is added to 10 to 50 gm of washed, clean, fine material sand. The mixture is rolled slowly in a roller bottle to allow for good mixing and attachment of cells to the sand surface. Samples of culture solution are removed at several time points, from one hour to three days. Total cell concentration is determined by counting with a microscope and a Petroff-Hausser Counting Chamber (Electron Microscopy Sciences) and or a viable cell concentration is determined by plating out diluted samples on agar plates and subsequently counting colonies. Another method is reported by E. A. Robleto et al. in J. of Bacteriology Vol. 185 No. 2 p 453-460 (2003). In this referenced method bacterial strains grown overnight in LB broth were inoculated into 12 ml of minimal medium broth and grown to an $A_{530}$ of 0.4 to 0.5. Cells were centrifuged for 5 min at 6,000 rpm (Sorvall RC5b Plus), and the pellets were washed twice in PBS. Cells were resuspended in 4 ml of PBS and drawn into a syringe containing 12 g of Ottawa sand (Fisher Scientific catalog no. S23-3). An aliquot of the inoculum was used to determine cell density and allow an estimate of percent attachment. The sand column was allowed to equilibrate for 5 min, and the volume contained in the column was estimated by subtracting the amount that drained out of the column in the first 5 min. Columns were incubated for 1 to 1.5 h and washed with 1× equilibration volume. Washes were serially diluted, plated onto LB agar with appropriate antibiotics, and incubated at 28° C. Viable-cell counts from washes were used to estimate percent attachment on the basis of the initial number of viable cells in the inoculums.

By either of these methods, the media suspension or the cells first eluted off the small columns will be enriched in cells that do not attach to the sand particles. Following repeated iterations of this enrichment process, the percentage of cells that do not attach will increase in the media suspension. The culture of enriched non-adherent microorganisms can be plated out on growth agar. Single colonies that show a shiny or glistening, mucoid phenotype, which are believed to be polymer producers, will be selected for further analysis. The selected colonies will be transferred to multi-well microtiterplates (#353047, BD Biosciences) or to test tubes containing growth media to screen for isolates that to not form biofilms or pellicles. The test tubes containing 5 to 10 ml of media will be incubated for four days without shaking as described by Friedman and Kolter 2004 Mol. Microbiol. 51:675-690. Several isolates will be screened in test tubes and microtiter plates to identify those that grow, but do not form pellicles or biofilms.

The invention is further illustrated by the following non-limiting Examples.

Example 1

Screening for Polymer Production

Plate assays are carried out for polymer production, in which cells are treated under mutagenic conditions, plated on rich agar plates, and incubated to allow colonies to form. Colonies are screened for a visible mucoid appearance. (as described in Mathee et al., 1999 Microbiology 145:1349-1357). In an earlier reference Darzins and Chakrabarty (1984) in J. Bacteriol Vol. 164 p 516-524 reported isolating 21 non-mucoid mutants of *Pseudomonas aeruginosa* strain 8821 by screening 4 thousand colonies that had been mutagenized with EMS. The non-mucoid producing mutants were recognized by their inability to produce a "typical mucoid colony" on solid media. The 21 colonies were tested by growth on a media with a simple carbohydrate as the only carbon source to make sure that the lack of alginate synthesis was not due to genes controlling all carbohydrate metabolisms. This lead to cloning the genes controlling alginate biosynthesis from mucoid cystic fibrosis isolates of *Pseudomonas aeruginosa*.

A similar screening procedure can be used to isolate mutants that do not adhere to sand from the above sand adhesion isolation, but still produce soluble polymers to give the colony a mucoid appearance. In this mode mutant strains can be isolated that produce soluble and unattached exopolysaccharides, but that do not form a strong adhesion to a sand surface. These mutants would be useful in moving through the formation with the waterflood drive fluid while producing viscosity increasing soluble polymers. In another mode, this screening procedure could be used to isolate the genes that control attachment of cells to the sand surface and the start of biofilm formation and the genes which may be different that control the production of cell free and unattached soluble polymers. Identifications of these genes can be used to further modify the wild type bioplugging biofilm producing microorganisms into planktonic soluble polymer and or surfactant producing strains by site directed mutagenesis and other gene manipulation techniques.

Example 2

Screening for Biofilm Forming Microorganisms with Glass Beads

Screening of isolated strains for their ability to form biofilms on silicate surfaces under aerobic and anaerobic conditions was disclosed by Keeler et al. in U.S. Pat. No. 8,357,526. Sterile glass beads (3 mm, #11-312A, Fisher Scientific, Hampton, N.H.) were placed into the wells of a 24-well microtiter plate. Aliquots (1.0 mL) of either the Injection Water or the PPGAS medium (20 mM NH.sub.4Cl, 20 mM KCl, 120 mM Tris-Cl, 1.6 mM MgSO.sub.4, 1% peptone, 0.5% glucose, pH 7.5) were added to each well. Samples (10 u.L) of overnight microbial cultures were then added, and the plates were incubated at room temperature for up to one week. Glass beads were examined by microscopy directly in the microtiter wells. To quantify the anaerobic formation of biofilms across different strains, single colony isolates were grown anaerobically in 1.0 mL Injection Water supplemented with 1600 ppm sodium nitrate. Silica beads were added into the wells of a 96-well microtiter plate (#353070, BD Biosciences). After eleven days of anaerobic incubation, the beads were removed from the wells, rinsed in sterile water, and transferred to a new microtiter plate. Crystal violet dye (75 u.L, 0.05%) was added to each well, and the plate was incubated at room temperature for 5 min. The dye was then removed by washing each bead (times. 4) with 200 u.L sterile water. To remove the bacteria from the heads and solubilize the remaining dye, 100 u.L of 95% ethanol was added and samples were incubated at room temperature for 20 min with intermittent mixing. Aliquots (10 u.L) were removed and added into 90 u.L sterile water in a new microtiterplate. Absorbance of each sample at OD.sub.590 was measured in a Victor3 (Perkin Elmer, Waltham, Mass.) plate reader to quantify the dye reflecting the relative concentrations of microorganisms that were attached to the silica beads.

Example 3

Determination and Assay of Amount of Biofilm Formed

Biofilm formation in microtiter plates was determined essentially as described previously (O'Toele, G. A., and R. Kolter. 1998. Initiation of biofilm formation in *Pseudomonas fluorescens* WCS365 proceeds via multiple, convergent signalling pathways: a genetic analysis. Mol. Microbiol. 28:449-461). Cells were grown in liquid cultures in microtiter plates (0.2 ml) for 18 h in M9Glu/sup at 30° C. The liquid culture was removed, and the cell optical density at 600 nm ($OD_{600}$) was determined spectrophotometrically. Cells attached to the microtiter plates were washed with 0.1 M phosphate buffer (pH 7.0) and then stained for 20 min with 1% crystal violet (CV) in ethanol. The stained biofilms were thoroughly washed with water and dried. CV staining was visually assessed, and the microtiter plates were scanned. For semiquantitative determination of biofilms, CV-stained cells were resuspended in 0.2 ml of 70% ethanol, and their absorbance was measured at 600 nm and normalized to the $OD_{600}$ of the corresponding liquid culture.

Isolation and purification of extracellular biopolymers can be done by growth of cells to stationary phase followed by centrifugation of cells to form a cell free supernatant that can be precipitated with the slow addition of ethanol to an equal volume of each. After overnight chilling to −18 degrees Celsius, the polymer mixture is centrifuged at 13,000 g for 30 minutes to make a pellet. The pellet can then be washed with cold ethanol and then dissolved in hot water and then dialyzed against distilled water. The lyophilized polymer can be weighed or further purified for analysis.

Example 4

Method of Screening for Microbial Penetration, In-Situ Polymer Production or Biofilm Formation by Means of Sandpack Columns Small sandpack columns can be used to screen a number of plate isolated genetically modified or wild type bacteria. This method evaluates the strain isolates for their ability to travel through porous media, form a stable biofilm in porous media and increase the viscosity of the transport fluid. The change in pressure at constant flow is used to determine the decrease in permeability caused by bacterial growth. A glass column 8×150 mm (#5813 Ace Glass) is fitted with a #7 Ace Glass Teflon end fitting (35801-7 Ace Glass). A small plug is made out of stainless steel wool as a sand filter for each end fitting. The column is filled with fine sand while tapping to compact the sand. The dry-packed column is then filled with water while evacuating with a vacuum to remove any air pockets. The water is pumped into the column at about 0.5 ml per minute by means of a peristaltic pump with a tee connection to a pressure gauge. Sterile media is then pumped into the column to replace the water. After at least two pore volumes of media have been pumped into the column, the pressure and the flow rate are recorded. A culture of microorganisms to be tested is then pumped into the column. The volume is at least one pore volume and the number of cells per ml is estimated by counting with a microscope in a Petroff-Hausser Counting Chamber (Electron Microscopy Sciences) or by plating out dilutions to determine the viable cell count. If the cultures of microorganisms for testing are anaerobes or facultative anaerobes, the columns are allowed to stand without flow for 3 to 15 days to allow for cell growth. After the incubation period, one pore volume of sterile media is pumped into the column. The pressure and flow rate are recorded and used to calculate change in permeability. The volume of liquid replaced from pumping the column with fresh media is collected and analyzed for viscosity and cell concentration (number of cells per ml). This process is repeated with several new pore volumes of media to determine the change in permeability with time and to determine the viscosity and the number of cells in the liquid eluted off of the sand column. The degree of plugging can be determined by the change in pressure with a constant flow rate or by the change in flow rate if flow rate at a constant pressure. If the viscosity of the pore volumes of fluid eluted from the column as measured separately the change in permeability as a result of the cell growth and biofilm formation in the porous media can be determined by Darcy's law. The number of pore volumes that are needed to be pumped through the column to increase the permeability back to the original state is a function of how stable and strong of a bioplug the strain produced. The rate at which the cells are washed out of the column is a function of how adherent the microorganism is to the sand. This method can be used to rate the various strains or mutations in regards to their ability to migrate through porous media, form a strong bioplugging biofilm or increase the viscosity of the drive fluid by producing soluble polymers that are not attached to the sand, cells or biofilm.

In particular, sandpack columns can be used to screen a number of isolated genetically modified, mutated or wild type bacteria. This method evaluates various microbial strains for their ability to aid in oil recovery by one of several mechanisms including: penetrating through porous media, forming a biofilm plug in a highly porous zone or increasing the viscosity of the transport fluid by secreting cell free soluble polymers. Columns can be made of varying permeability by packing a column with sand of various size distributions. The permeability can be decreased by addition of finer sand or by grinding the sand to finer size profile in a Drum Rotary Tumbler (Chicago Electric Power Tools #67632 sold by Harbor Freight Tools). The pressure at constant flow is used to determine the permeability constant in Darcys by the Darcy equation:

$$Q=-kA \text{ (pressure drop)}/uL$$

Where Q is flow in milliliter (ml) per second, A is area in square centimeters, L is the length in centimeters, the pressure drop is in atmospheres, u is the viscosity in centipoises. The permeability constant k is in Darcys.

A simple test column is constructed from ½ inch PVC (polyvinyl chloride) schedule 40 tubing which is available at home building supply centers such as Home Depot. To construct a column, the ten foot PVC tube was cut into 5 foot in length and then capped with threaded PVC end caps using PVC glue. This simple column will withstand 20 to 30 atmospheres of pressure. The column can also be cut into small sections for analysis of the packed sand after the microbial elution and plugging tests. A small sand filter is made out of 200 mesh/75 micron stainless steel screen (owfb store on Ebay) and placed into a threaded PVC female end cap which has a threaded Swagelok ⅛ inch compression fitting. The column is filled first with water, fine sand is poured in while tapping to compact the sand. The threaded end cap is replaced onto the column to prevent the loss of water or sand to prevent voids for forming in the sand packed column. The sandpack column can be used for experiments testing microbial penetration, in-situ polymer generation, the formation of a flow restricting bioplug or biofilm.

Microbial Penetration:

The ability of microorganisms to penetrate porous material is a function of the microbe's size, motility and affinity for the surface of the porous material. The microbe's surface affinity is a function of the surface nature of the porous material, such as clean sand vs. oil covered sand. The cells attraction to the porous material's surface is also a function of the growth state of the microbe from vegetative to starved or sporulated cells. Therefore, various strains of microbes should be compared in the same growth state on columns of similar surface nature and permeability.

Sterile water or brine is pumped into the column at about 0.5 ml per minute by means of a peristaltic pump (Manostat cassette pump model 72-500-000), or a higher pressure pump (Millipore-Waters M-45 lab chromatography pump, HPLC solvent delivery system), with a tee connection to a pressure gauge to measure any change in pressure. Sterile media to maintain the cells in the selected growth state is then pumped into the column to replace the water. After at least one or more volumes of media have been pumped into the column, the pressure and the flow rate are recorded and used to calculate the permeability. A culture of microorganisms to be tested is then pumped into the column. The volume is at least one pore volume and the number of cells per ml is estimated by plating out dilutions to determine the viable cell count. Volumes of column effluent are collected analyzed by plating and colony counting. This method is used to estimate the number of pore volumes needed to elute the cells and also an estimate of the approximate or relative recovery of cell that can pass all the way though the length of sandpack column. In FIG. 1 the relative recovery is plotted against the elution volume. The graph on the right shows that the small alkalophilic bacteria isolated by 0.2 um filtration from the water from Mono Lake as described in Example 9 is eluted in about one pore volume. The graph on the left in FIG. 1 is the amount of the same bacteria applied to the same size sandpack column that was first saturated with oil and then eluted with about 5 pore volumes of water so that a small residual oil remained. The relative recovery of microbes was about 20% of that from the clean sandpack column suggesting that some of the cells were adhered to the oil. This method can use different size sand particle distributions for different permeability, clean sand vs. oil wetted sand, or columns made by coating sandstone core sample with fiber glass epoxy.

Figure 2:
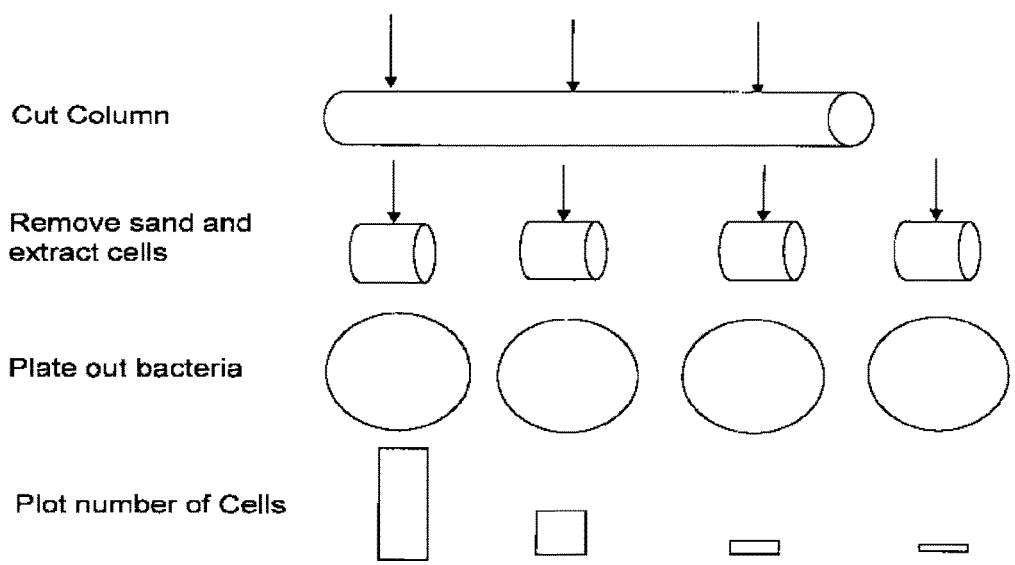
FIG. 2 illustrates the procedure for analyzing a sandpack column made of PVC tubing for remaining microorganisms and biofilms after elution. Each cut section can be analyzed for retained cells and or biofilm polysaccharide.

After eluting the sandpack column with several pore volumes, the number of microbes retained by the sand or oil-sand surface can be estimated by cutting the PVC column into small sections and removing the oil-sand-fluid and bacteria mixture from each section as shown in FIG. 2. Viable microbes can be counted by a quantitative extraction from the sand mixture with media and plated out. Plated out colonies can also be identified by DNA analysis. Un-extractable, dead cells or cells strongly adhered to the sand surface in a biofilm can be measured by addition of Crystal Violet reagent solution to determine polysaccharide content, or by 6 normal hydrochloric acid hydrolysis in vacuum for 24 hours at 100 degrees C. followed by amino acid analysis for an estimation of total protein.

Procedure for Quantifying Adhered Biofilm on Sandpack Columns

About 25 grams of sand containing the bacteria, biofilm along with the liquid is removed from each section of the cut PVC sandpack column. The sand mixture is then transferred to a 50 ml tube. 30 ml of brine or water is added to each tube and gently mixed to remove unattached cells. The 30 ml wash process is repeated three times. The first wash is used to plate out viable cells. For oil containing sand, the residual oil can be extracted from the wet sand with 30 ml of toluene. If the sand still contains oil a second toluene extraction can be done. The oil is removed to prevent possible interference with the biofilm assay. After the toluene layer is removed, the sand is placed in an open dish and allowed to dry for about one hour. A fraction of the sand of about 1.0 ml volume is removed and placed in a tube for Crystal Violet biofilm analysis. A 0.5 ml volume of a 0.1% Crystal Violet solution is added to each tube containing sand and gently mixed with the sand. The mixture is incubated for about 15 minutes. After that, 3 ml of water is added to each tube with gentle mixing. After the sand settles out the liquid above the sand is removed. The 3 ml wash process is repeated three times to remove the excess Crystal Violet solution. After as most of the final wash water is removed from the sand in the tube, 3 ml of 95% ethanol is added to each tube to extract the Crystal Violet dye from the biofilm attached to the sand. After vigorous mixing, the ethanol sand mixture was allowed to settle out for 10 minutes. Then 1.0 ml from the liquid layer was removed and the absorbance at 600 nm was measured. The absorbance of the ethanol extracted dye is a function of the amount of biofilm adhered to the sand in each section of the sandpack column. The absorbance of each section can be plotted verses the distance from the injection of bacteria to determine the amount of bio-plugging that occurs near the point of entry or injection.

By these methods of analysis microbial strains can be compared by their ability to penetrate through porous sand without a large percentage of the cells being retained on the sand surface near the point of introduction, or forming a bio-plug near the point of entry known as face plugging. In addition, in the case of culture believed to contain a number of mutated cells, mutants that have lost the ability to adhere to the oil-sand surface will be enriched in the breakthrough volume of eluted cells. Therefore this procedure can be useful to select mutants for deeper penetration into an oil formation without forming a bioplug near the injection well.

In-Situ Production of Cell Free Polymers to Increase the Viscosity of the Drive Fluid:

Microbes that produce and secrete cell free or soluble polymers can increase the viscosity of the fermentation broth. This ability to increase the viscosity of the broth is a function of the genetics of the microbial strain, media and carbon source, the oxygen level and shear force due to mixing. Therefore, to evaluate the ability of microbial strains to increase the viscosity of the drive fluid as it moves through the formation, the growth of microbes should be in a sandpack column or a sandstone core. The PVC sandpack column described can be used to screen strains for this ability. If the cultures of microorganisms for testing are anaerobes or facultative anaerobes, the columns are allowed to stand without flow for 3 to 15 days to allow for cell growth. This will test cell growth and polymer secretion in a static no flow situation. Alternatively a slow flow condition similar to the rate of propagation of drive fluid through a formation can be approximated with several 5 foot columns connected in series, so that the fluid eluting of the end multi-column system has had 5 to 10 days for the growth of microbes and production of polymer as the fluid migrates at one to two feet per day. After the incubation period, a small volume of sterile media is pumped into the column. The pressure and flow rate are recorded and used to calculate the total change in permeability. The production of polymer by the microorganism will increase the pressure when pumping the column. This method can be used to compare various strains to cause plugging of a high permeability zone. FIG. 3 shows 4 different microbial stains applied to 4 different 5 foot sandpack columns and incubated for up to 8 days. After about 5 days there was a larger increase in back pressure on the column inoculated with *Pseudomonas toyotomiensis* and *Bacillus mojavensis* JF-2 than the columns inoculated with *Pseudomonas alcaliphila, Marinobacter hydrocarbonoclastica* or *M. alkaliphiles*. This indicates that either a biofilm formed or the bacteria produced cell free biopolymers or both have restricted the flow.

The volume of liquid replaced as a result of pumping the column with fresh media is collected and analyzed for viscosity and cell concentration (number of cells per ml). If microbial cells are present, the fluid can be centrifuged to remove cells so that the viscosity of the cell free polymer can be measured without the presence of cells. A new permeability constant can be calculated by the Darcy equation using the new viscosity of the eluded fluid. If the permeability constant is calculated to be the same, then most of the increase in backpressure is from the increased viscosity from the secreted polymers. If the calculated permeability constant remains lower than the original value of permeability after the viscous fluid is eluted, then the decrease in permeability is the result of microbial growth within the column and the formation of a biofilm. By this means, strains of microbes can be selected for their ability to produce cell free polymer that can increase the viscosity of the drive fluid, or to select strains that form biofilms and block flow to a zone.

The degree of plugging can be determined by the change in pressure with a constant flow rate, or by the change of flow rate at a constant pressure. The viscosity of the pore volumes of fluid eluted from the column as measured separately is a different property of cell growth than the change in permeability as a result of the cell growth and biofilm formation in the porous media. The number of pore volumes that are needed to be pumped through the column to increase the permeability back to the original state is a function of how stable and strong of a bioplug the strain produced. The rate at which the cells are washed out of the column is a function of how adherent the microorganism is to the sand. This method can be used to rate the various strains or mutations in regards to their ability to migrate through porous media, to form a strong bioplugging biofilm, to increase the viscosity of the drive fluid by producing soluble polymers that are not attached to the sand, cells or biofilm.

A similar sandpack column test can be used for aerobic microorganisms. In the aerobic mode a slow flow rate of media is circulated through the column to maintain a higher dissolved oxygen level. Sterile, filtered air is used to aerate the circulating media. Alternatively a mixture of air and liquid can be pumped through the column to maintain a high level of dissolved oxygen. Aerobic microbial oil recovery process have been disclosed by L. W. Jones in U.S. Pat. No. 3,332,487 issued in 1967 and by E. Sunde in U.S. Pat. No. 5,163,510 issued in 1992 and U.S. Pat. No. 6,546,962 issued in 2003. The introduction of air and or oxygen will affect the type of bacteria that predominates the process and the amount of soluble extracellular polysaccharides and the amount of biofilm that is formed. Therefore the microorganisms should be screened and selected for high soluble production without excessive bioplugging under aerobic conditions unless it is desirable to form a stable biofilm or bioplug within a high flow zone to stop the flow of drive fluid into a watered-out or thief zone.

By use of the above screening process with sandpack columns, various strains and mutants of strains or genetically modified strains can be evaluated for the ability to penetrated far into a formation and then alter being over taken by the right media, carbon source or oxygen level produce cell free or soluble polymer that increases the viscosity of the drive fluid for mobility profile modification. Alternatively, strains can be selected for their ability to penetrate into a high flow zone and then be triggered into producing a biofilm or bioplug by following and overtaking the cells with a media that causes a biofilm to form and plug the zone.

Example 5

Making Mutant Microorganisms that Only Secrete Soluble Polymer and are Deficient in Forming Biofilm by the Process of Random Mutagenesis Because the ability to form a biofilm is an advantage to most wild type microorganisms, it may be difficult to isolate otherwise useful bacteria that cannot make stable biofilms. However, because biofilms are comprised of microorganisms embedded in a self-produced matrix of extracellular polymeric substance (EPS) which contains significant amounts of polysaccharides (polymer) of several types as well as proteins and DNA, it may be possible to disrupt the stable biofilm formation process. The formation of a stable biofilm may be disabled or disrupted by randomly destroying genes within a microorganism's genome followed by isolating mutated cells that can still function and grow but that are unable to produce all of the needed components of a stable biofilm. The soluble and cell-free polymer in the biofilm has great potential application in enhanced oil recovery (EOR) because it can move ahead of the growing cells and create a high viscosity fluid to push the oil off of the formation rock. Therefore, the goal is to select a few cells that have lost the ability to make complete stable biofilms, but that still can produce soluble cell free polymer.

Random mutated cells can be generated by a number of methods known to microbiologists such as the use of Acridine Mutagen ICR 191, chemical Ethyl methanesulfonate (EMS), and Ultraviolet (UV) to treat biofilm producing microbes (*Pseudomonas, Bacillus*) to disable their biofilm formation. In this example, the goal is to generate and isolate mutants able to produce water soluble polymer but no biofilm. The new microbial mutants will be used in an oil reservoir for in situ polymer production for increasing the viscosity of the drive fluid in a process of enhanced oil recovery (EOR). Some non limiting examples for cell mutagenesis are given below.

Acridine Mutagen ICR 191 Mutagenesis

Grow cells to log phase, count cell and dilute cells to ~$10^3$-$10^4$ cells/mL, aliquot 10 mL cells in 6 conical tubes, add ICR 191 (stock 5 mg/mL in 0.1N HCl) to final concentration: 0 ug/mL, 1 ug/mL, 2 ug/mL, 3 ug/mL, 4 ug/mL, 5 ug/mL. Treat the 10 mL cells in a rotator (250 rpm) for 7-10 days, then proceed to the screening process.

EMS (Ethyl Methanesulfonate) Mutagenesis

Dilute the log phase cells to $10^5$ cells/mL, aliquot 10 mL, cells in 6 conical tubes, add EMS to final 200 μM, treat the 10 mL cells in a rotator (250 rpm) for 0, 20, 40, 60, 80, 100 minutes, then proceed to the screening process.

UV (Ultraviolet) Mutagenesis

Dilute the log phase cells to $10^5$ cells/mL, aliquot 30 mL cells to 6 petri dishes and expose the cells to following doses of ultraviolet in a Stratalinker UV crosslinker: none (control), $2.5 \times 10^4$ μJ/cm2, $5.0 \times 10^4$ μJ/cm2, $7.5 \times 10^4$ μJ/cm2, $10 \times 10^4$ μJ/cm2, $15 \times 10^4$ μJ/cm2. Proceed to the screening process.

Screening Process

Collect cells of each treatment by centrifugation, then wash the cells three times using the culture medium, and resuspend the cells in 2 mL medium. Spread 0.1-0.5 mL on medium agar plates and incubate at appropriate conditions (eg, aerobic, anaerobic, temperature) for 7-10 days.

Choose mucoid colonies (as described above) and transfer them to liquid medium, incubate for 7-10 days. Choose mutant cells that form no biofilms in liquid culture for further viscosity measurement and polymer quantification. Cells selected from this process should produce a very viscous (high yield of polymer) solution when grown in larger culture with no biofilm formation.

Example 6

Site Directed Mutating of Genes Coding for Biofilm Formation.

Construction of Biofilm Deficient *Pseudomonas* Strains

Defects in the mucA gene in *P. aeruginosa* PAO1 result in an overproduction of the soluble exopolysaccharide alginate (Mathee, K., et al. Microbiology 1999 June: 145 (pt6): 1349-57) and a decrease in some biofilm characteristics including surface attachment (Hay, I. D., et al. Appl Environ Microbiol. 2009 September; 75(18): 6022 6025). Moreover, PAO1 strains containing deletions in the psl gene cluster have defects in attachment to a microtitre dish well and do not form robust biofilm biomass (Colvin, K. M., et al. *Environ Microbiol.* 2012 August; 14(8):1913-28). It has been observed that a PAO1 isolate containing a defect in the mucA gene (strain PDO300) in which the pelF and pslA genes have also been deleted produces high levels of alginate but does not produce the Pel or Psl polysaccharides that are important in biofilm formation.

To generate a *Pseudomonas* strain with a defect in biofilm formation, but with enhanced cell-free soluble polymer production, knockout constructs were generated for *P. aeruginosa* PAO1 (ATCC BAA-47) that were designed to implement an unmarked deletion strategy (as described in Colvin above). Flanking regions of each gene targeted for deletion were synthesized and introduced into the suicide vector pEX100T. The flanks were synthesized as two separate 750 bp DNA fragments (Integrated DNA Technologies). One fragment, partGFF28 (SEQ ID NO: 2), included sequence matching 19 bp from vector pEX100T immediately upstream of the SmaI restriction site, followed by 716 bp of sequence upstream of the mucA gene (716 to 1 nt before the start of mucA), followed by sequence matching 1 to 15 bp after the end of the mucA ORF. The second fragment, partGFF29 (SEQ ID NO: 3), included 16 bp matching 16 to 1 bp before the beginning of the mucA ORF, followed by sequence matching 716 bp downstream of the mucA gene (1 to 716 nt after the end of mucA), followed by sequence matching 18 bp immediately following the SmaI restriction site in pEX100T. The two fragments were combined with SmaI cut pEX100T in an isothermal assembly reaction using Gibson Assembly Master mix (New England Biolabs), at 50° C. for 1 hour, according to the manufacturer's instructions. Assembly of the correct sequence was verified in one isolated plasmid, pGFF173, by DNA sequencing. pGFF173 will be transformed into *P. aeruginosa* PAO1 by electroporation or conjugal transfer from *E. coli*, and single recombination integrants will be selected on LB plates containing 300 μg/ml carbenicillin (and 25 μg/ml irgasan in cases of conjugal transfer). Double recombination mutants will be selected on LB plates containing 10% sucrose, to generate a ΔmucA knockout strain.

Knockout plasmids were generated to knock out the pslD and pelF genes in *P. aeruginosa* PAO1, using a markerless knockout design in the pEX100T vector similar to pGFF173 (above). To generate the pslD knockout construct, a DNA fragment including 525 bp upstream of the pslD ORF was generated by PCR amplification from *P. aeruginosa* PAO1 genomic DNA using DNA primers prGFF695 (SEQ ID NO: 62) and prGFF697 (SEQ ID NO: 64), and a DNA fragment including 527 bp immediately downstream of the pslD ORF was generated by PCR amplication from the *P. aeruginosa* PAO1 genomic DNA using DNA primers prGFF696 (SEQ ID NO: 63) and prGFF698 (SEQ ID NO: 65). Primer sequences included sequences that matched the ends of the SmaI cut pEX100T vector and the adjacent fragment (as with partGFF28 (SEQ ID NO: 2) and partGFF29 (SEQ ID NO: 3), above). The two fragments were combined with SmaI cut pEX100T in an isothermal assembly reaction using Gibson Assembly Master mix (New England Biolabs), at 50° C. for 1 hour, according to the manufacturer's instructions. Assembly of the correct sequence was verified in an isolated plasmid, pGFF174, by DNA sequencing. A pelF knockout construct, pGFF175, was generated in the same manner, using primers prGFF699 (SEQ ID NO: 66) and prGFF700 (SEQ ID NO: 67) for the upstream fragment (480 base pairs) and prGFF701 (SEQ ID NO: 68) and prGFF702 (SEQ ID NO: 69) for the downstream fragment (497 base pairs) at pelF. Subsequent knockouts will be made by the same method employed for the mucA knockout, generating a ΔmucAΔpslD, a ΔmucAΔpelF, a ΔpslDΔpelF, and a ΔmucAΔpslDΔpelF strain.

A cluster of genes that are homologous to the *Pseudomonas aeruginosa* algUmucABCD cluster of genes is present in multiple sequenced *P. stutzeri* genomes, including ATCC 17588, CCUG 29243, DSM 10701, and DSM 4166, with mucA homologs present in several sequenced *P. stutzeri* genomes (DSM 10701, A1501, DSM 4166, ATCC 17588, CCUG 29243, RCH2). Likewise, pslA is present in at least five sequenced *P. stutzeri* genomes and significant conservation of the psl gene cluster is readily apparent (See Tables 2 and 3). However, pelA does not have a close sequence homolog (BLAST E-value <1.0) in sequenced *P. stutzeri* strains.

Primers were designed based on existing *P. stutzeri* genomic sequences with homology to *Pseudomonas aeruginosa* PAO1 mucA sequence. prGFF605 (SEQ ID NO: 20) and prGFF612 (SEQ ID NO: 22), which occur approximately 725 to 705 bp upstream and 997 to 978 bp downstream of mucA in *P. stutzeri*, were used to amplify the mucA sequence from *P. stutzeri* PTA-8823. The resulting PCR product was separated by agarose gel electrophoresis, gel purified, and sequenced with primers prGFF599 (SEQ ID NO: 18), prGFF600 (SEQ ID NO: 19), prGFF605 (SEQ ID NO: 20), prGFF610 (SEQ ID NO: 21), and prGFF612 (SEQ ID NO: 22).

For detecting and sequencing genes involved in biopolymer synthesis and biofilm formation in *P. alcaliphila* AL15-21 (DSM17744) and *P. toyotomiensis* HT-3 (JCM15604), primers were designed based on existing *P. alcaliphila* 34 genomic sequencing project sequences available in Genbank (GI:484034433). prGFF643 (SEQ ID NO: 23) and prGFF653 (SEQ ID NO: 33) were used to amplify sequences homologous to mucA and flanking regions from *P. alcalphila* and *P. toyotomiensis*. The resulting PCR products were treated with ExoSap-IT (USB) and sequenced with primers prGFF643-653 (SEQ ID NOs: 23-33), yielding sequence reads that yielded single DNA sequence contigs spanning the mucA gene and flanks. For the pelA-G gene cluster, eleven pairs of primers were used to amplify, or to attempt to amplify, sequences. These included prGFF662 (SEQ ID NO: 34) and prGFF663 (SEQ ID NO: 35), prGFF664 (SEQ ID NO: 36) and prGFF668 (SEQ ID NO: 38), prGFF665 (SEQ ID NO: 37) and prGFF669 (SEQ ID NO: 39), prGFF672 (SEQ ID NO:) and prGFF675 (SEQ ID NO: 43), prGFF673 (SEQ ID NO: 41) and prGFF674 (SEQ ID NO: 42), prGFF676 (SEQ ID NO: 44) and prGFF678 (SEQ ID NO: 46), prGFF676 (SEQ ID NO: 44) and prGFF680 (SEQ ID NO: 47), prGFF677 (SEQ ID NO: 45) and prGFF678 (SEQ ID NO: 46), prGFF724 (SEQ ID NO: 71) and prGFF725 (SEQ ID NO: 72), prGFF727 (SEQ ID NO: 74) and prGFF729 (SEQ ID NO: 76), and prGFF728 (SEQ ID NO: 75) and prGFF730 (SEQ ID NO: 77). Products were sequenced with primers prGFF676 (SEQ ID NO: 44), prGFF680 (SEQ ID NO: 47), prGFF677 (SEQ ID NO: 45), prGFF678 (SEQ ID NO: 46), prGFF723-728 (SEQ ID NOs: 70-75), and prGFF730 (SEQ ID NO: 77). Products were assembled into contigs that matched portions of the pelA-G gene cluster in *P. aeruginosa* PAO1.

A blast search was carried out in the *P. alcaliphila* 34 genome sequencing project sequences in Genbank using the pslA-O gene cluster from *P. aeruginosa* PAO1 as a search query. No close matches were found, suggesting that genes from that cluster are not present in the *P. alcaliphila* 34 genome. Blast searches carried out against other *Pseudomonas* genomes identified matches in *P. mendocina* ymp, *P. mendocina* DLHK, *P. pseudoalcaligenes* CECT5344, and *P. alcaligenes* MRY13. Based on these sequences, primers were designed to detect pslA-O sequences in *P. alcaliphila* AL15-21 (DSM17744) and *P. toyotomiensis* HT-3 (JCM15604). PCR amplifications were attempted from genomic DNA derived from these two strains with nine pairs of DNA primers: prGFF683 (SEQ ID NO: 50) and prGFF684 (SEQ ID NO: 51), prGFF681 (SEQ ID NO: 48) and prGFF682 (SEQ ID NO: 49), prGFF685 (SEQ ID) NO: 52) and prGFF689 (SEQ ID NO: 56), prGFF685 (SEQ ID NO: 52) and prGFF690 (SEQ ID NO: 57), prGFF686 (SEQ ID NO: 53) and prGFF689 (SEQ ID NO: 56), prGFF686 (SEQ ID NO: 53) and prGFF690 (SEQ ID NO: 57), prGFF687 (SEQ ID NO: 54) and prGFF688 (SEQ ID NO: 55), prGFF691 (SEQ ID NO: 58) and prGFF693 (SEQ ID NO: 60), and prGFF692 (SEQ ID NO: 59) and prGFF694 (SEQ ID NO: 61). Of these PCR reactions, three gave products for each strain that were sequenced. These PCR products sequences did not contain homology to the pslA-O gene cluster from *P. aeruginosa* PAO1 when searched in Genbank using BLAST. The failure to detect pslA-O homologous sequences in AL15-21 and HT-3 after several PCR and sequencing attempts suggests that these sequences are not present in these genomes. To generate a *Pseudomonas* strain with a defect in biofilm formation, but with enhanced cell-free soluble polymer production, knockout constructs were generated for *P. alcaliphila* AL15-21 (DSM17744), *P. toyotomiensis* HT-3 (JCM15604), and *P. stutzeri* PTA-8823 that implement an unmarked deletion strategy (as described in Colvin above). A markerless mucA knockout construct was generated for *P. stutzeri* PTA-8823 by assembly of upstream and downstream sequences, synthesized in a single fragment of DNA, partGFF27 (SEQ ID NO: 1), into SmaI cut pEX100T. A markerless mucA knockout construct was generated for *P. alcaliphila* AL15-21 (DSM17744) by assembly of upstream and downstream sequences, synthesized as two overlapping fragments of DNA, partGFF30 (SEQ ID NO: 4) and partGFF31 (SEQ ID NO: 5) respectively, into SmaI cut pEX100T. A markerless mucA knockout construct was generated for *P. toyotomiensis* HT-3 (JCM15604) by assembly of upstream and downstream sequences, synthesized as two overlapping fragments of DNA, partGFF32 (SEQ ID NO: 6) and partGFF33 (SEQ ID NO: 7) respectively, into SmaI cut pEX100T. For each assembly, the one or two fragments were combined with SmaI cut pEX100T in an isothermal assembly reaction using Gibson Assembly Master mix (New England Biolabs), at 50° C. for 1 hour, according to the manufacturer's instructions. Assembly of the correct sequences into the plasmid vector were verified for each of these constructs; plasmid pGFF167 was isolated containing the ΔmucA markerless knockout construct for *P. stutzeri* generated from partGFF27 (SEQ ID NO: 1). Plasmid pGFF170 was isolated containing the ΔmucA markerless knockout construct for *P. alcaliphila* generated from partGFF30 (SEQ ID NO: 4) and partGFF31 (SEQ ID NO: 5). Plasmid pGFF171 was isolated containing the ΔmucA markerless knockout construct for *P. toyotomiensis* generated from partGFF32 (SEQ ID NO: 6) and partGFF33 (SEQ ID NO: 7). pGFF167 will be transformed into *P. stutzeri* PTA-8823 by electroporation or conjugal transfer from *E. coli*, and single recombination integrants will be selected on LB plates containing 300 μg/ml carbenicillin (and 25 μg/ml irgasan in cases of conjugal transfer). pGFF171 will be transformed into *P. toyotomiensis* HT-3 (JCM15604) by electroporation or conjugal transfer from *E. coli*, and single recombination integrants will be selected on LB plates containing 300 μg/ml carbenicillin (and 25 μg/ml irgasan in cases of conjugal transfer). Double recombination mutants will be selected on LB plates containing 10% sucrose. ΔmucA knockout strains will be generated for *P. stutzeri* PTA-8823 and *P. toyotomiensis* HT-3 by this approach.

Plasmid pGFF170 was introduced into *P. alcaliphila* AL15-21 (DSM17744) by triparental mating of *P. alcaliphila* with dH5alpha *E. coli* containing plasmid pRK2013 and dH5alpha *E. coli* containing plasmid pGFF70. Isolates was selected on a minimal salts medium VBMM containing 500 μg/ml carbenicillin. Isolates were then passaged in the absence of selection and plated onto LB plate medium containing 10% sucrose. Isolates from the sucrose plate that were no long carbenicillin resistant were tested for the markerless knockout by using primers prGFF643 (SEQ ID NO: 23) and prGFF653 (SEQ ID NO: 33), which were external to the construct, upstream and in the *P. alcaliphila* genome in a PCR. Isolates were also tested with primers prGFF645 (SEQ ID NO: 25) and prGFF651 (SEQ ID NO: 31), occurring 163 nt upstream and 172 nt downstream of the mucA ORF. One isolate, GFF419, contained a single PCR product for both primer pairs of a size that indicated that the mucA ORF had been removed from the *P. alcaliphila* genome. The PCR product amplified by prGFF643 (SEQ ID NO: 23) and prGFF653 (SEQ ID NO: 33) was sequenced, and verified the removal of the mucA ORF at the appropriate sequence in GFF419. Sequencing of a PCR product generated with 16S rDNA PCR primers prGFF123 (SEQ ID NO: 8) and 124 (SEQ ID NO: 9) verified that GFF419 is identical to *P. alcaliphila* AL15-21 (DSM17744) at that locus.

Defects in the mucA gene in *P. aeruginosa* PAO1 result in an overproduction of the soluble exopolysaccharide alginate (Mathee, K., et al. Microbiology 1999 June: 145 (pt6): 1349-57) and a decrease in some biofilm characteristics including surface attachment (Hay, I. D., et al. Appl Environ Microbiol. 2009 September; 75(18): 6022 6025). To test for overproduction of soluble polymer in the ΔmucA strain in *P. alcaliphila*, GFF419, saturated overnight cultures (approx. OD600 3.0) for the wildtype *P. alcaliphila* AL15-21 parent strain and GFF419 were diluted to the equivalent OD600 of 0.01 in 30 mls Luria Broth (LB)+5% glucose in 250 ml shake flasks. 0.03 Units of Neutrase (Sigma) were added to the medium to prevent the action of potential alginate degrading enzymes, such as alginate lyase, in the cultures. Cultures were grown for four days at 32° C. with shaking. 10 ml of each culture was withdrawn and the viscosities measured using an Ostwald (U-tube) viscometer (Table 3). The viscosity of the culture from the wildtype culture (1.18 centipoise) was measured to be similar to that of water (1.00 centipoise). By contrast, the ΔmucA strain, GFF419, culture was clearly viscous, with a measurement of 7.55 centipoise. Subsequently, 25 mls of each culture was centrifuged at 6000 g for 15 min. The supernatant was removed, and both the supernatant and the cell pellet saved. 25 ml isopropanol was added to the culture supernatant and mixed. The mixture was then placed at -20° C. for 3 days. The cell pellet was washed in 1 ml LB medium and centrifuged, and the cell pellet was stored at -80° C. The supernatant was spun at 6000 g for 15 min and the supernatant was removed. The precipitated pellet was washed in 0.5 ml 70% ethanol and centrifuged. The supernatant was removed from the precipitate. As a control, a 25 ml sample of LB+5% medium was also carried through the precipitation regime. The control, supernatant precipitates and the cell pellets were placed in a lyophilizer overnight and were dried completely. The samples were weighed. The supernatant from the wildtype *P. alcaliphila* culture gave a small pellet (7 mg), which was only slightly larger than the control from medium alone. The supernatant from the ΔmucA *P. alcaliphila* isolate, GFF419, yielded a markedly larger pellet (34 mg) (Table 1). The higher viscosity of the GFF419 culture and the higher amount of isopropanol precipitate from the culture supernatant, versus the wild type strain, indicates production of viscous soluble polymer.

*P. aeruginosa* PAO1 strains in which the mucA gene is defective exhibit defects in the formation of biofilms. To test a mucA disruption for a similar defect in *P. alcaliphila*, wildtype *P. alcaliphila* AL15-21 (DSM17744) and GFF419 were inoculated from saturated overnight cultures at 1/200× concentration in 5 mls YC-Alk10 medium (per liter: MgSO4.7H2O, 0.2 g; NaCl, 25 g; KCl, 1 g; KH2PO4, 1 g; NH4Cl, 1 g; Na glutamate, 1 g; Yeast extract, 5 g; Casamino acids (Oxoid), 5 g; Na2CO3, 5 g; FeCl2.4H2O, 36 mg; MnCl2.4H2O, 0.36 mg; adjusted to pH10 with NaOH) supplemented with 5% glucose and grown 5 days at 32° C. in a six well plate without shaking. Both of the AL15-21 and GFF419 cultures grew and became turbid. However, whereas the wild type strain exhibited significant formation of typical biofilms within the culture no biofilms were observed for the GFF419 ΔmucA strain.

Based on the conservation of biofilm biosynthesis and regulatory genes, gene knockouts of mucA and psl gene homologs in *P. stutzeri* likely impact biofilm architecture in a similar manner. The conservation of sequence between the *P. stutzeri* genomes allow PCR primers to be designed to generate targeted gene knockout constructs. Knockouts will be generated using an unmarked deletion strategy (as described in Colvin above). Flanking regions of each gene targeted for deletion will be PCR amplified from *P. stutzeri* ATCC PTA-8823 genomic DNA and ligated into the suicide vector pEX18Gm. Plasmid inserts will be verified by sequencing. Plasmids will be transformed into *P. stutzeri* ATCC PTA-8823 by electroporation or conjugal transfer from *E. coli*, and single recombination integrants will be selected on LB containing 100 μg/ml gentamycin (and 25 μg/ml irgasan in cases of conjugal transfer). Double recombination mutants will be selected on LB plates containing 10% sucrose. By this approach, ΔmucA and ΔmucAΔpslA strains will be constructed such that the gene deletions will remove the first to last nucleotides of the mucA and pslA ORFs.

Example 7

Transfer of Xanthan Gum Biosynthesis Gene Cluster into *Pseudomonas* Strains

Xanthan gum is a soluble acidic heteropolysaccharide produced by *Xanthomonas* species (typically *Xanthomonas campestris*) that has a high molecular weight, ranging from 500 to 2000 kDa. Xanthan gum is produced for a wide range of commercial applications by industrial fermentation, and the genetics underlying its biosynthesis has been described. Xanthan gum production is directed by a cluster of at least twelve genes coding for assembly, acetylation, pyruvylation, polymerization, and secretion. These genes consist of gumBCDEFGHIJKLM, and may include the gumA and gumN genes at either end of the gene cluster, though it appears that they do not function in Xanthan gum synthesis (Pollock T. J., et al. J. of Ind. Microbiology and Biotechnology (1997) 19, 92-97. Moreover, these genes appear to be controlled by a single promoter (Katzen, F., et al., J. of Bacteriology, July 1996 vol. 178 No. 14 p 4313-18). The gum gene cluster (including gumBCDEFGHIJKLM) has previously been cloned into a plasmid and transferred into a *Sphingomonas* strain, from which production of Xanthan gum production was subsequently detected (Pollock above).

The Xanthan gumBCDEFGHIJKLM cluster was PCR amplified from *Xanthomonas campestris* DSM 19000 genomic DNA using rTth DNA polymerase (Life Technologies) to generate a PCR product corresponding to nucleotides 11 to 16054 in Genbank sequence U22511 (*Xanthomonas* B1459 gum cluster) flanked by homologous sequence at the cloning site in pBBR1MCS. The primers used for amplification of the gum gene cluster included (prGFF533) gaattcctgcagcccaaatGAGGCGGTAACAGGGGAT (SEQ ID NO: 10) and (prGFF534) gcggtggcggccgctctagaCCTT-GCTGACCTTCCACAG (SEQ ID NO: 11) and contained the SwaI half site and a full XbaI site. pBBR1MCS was cut with XbaI and SmaI and purified. The cut vector was assembled with the gum gone cluster DNA fragment by isothermal assembly using the Gibson Assembly Master Mix (New England Biolabs). The assembly product was transformed into DH10-beta competent *E. coli* cells and selected on LB medium containing chloramphenicol. Individual clone isolates were selected, screened by PCR for assembly, and shotgun sequenced. The sequencing reads were assembled into a single contig, and the resulting assembled sequence verified the fidelity of the gum gene cluster insert. Plasmid pGFF155, a successful DNA clone containing the gum gene cluster, was transformed into *Pseudomonas alcaliphila* AL15-21 (DSM17744) and *P. toyotomiensis* HT-3 (JCM15604) by electroporation and selected on medium containing 200 and 400 µg/ml chloramphenicol, respectively. Presence of pGFF155 in *P. alcaliphila* and *P. toyotomiensis* was verified by PCR, and the *P. alcaliphila* and *P. toyotomiensis* transformant isolates were named GFF375 and GFF377 respectively.

GFF257 is an isolate of *P. toyotomiensis* HT-3 transformed with the original pHBR1MCS vector by electroporation. Strains GFF257 and GFF377 were grown overnight at 28° C. in 10 mls MhYC-alk medium (Per liter: $MgSO_4 \cdot 7H_2O$, 0.2 g; NaCl, 25 g; KCl, 1 g; $KH_2PO_4$, 1 g; $NH_4Cl$, 1 g; Na glutamate, 1 g; Yeast extract, 5 g; Casamino acids (Oxoid), 5 g; $FeCl_2 \cdot 4H_2O$, 36 mg; $MnCl_2 \cdot 4H_2O$, 0.36 mg; $Na_2CO_3$ added to pH7.0) containing 400 µg/ml chloramphenicol. Saturated overnight cultures were diluted 200-fold into 1000 mls Pmn medium (Per liter: glucose, 50 g; $(NH_4)_2HPO_4$, 1.25 g; $K_2PO_4$, 1.25 g; $CaCl_2 \cdot 2H_2O$, 0.1 g; $MgSO_4 \cdot 7H_2O$, 0.4 g; Citric acid, 0.99 g; Yeast extract (Oxoid), 0.2 g; $MnSO_4 \cdot 4H_2O$, 1.1 mg; $ZnSO_4 \cdot 7H_2O$, 0.2 mg; $CoSO_4 \cdot 7H_2O$, 0.28 mg; $CuSO_4 \cdot 5H_2O$, 0.25 mg; $H_3BO_3$, 0.06 mg; $FeSO_4 \cdot 7H_2O$, 3.6 mg; pH 7.0) containing 300 µg/ml chloramphenicol, and grown in 2.8 L flasks at 28° C. for 7 days. Pmn medium is a nitrogen limiting medium based on a medium described to grow a *Pseudomonas mendocina* strain for alginate production (Anderson, A. J., et al. Journal of General Microbiology. 1987. 133: 1045-1052). 900 mls of each culture was centrifuged (30 min, 5000 RPM). Supernatant was taken and an equal volume (900 mls) 100% ethanol was added to each supernatant, to precipitate soluble polymer. The mixtures were place at −20° C. overnight. The mixtures were centrifuged (30 min, 5000 RPM) and washed twice in 70% ethanol. The liquid was removed and the pellets allowed to air dry overnight. The precipitated and dried pellets were weighed. The GFF257 pellet weighed 0.0 g and the GFF377 pellet weighed 0.9 g. Each pellet was resuspended in 25 mls water. The viscosities were measured with an Uberholde viscometer (TABLE 4). Results indicated the presence of viscous polymer, which could be isolated by precipitation, in the culture medium in the *P. toyotomiensis* strain containing the Xanthan gene cluster.

Plasmid pGFF155 will also be transformed into wildtype *P. aeruginosa* PAO1 and into the *P. aeruginosa* PAO1 ΔpslBCDΔpelA biofilm deficient strain by electroporation and *Pseudomonas* transformants will be selected on LB medium containing chloramphenicol. Uptake of the vector and gum gene cluster in the *P. aeruginosa* PAO1 strains will be verified by PCR.

Example 8

Construction of Biofilm Deficient *Bacillus* Strains

Biofilms in *Bacillus subtilis* are complex structures that have been studied extensively and may consist of several components such as structural neutral polymers (levan and exopolysaccharides generated by the eps operon), charged polymers (poly-gamma-glutamic acid), amphiphilic molecules (surfactin), active EPS enzymes, and the amyloid fiber-forming TasA protein (reviewed in Marvasi, M., et al., 2010 FEMS Microbiology letter, 313:1-9).

The biofilm-forming *B. subtilis* strain NCIB3610 forms biofilms on the surface of solid agar medium plates and robust floating biofilms (termed pellicles) on standing cultures at the air-liquid interlace. The biofilm structure is dependent on the extracellular matrix, formed largely by exopolysaccharide and the TasA protein (Branda, S. S., et al, Mol Microbiol. 2006 February; 59(4):1229-38). The TasA protein is 261 amino acids in length and polymerizes to form amyloid fibers that have been shown to be essential for the structural integrity of the extracellular matrix in biofilms and which are resistant to breakdown (Chu, F. et al., Mol Microbiol. 2006 February; 59(4):1216-28, Romero, D., et al., Proc Natl Acad Sci USA. 2010 February 2; 107(5): 2230 2234). Strains with defects in the tasA gene fail to form bundles of cells typical in biofilm pellicles, form less extracellular material in biofilms, and form biofilms that are thinner and weaker (Branda 2006, Dogsa, I, et al. PLoS One. 2013; 8(4): e62044. Published online 2013 Apr. 26. doi: 10.1371/journal.pone.0062044).

To generate a *Bacillus* strain deficient in biofilm formation, a ΔtasA::cat PCR construct was generated for *B. subtilis* strain NCIB3610 in two PCR steps by the long-flanking homology PCR (LFH-PCR) technique (Kim and Kim, Biotechnol Bioprocess Eng 2000 Kim, J and Kim, B, Biotechnol. Bioprocess Eng. 2000 5(5): 327-331.). The 1200 bp sequences immediately upstream and downstream of the tasA ORF were PCR amplified from NCIB3610 genomic DNA using primer pairs prGFF556 (SEQ ID NO: 12) and prGFF557 (SEQ ID NO: 13) and prGFF558 (SEQ ID NO: 14) and prGFF559 (SEQ ID NO: 15), respectively. The cat gene, conferring chloramphenicol resistance, was PCR amplified from pNW33n (BGSC ECE136) using primers prGFF560 (SEQ ID NO: 16) and prGFF561 (SEQ ID NO: 17), which contain sequences at the 5' ends that match the 35 bp immediately upstream and 35 bp immediately downstream of the tasA ORF, respectively. The three PCR products were combined in a subsequent PCR reaction with primers prGFF556 (SEQ ID NO: 12) and prGFF559 (SEQ ID NO: 15). The product of the second PCR step was resolved on a 1% agarose gel, and a product of 2257 bp was detected and purified from the gel. This product will be introduced into B. subtilis strain NCIB3610 directly (Kim, J and Kim, B, Biotechnol. Bioprocess Eng. 2000 5(5): 327-331), which will result in a deletion of the tasA ORF from the first nucleotide to the last.

A homolog of the Bacillus subtilis 168 tasA gene was identified in the genome sequenced Bacillus mojavensis strain RO-H-1; the corresponding protein (GI:498020761) shares 98% sequence identity with Bacillus subtilis 168 tasA at the amino acid level. Bacillus mojavensis JF2 (ATCC 39307) is a well-studied strain isolated from an oil field that has been described and tested as an effective strain for MEOR applications. The tasA gene will be deleted in Bacillus mojavensis JF2 by the pMAD markerless knockout system (Arnaud, M. et al., Appl Environ Microbiol. 2004 November 70 (11) 6887-, as described in Durand, S et al., PLoS Genetics 8(12): e1003181. doi: 10.1371/journal.pgen.1003181. Epub 2012 Dec. 27)

500 nt sequences upstream and downstream of the tasA gene will be PCR amplified with overlapping oligonucleotides from B. mojavensis JF2. The two flanking sequences will be assembled in a subsequent PCR reaction to generate a 1000 nt PCR product containing a deletion of the tasA ORF. The assembled product will subsequently be digested and ligated into pMAD. The integrative plasmid will then be transformed into Bacillus mojavensis JF2 by electroporation, by a method previously described for several B. mojavensis strains (Olubajo, B and Bacon, C. J Microbiol Methods. 2008 August; 74(2-3):102-105).

TABLE 1 algU, mucA, mucB, mucC, and mucD (*P. aeruginosa* PAO1) BLASTP match results in *P. stutzeri* protein sequences in Genbank (E-value <1e −40)

| Definition | % identity | % positives | evalue | bit score |
|---|---|---|---|---|
| # Query: gi|15595959|ref|NP_249453.1| RNA polymerase sigma factor AlgU [*Pseudomonas aeruginosa* PAO1] | | | | |
| >gi|518172025|ref|WP_019342233.1| RNA polymerase sigma factor AlgU [*Pseudomonas stutzeri*] | 93.26 | 97.41 | 3.00E−132 | 373 |
| >gi|387969827|gb|EIK54107.1| RNA polymerase sigma factor AlgU [*Pseudomonas stutzeri* TS44] | 92.75 | 97.41 | 2.00E−131 | 371 |
| >gi|397686068|ref|YP_006523387.1| RNA polymerase sigma factor AlgU [*Pseudomonas stutzeri* DSM 10701] | 92.23 | 97.41 | 3.00E−131 | 370 |
| >gi|146281607|ref|YP_001171760.1| RNA polymerase sigma factor AlgU [*Pseudomonas stutzeri* A1501] | 91.71 | 97.41 | 8.00E−131 | 369 |
| # Query: gi|15595960|ref|NP_249454.1| anti-sigma factor MucA [*Pseudomonas aeruginosa* PAO1] | | | | |
| >gi|431928191|ref|YP_007241225.1| negative regulator of sigma E activity [*Pseudomonas stutzeri* RCH2] | 68.53 | 81.22 | 2.00E−73 | 223 |
| >gi|452006822|gb|EMD99087.1| anti-sigma factor MucA [*Pseudomonas stutzeri* NF13] | 67.51 | 81.22 | 3.00E−73 | 223 |
| >gi|392420216|ref|YP_006456820.1| anti-sigma factor MucA [*Pseudomonas stutzeri* CCUG 29243] | 67.51 | 81.22 | 2.00E−71 | 219 |
| >gi|409781090|gb|EKN60694.1| anti-sigma factor MucA [*Pseudomonas stutzeri* KOS6] | 65.48 | 79.19 | 7.00E−69 | 212 |
| >gi|379064449|gb|EHY77192.1| anti-sigma factor MucA [*Pseudomonas stutzeri* ATCC 14405 = CCUG 16156] | 67.01 | 80.71 | 1.00E−65 | 204 |
| >gi|397686069|ref|YP_006523388.1| anti-sigma factor MucA [*Pseudomonas stutzeri* DSM 10701] | 65.5 | 77 | 1.00E−65 | 204 |
| >gi|146281608|ref|YP_001171761.1| anti-sigma factor MucA [*Pseudomonas stutzeri* A1501] | 68.18 | 80.3 | 2.00E−64 | 201 |
| >gi|386019815|ref|YP_005937839.1| anti-sigma factor MucA [*Pseudomonas stutzeri* DSM 4166] | 68.18 | 80.3 | 3.00E−64 | 200 |
| >gi|518172026|ref|WP_019342234.1| sigma factor AlgU negative regulatory protein [*Pseudomonas stutzeri*] | 66.5 | 79.5 | 2.00E−63 | 198 |
| >gi|339493209|ref|YP_004713502.1| anti-sigma factor MucA [*Pseudomonas stutzeri* ATCC 17588 = LMG 11199] | 67.17 | 79.29 | 5.00E−62 | 194 |
| >gi|387969826|gb|EIK54106.1| anti-sigma factor MucA [*Pseudomonas stutzeri* TS44] | 67.17 | 79.8 | 6.00E−57 | 181 |
| # Query: gi|15595961|ref|NP_249455.1| negative regulator for alginate biosynthesis MucB [*Pseudomonas aeruginosa* PAO1] | | | | |
| >gi|392420217|ref|YP_006456821.1| sigma E regulatory protein MucB/RseB [*Pseudomonas stutzeri* CCUG 29243] | 60.19 | 76.05 | 3.00E−129 | 375 |
| >gi|431928190|ref|YP_007241224.1| negative regulator of sigma E activity [*Pseudomonas stutzeri* RCH2] | 60.52 | 75.08 | 1.00E−128 | 374 |
| >gi|146281609|ref|YP_001171762.1| negative regulator for alginate biosynthesis MucB [*Pseudomonas stutzeri* A1501] | 59.03 | 75.16 | 3.00E−125 | 365 |

TABLE 1-continued algU, mucA, mucB, mucC, and mucD (*P. aeruginosa* PAO1) BLASTP match results in *P. stutzeri* protein sequences in Genbank (E-value <1e⁻40)

| Definition | % identity | % positives | evalue | bit score |
|---|---|---|---|---|
| >gi\|386019816\|ref\|YP_005937840.1\| negative regulator for alginate biosynthesis MucB [*Pseudomonas stutzeri* DSM 4166] | 59.03 | 75.16 | 3.00E−125 | 365 |
| >gi\|518237074\|ref\|WP_019407282.1\| sigma factor AlgU regulatory protein MucB [*Pseudomonas stutzeri*] | 58.71 | 74.84 | 3.00E−124 | 362 |
| >gi\|515814934\|ref\|WP_017245687.1\| sigma factor AlgU regulatory protein MucB [*Pseudomonas stutzeri*] | 58.71 | 74.84 | 3.00E−124 | 362 |
| >gi\|339493210\|ref\|YP_004713503.1\| negative regulator for alginate biosynthesis MucB [*Pseudomonas stutzeri* ATCC 17588 = LMG 11199] | 58.39 | 74.19 | 3.00E−123 | 360 |
| >gi\|409781089\|gb\|EKN60693.1\| sigma E regulatory protein MucB/RseB [*Pseudomonas stutzeri* KOS6] | 57.28 | 73.14 | 2.00E−122 | 358 |
| >gi\|379064450\|gb\|EHY77193.1\| sigma E regulatory protein, MucB/RseB [*Pseudomonas stutzeri* ATCC 14405 = CCUG 16156] | 61.35 | 76.24 | 7.00E−121 | 353 |
| >gi\|516319045\|gb\|EPL59790.1\| sigma E regulatory protein MucB/RseB [*Pseudomonas stutzeri* B1SMN1] | 60.78 | 76.33 | 2.00E−118 | 347 |
| >gi\|518172027\|ref\|WP_019342235.1\| sigma factor AlgU regulatory protein MucB [*Pseudomonas stutzeri*] | 57.56 | 72.99 | 2.00E−116 | 342 |
| >gi\|397686070\|ref\|YP_006523389.1\| sigma E regulatory protein MucB/RseB [*Pseudomonas stutzeri* DSM 10701] | 59.09 | 70.98 | 7.00E−114 | 335 |
| >gi\|387969825\|gb\|EIK54105.1\| sigma E regulatory protein MucB/RseB [*Pseudomonas stutzeri* TS44] | 58.16 | 73.05 | 6.00E−112 | 330 |
| >gi\|452006824\|gb\|EMD99089.1\| sigma E regulatory protein MucB/RseB [*Pseudomonas stutzeri* NFis] | 62.15 | 74.77 | 4.00E−89 | 269 |
| # Query: gi\|15595962\|ref\|NP_249456.1\| positive regulator for alginate biosynthesis MucC [*Pseudomonas aeruginosa* PAO1] | | | | |
| >gi\|387969824\|gb\|EIK54104.1\| positive regulator for alginate biosynthesis MucC [*Pseudomonas stutzeri* TS44] | 61.64 | 75.34 | 5.00E−56 | 176 |
| >gi\|379064451\|gb\|EHY77194.1\| positive regulator for alginate biosynthesis MucC [*Pseudomonas stutzeri* ATCC 14405 = CCUG 16156] | 57.43 | 73.65 | 5.00E−54 | 171 |
| >gi\|409781088\|gb\|EKN60692.1\| positive regulator for alginate biosynthesis MucC [*Pseudomonas stutzeri* KOS6] | 57.72 | 72.48 | 2.00E−53 | 169 |
| >gi\|452006825\|gb\|EMD99090.1\| positive regulator for alginate biosynthesis MucC [*Pseudomonas stutzeri* NF13] | 57.43 | 71.62 | 7.00E−53 | 168 |
| >gi\|392420218\|ref\|YP_006456822.1\| positive regulator for alginate biosynthesis MucC [*Pseudomonas stutzeri* CCUG 29243] | 58.11 | 72.3 | 1.00E−50 | 162 |
| >gi\|397686071\|ref\|YP_006523390.1\| positive regulator for alginate biosynthesis MucC [*Pseudomonas stutzeri* DSM 10701] | 63.51 | 77.7 | 3.00E−49 | 158 |
| >gi\|431928189\|ref\|YP_007241223.1\| Positive regulator of sigma E activity [*Pseudomonas stutzeri* RCH2] | 56.76 | 70.95 | 4.00E−49 | 158 |
| >gi\|146281610\|ref\|YP_001171763.1\| positive regulator for alginate biosynthesis MucC [*Pseudomonas stutzeri* A1501] | 58.78 | 71.62 | 1.00E−44 | 147 |
| >gi\|339493211\|ref\|YP_004713504.1\| positive regulator for alginate biosynthesis MucC [*Pseudomonas stutzeri* ATCC 17588 = LMG 11199] | 58.78 | 71.62 | 1.00E−44 | 147 |
| >gi\|518172028\|ref\|WP_019342236.1\| positive regulator for alginate biosynthesis MucC [*Pseudomonas stutzeri*] | 51.03 | 66.9 | 2.00E−41 | 138 |
| # Query: gi\|15595963\|ref\|NP_249457.1\| serine protease MucD [*Pseudomonas aeruginosa* PAO1] | | | | |
| >gi\|387969823\|gb\|EIK54103.1\| serine protease MucD [*Pseudomonas stutzeri* TS44] | 73.84 | 86.5 | 0 | 699 |
| >gi\|409781087\|gb\|EKN60691.1\| serine protease MucD [*Pseudomonas stutzeri* KOS6] | 73.05 | 85.47 | 0 | 695 |
| >gi\|452006826\|gb\|EMD99091.1\| serine protease MucD [*Pseudomonas stutzeri* NF13] | 72.84 | 85.05 | 0 | 692 |
| >gi\|379064452\|gb\|EHY77195.1\| serine protease MucD [*Pseudomonas stutzeri* ATCC 14405 = CCUG 16156] | 72 | 84.21 | 0 | 691 |
| >gi\|392420219\|ref\|YP_006456823.1\| serine protease MucD [*Pseudomonas stutzeri* CCUG 29243] | 72.84 | 84.63 | 0 | 690 |
| >gi\|431928188\|ref\|YP_007241222.1\| periplasmic serine protease, Do/DeqQ family [*Pseudomonas stutzeri* RCH2] | 72.63 | 85.05 | 0 | 688 |
| >gi\|146281611\|ref\|YP_001171764.1\| serine protease MucD [*Pseudomonas stutzeri* A1501] | 71.91 | 85.12 | 0 | 682 |
| >gi\|397686072\|ref\|YP_006523391.1\| serine protease MucD [*Pseudomonas stutzeri* DSM 10701] | 72.36 | 85.23 | 0 | 681 |
| >gi\|339493212\|ref\|YP_004713505.1\| serine protease MucD [*Pseudomonas stutzeri* ATCC 17588 = LMG 11199] | 71.49 | 84.7 | 0 | 676 |

TABLE 1-continued algU, mucA, mucB, mucC, and mucD (*P. aeruginosa* PAO1) BLASTP match results in *P. stutzeri* protein sequences in Genbank (E-value <1e$^{-40}$)

| Definition | % identity | % positives | evalue | bit score |
|---|---|---|---|---|
| >gi\|518169326\|ref\|WP_019339534.1\| serine peptidase [*Pseudomonas stutzeri*] | 71.34 | 85.99 | 0 | 674 |
| >gi\|387969988\|gb\|EIK54268.1\| HtrA-like protease AlgW [*Pseudomonas stutzeri* TS44] | 46.13 | 67.68 | 4.00E−83 | 265 |
| >gi\|409782192\|gb\|EKN61759.1\| HtrA-like protease AlgW [*Pseudomonas stutzeri* KOS6] | 43.11 | 64.07 | 8.00E−83 | 262 |
| >gi\|338800400\|gb\|AEJ04232.1\| HtrA-like protease AlgW [*Pseudomonas stutzeri* ATCC 17588 = LMG 11199] | 46.13 | 68.35 | 2.00E−82 | 263 |
| >gi\|431928383\|ref\|YP_007241417.1\| trypsin-like serine protease with C-terminal PDZ domain [*Pseudomonas stutzeri* RCH2] | 46.26 | 68.37 | 3.00E−82 | 263 |
| >gi\|452006561\|gb\|EMD98833.1\| HtrA-like protease AlgW [*Pseudomonas stutzeri* NF13] | 45.79 | 68.01 | 1.00E−81 | 261 |
| >gi\|392422348\|ref\|YP_006458952.1\| HtrA-like protease AlgW [*Pseudomonas stutzeri* CCUG 29243] | 45.79 | 68.01 | 1.00E−81 | 261 |
| >gi\|397685896\|ref\|YP_006523215.1\| HtrA-like protease AlgW [*Pseudomonas stutzeri* DSM 10701] | 42.99 | 64.48 | 2.00E−81 | 260 |
| >gi\|409779972\|gb\|EKN59617.1\| HtrA-like protease AlgW [*Pseudomonas stutzeri* KOS6] | 45.79 | 67.34 | 3.00E−81 | 260 |
| >gi\|379063956\|gb\|EHY76699.1\| HtrA-like protease AlgW [*Pseudomonas stutzeri* ATCC 14405 = CCUG 16156] | 45.45 | 68.01 | 7.00E−81 | 259 |
| >gi\|518172423\|ref\|WP_019342631.1\| 2-alkenal reductase [*Pseudomonas stutzeri*] | 45.45 | 67.34 | 2.00E−80 | 259 |
| >gi\|516323248\|gb\|EPL63964.1\| 2-alkenal reductase [*Pseudomonas stutzeri* B1SMN1] | 38.56 | 55.88 | 3.00E−53 | 186 |
| >gi\|339496248\|ref\|YP_004716541.1\| hypothetical protein PSTAB_4171 [*Pseudomonas stutzeri* ATCC 17588 = LMG 11199] | 37.5 | 55.59 | 3.00E−50 | 178 |
| >gi\|386021023\|ref\|YP_005939047.1\| hypothetical protein PSTAA_2421 [*Pseudomonas stutzeri* DSM 4166] | 37.5 | 55.59 | 5.00E−50 | 177 |

TABLE 2 pslA (*P. aeruginosa* PAO1) BLASTP match results in *P. stutzeri* protein sequences in Genbank (E-value <1e$^{-40}$)

| | Definition | | | |
|---|---|---|---|---|
| # Query: gi\|15597427\|ref\|NP_250921.1\| protein PslA [*Pseudomonas aeruginosa* PAO1] | % identity | % positives | evalue | bit score |
| >gi\|387967350\|gb\|EIK51654.1\| capsular polysaccharide biosynthesis protein [*Pseudomonas stutzeri* TS44] | 65.69 | 81.17 | 0 | 653 |
| >gi\|452008339\|gb\|EME00580.1\| capsular polysaccharide biosynthesis protein [*Pseudomonas stutzeri* NF13] | 65.48 | 80.54 | 0 | 649 |
| >gi\|516320548\|gb\|EPL61274.1\| capsular polysaccharide biosynthesis protein [*Pseudomonas stutzeri* B1SMN1] | 64.85 | 80.54 | 0 | 649 |
| >gi\|392421696\|ref\|YP_006458300.1\| capsular polysaccharide biosynthesis protein [*Pseudomonas stutzeri* CCUG 29243] | 65.06 | 80.54 | 0 | 648 |
| >gi\|339494468\|ref\|YP_004714761.1\| capsular polysaccharide biosynthesis protein [*Pseudomonas stutzeri* ATCC 17588 = LMG 11199] | 64.85 | 80.54 | 0 | 648 |
| >gi\|146282832\|ref\|YP_001172985.1\| capsular polysaccharide biosynthesis protein [*Pseudomonas stutzeri* A1501] | 64.85 | 80.33 | 0 | 646 |
| >gi\|386021197\|ref\|YP_005939221.1\| capsular polysaccharide biosynthesis protein [*Pseudomonas stutzeri* DSM 4166] | 64.64 | 80.54 | 0 | 646 |
| >gi\|431926982\|ref\|YP_007240016.1\| undecaprenyl-phosphate glucose phosphotransferase [*Pseudomonas stutzeri* RCH2] | 64.23 | 79.29 | 0 | 642 |
| >gi\|379063599\|gb\|EHY76342.1\| capsular polysaccharide biosynthesis protein [*Pseudomonas stutzeri* ATCC 14405 = CCUG 16156] | 63.18 | 79.5 | 0 | 639 |
| >gi\|395808331\|gb\|AFN77736.1\| capsular polysaccharide biosynthesis protein [*Pseudomonas stutzeri* DSM 10701] | 64.09 | 80.79 | 0 | 619 |
| >gi\|409780607\|gb\|EKN60234.1\| capsular polysaccharide biosynthesis protein [*Pseudomonas stutzeri* KOS6] | 65.9 | 80.75 | 0 | 616 |
| >gi\|518171415\|ref\|WP_019341623.1\| capsular polysaccharide biosynthesis protein [*Pseudomonas stutzeri*] | 63.6 | 80.75 | 0 | 614 |

TABLE 2-continued pslA (P. aeruginosa PAO1) BLASTP match results in P. stutzeri protein sequences in Genbank (E-value <1e^−40)

| | Definition | | | |
|---|---|---|---|---|
| # Query: gi|15597427|ref|NP_250921.1| protein PslA [*Pseudomonas aeruginosa* PAO1] | % identity | % positives | evalue | bit score |
| >gi|516319785|gb|EPL60518.1| sugar transferase [*Pseudomonas stutzeri* B1SMN1] | 42.68 | 62.5 | 2.00E−78 | 256 |

TABLE 3

Wildtype *P. alcaliphila* AL15-21 (DSM17744) and GFF419 (ΔmucA) viscosity measurements and soluble polymer detection after 4 days' growth.

| Strain | Medium | time (sec) | Viscosity (cP) | Cell pellet DCW (mg) | Supernatant Precipitate (mg) |
|---|---|---|---|---|---|
| — | H2O | 11 | 1.00 | | |
| — | LB + 5% glucose | | | 0 | 5 |
| AL15-21 (wildtype) | LB + 5% glucose | 13 | 1.18 | 95 | 7 |
| GFF419 (ΔmucA) | LB + 5% glucose | 83 | 7.55 | 68 | 34 |

TABLE 4

Isolation and viscosity testing of soluble polymer produced by *P. toyotomiensis* with an empty vector (GFF257) and with a vector containing the Xanthan gum cluster (GFF377).

| Strain | Medium | time (sec) | Viscosity (cP) | Supernatant Precipitate (g) |
|---|---|---|---|---|
| — | H2O | 12 | 1.00 | |
| GFF257 (pBBR1MCS) | Pmn | 12 | 1.00 | 0 |
| GFF377 (pGFF155) | Pmn | 697 | 58.08 | 0.9 |

TABLE 5

Synthesized DNA sequences

| Sequence name | Sequence | Notes | Length | SEQ ID NO: |
|---|---|---|---|---|
| partGFF27 | CCTGTTATCCCTACCCcatctggtggcgcgc ggcagacgcccgccggatagtgatgtgagtt ccgaggacgccgagttttatgagggcgatca cgctctcaaggacatcgagtcaccggaacgc tcgctgctcagggatgagattgaagataccg ttcatcgaaccattcaacttttgccagaaga tttgcgtacggctctaacactgcgtgaattt gatggtcttagttatgaagacattgcgagcg tcatgcagtgtccggtgggcacagtgcgttc ccggatatccgggcacgtgaagccatagata aagcattgcaaccccttgttgcatgaatcctg agacagcggcgacagccaagagaggaaccgc cGGAGAAACATGCGCGTATTACCGCTGTATG TGGTGATGGGGCTGCTGGCTATCGATGCCGG CCCTTGCTGCTGATGCCGGGTCCTGGATGGA GCGACTTGCGGCGGCAGAGCAGAAACAGAGT TATACCGGTACGTTCGTCTACGAACCTCAAT GGCACTCTTTTCCAGTCATGCCGTTTGGCAG CAGGTCGAAGAAGGTCAAGTGCAGGAGCGAT TGCTTCAGCTTGACGGAGCTCCGGCTGAAGT TCTGCTGGTAAATGGTCAGATGCAATGCGCT ACCGATGACCTCGCGGCGCAAGTGCGTGAAG CGCAGGCTTGGCACGGGCAGCGTCTCGATCC GAAAGCACTCTCCGAGTGGTAgggattaccc tgttatc | partGFF27_GFF39 0mucA deletion construct for Isothermal assembly into pEX100T; 5prime 358 nt plus 3prime 358 nt plus flanking sequence on ends | 749 | 1 |
| partGFF28 | CCTGTTATCCCTACCCGGGcgcatgcttgga ggggagaacttttgcaagaagcccgagtcta tcttggcaagacgattcgctgggacgctcga agctcctccaggttcgaagaggagcatcatg ctaacccaggaacaggatcagcaactggttg aacgggtacagcgcggagttcaagcgggctt tcgatctgctggtactgaaataccagcacaa gatactgggattgatcgtgcggttcgtgcac gacgcccaggaagcccaggacgtagcgcagg aagccttcatcaaggcataccgtgcgctcgg caatttccgcggcgatagtgctattatacct | partGFF28 PAO1 mucA 5prime 716 nt flank for assembly with partGFF29 for a seemless ko construct intoPEX100T | 750 | 2 |

TABLE 5-continued

Synthesized DNA sequences

| Sequence name | Sequence | Notes | Length | SEQ ID NO: |
|---|---|---|---|---|
| | ggctgtatcggatcgccatcaacaccgcgaa<br>gaaccacctggtcgctcgcgggcgtcggcca<br>ccggacagcgatgtgaccgcagaggatgcgg<br>agttcttcgagggcgaccacgccctgaagga<br>catcgagtcgccggaacgggcgatgttgcgg<br>gatgagatcgaggccaccgtgcaccagacca<br>tccagcagttgcccgaggatttgcgcacggc<br>cctgaccctgcgcgagttcgaaggttttgagt<br>tacgaagatatcgccaccgtgatgcagtgtc<br>cggtggggacggtacggtcgcggatcttccg<br>cgctcgtgaagcaatcgacaaagctctgcag<br>cctttgagcgagaagcctgacacagcggcaa<br>atgccaagagaggtatcgctGGAGAGACATG<br>CGCA | | | |
| partGFF29 | CAAGAGAGGTATCGCTggagagacatgcgca<br>ccacctccctgttgcttttgcttggcagcct<br>gatggcggttcccgccactcaggctgccgac<br>gcttccgactggctgaatcgtctcgccgagg<br>ccgatcgccagaacagtttccaaggcacctt<br>cgtctacgagcgcaatggcagcttctccacc<br>catgagatctggcatcgcgtggagagcgatg<br>gtgcggttcgcgagcgcctgctccagctcga<br>cggcgcgcgccaggaagtggtccgggtcgac<br>gggcgcacccagtgcatcagcggcggcccttg<br>ccgaccaactggccgatgcccagctgtggcc<br>ggtgcgcaagttcgatccctcccagctggct<br>tcctggtacgacctgcgcctggtcggcgaat<br>cccgtgtcgccggccgcccggcagtggtcct<br>tgcggtgactccgcgcgaccagcatcgctac<br>ggcttcgagctgcacctggaccgcgacaccg<br>gcctgccgttgaagtcgctgctgctgaacga<br>gaaggggcagttgctcgagcgcttccagttc<br>acccagttgaataccggcgcggcacctgccg<br>aagaccagttgcaggcgggcgccgaatgcca<br>ggtcgtcggcccggccaaggccgacggcgag<br>aagaccgtggcctggcgctcggaatggctgc<br>cgccaggatcaccctgacccgcagtttcatg<br>cgtccatccggtcaccCGGGATTACCCTGTT<br>ATC | partGFF29_PAO1<br>mucA 3prime<br>716 nt flank for<br>assembly with<br>partGFF28 for a<br>seemless ko<br>construct<br>intopEX100T | 750 | 3 |
| partGFF30 | cctgttatccctacccgggAGCTTGCTTGGA<br>GGGGAGAACTTTTGCGTAAGACCCGAGTCTA<br>TCTTGGCAAGCTGATTCGCTTACGGGCGCAA<br>GCCTCCTCCAAGCGTTACGAGGAGAATGCAT<br>GCTAACCCAGGAAGATGATCAGCAACTGGTC<br>GAGCGAGTGCAGCGTGGTGACAAGCGTGCCT<br>TCGATCTGTTGGTGCTGAAGTATCAGCACAA<br>GATCCTCGGTCTGATCGTGCGATTCGTGCAC<br>GACACCCACGAGGCTCAGGATGTCCTCAGG<br>AGGCGTTCGTAAAAGCCTACCGAGCGCTTGG<br>AAACTTTCGCGGTGACAGTGCGTTCTATACA<br>TGGCTGTACCGCATCGCCATCAACACGGCGA<br>AGAATTATCTGGTGTCCCGCGGTCGGCGGCC<br>GCCAGATAGTGATGTCAGTAGCGATGACGCG<br>GAGTTCTATGATGGCGATCACGGCCTCAAGG<br>ACATCGAGTCACCGGAGCGGGCATTGCTGCG<br>CGACGAGATCGAAGCCACCGTGCATCGAACC<br>ATCGCCCAACTGCCGGATGATTTGCGCACGG<br>CCCTGACCCTGCGTGAGTTCGAAGGCTTGAG<br>TTACGAGGACATTGCAGGCGTCATGCAATGC<br>CCGGTAGGCACGGTGCGTTCGGGATATTCC<br>GTGCACGTGAGGCAATTGATAAGTCCCTGCA<br>ACCTCTGTTGCAGGAAACCTAAGGCAGCGGC<br>GACAGCCAAGAGAGGAACACCgcgctaagga<br>gtcac | partGFF30 GFF238_<br>mucA_5prime<br>715 ntflank<br>ForAssembly<br>IntopEX100T | 749 | 4 |
| partGFF31 | ccaagagaggaacaccGCGCTAAGGAGTCAC<br>ATGCGCGCGATTCCCCTCTACCTTCTCGGTG<br>GTCTGCTGGCGTTGCCGGTTCAGGCCTCCGA<br>GGTGCAGGACCTGCTCGGGCGTCTCGCTGCG<br>GCGGAGCGCCAGCAAAGCTTCCAGGGCACGT<br>TCATCTATGAGCGTAATGGGAGTTTTTCTAC<br>CCATGCCGTGTGGCATCGGGTGGAGGAGGGG | partGFF31_GFF238_<br>mucA_3prime<br>714 ntflank<br>ForAssembly<br>IntopEX100T | 750 | 5 |

TABLE 5-continued

Synthesized DNA sequences

| Sequence name | Sequence | Notes | Length | SEQ ID NO: |
|---|---|---|---|---|
| | GGCGCAGTTCGCGAACGCCTTCTGCAACTCG ATGGGCCTGCTCAGGAAGTGCTGAAAGTCGA TGGTCAGGCTCAGTGCGTCACTGGCGCGTTG GCCGACCAGGTCAGTGAAGGGCAGGCATGGC CTGCTCGCCAGCTGGATGCCGAGCAACTGAG CGACTGGTATGACATTCGTGTCGCTGGCAAG TCGCGCATTGCCAATCGTCCAGCGGTCGTTC TGGTGTTGGCCCCCAAGGACCAGCATCGCTA CGGCTTCGAATTGCATCTGGATCGTGAGACC GGGCTGCCGCTGAAGTCCCTGCTGTTGAACG AGCGCGGCCAGCTTCTGGAACGCTTCCAGTT CGCCCAACTGGATACTTCTGTACCGGCTGAA AATGCCATGCAGCCTAGCTCCAGCTGCAGGC CGGTGCGGTTCCGCGCTGCCGACAGCATGGA CGAAGGCAGTTGGCGATCCGACTGGTTGCCG CCGGGTTTCACTCTGACCACTGCGCAGGTGC GTCGCGGGCCTGCCGCTcccggattaccctg ttatc | | | |
| partGFF32 | cctgttatccctacccgggAGCTTGCTTGGA GGGGAGAACTTTTGCGTAAGACCCGAGTCTA TCTTGGCAAGCTGATTCGCTTACGGGCGCAG ACCTCCTCCGAGCGTTATGAGGAGAGTGCAT GCTAACCCAGGAAGATGATCAGCAGCTGGTC GAGCGAGTGCAGCGCGGTGACAAGCGTGCCT TCGATCTGTTGGTGCTGAAGTATCAGCACAA GATCCTCGGTTTGATCGTGCGATTCGTGCAC GACACCCACGAGGCTCAGGATGTCGCTCAGG AGGCTTTCGTAAAAGCCTACCGAGCGCTTGG AAACTTTCGCGGTGACAGCGCGTTCTATACA TGGCTGTACCGCATCGCCATCAACACGGCGA AGAATTATCTGGTGTCACGCGGTCGGCGGCC GCCAGATAGTGATGTCAGTAGCGATGACGCG GAGTTCTATGACGGCGACCACGGCCTGAAGG ACATCGAGTCACCGGAGCGGGCATTGCTGCG CGACGAGATCGAAGCCACCGTGCATCGAACC ATCGCCCAGTTGCCGGATGATTTGCGCACGG CCCTGACCTTGCGTGAGTTCGAAGGCTTGAG TTACGAGGACATTGCCGGCGTCATGCAGTGT CCGGTAGGTACGGTGCGTTCGCGGATCTTCC GTGCGCGTGAGGCAATTGATAAGTCCCTGCA GCCTCTGTTGCAGGAAACCTAAGGCAGCGGC GACAGCCAAGAGAGGAACACCgcgctaagga gtcac | partGFF32_GFF248_ mucA_5prime 715 ntflank ForAssembly IntopEX100T | 749 | 6 |
| partGFF33 | ccaagagaggaacaccGCGCTAAGGAGTCAC ATGCGCGCGATTCCCCTCTACCTTCTCGGTG GTCTGCTGGCGTTGCCGGTTCAGGCCACTGA GGTGCAAGACTTGCTCGGGCGCCTCGCTGCG GCAGAGCGCCAGCAAAGCTTCCAGGGCACGT TCATCTATGAGCGCAATGGAAGTTTTTCCAC CCATCTCCGTGTGGCATCGCGTAGAGGAGGG GGGCGAAGTTCGCGAGCGCCTTCTGCAGCTC GATGGGCCTGCCCAGGAGGTGCTGAAAGTCG ATGGCCAGGCTCAGTGCGTCACTGGCGCGTT GGCTGACCAGGTCAGTGAAGGGCAGGCTTGG CCTGCTCGTCAGTTGGCTGTCGAGCAATTGA GCAACTGGTATGACATTCGTGTCGTGGGTCA GTCGCGCATAGCCAATCGTCCGGCAGTCGTT CTGGTGCTGGCGCCCAAGGACCAGCATCGCT ACGGCTTCGAATTGCATCTGGACCGGGAGAC CGGTCTGCCGTTGAAATCCCTCCTGTTGAAC GAGCCTTGGCCACTCTACTGGAGCGCTTCCA GTTCGCTCAGCTCTGATACCTCTGTACCCGT TGAGGATGCCATGCAGCCGAGTTCGAGCTGC AGGCCGGTGCGTTTTCGTGCTGCCGACAGCA TGGCCGAAGGTACCTGGCGATCCGACTGGCT GCCGCCGGGCTTTACTCTGACTACTGCGCAG GTACGCCGCGTGCCTTCCGCTcccagggatt accagttatc | partGFF33_GFF24 8_mucA_3prime 714 ntflank forAssembly IntopEX100T | 750 | 7 |

TABLE 6

DNA oligonucleotides

| Primer name | Sequence | Description | SEQ ID NO: |
|---|---|---|---|
| prGFF123 | CAGGCCTAACACATGAAGTC | 63F primer for bacterial 16S (Yamane, 2008) | 8 |
| prGFF124 | GGGCGGWGTGTACAAGGC | 1387R primer for bacterial 16S (Yamane, 2008) | 9 |
| prGFF533 | gaattcctgcagcccaaatGAGGCGGTAACAGGGGAT | Fwd Overlapping primer for Gibson assembly of GumAtoM (ConstructI) into pGFF80 cut with SmaI and XbaI | 10 |
| prGFF534 | gcggtggcggccgctctagaCCTTGCTGACCTTCCACAG | Rev Overlapping primer for Gibson assembly of GumAtoM (ConstructI) into pGFF80 cut with SmaI and XbaI | 11 |
| prGFF556 | ttcagcatacagataaaaactgcc | 1200 to 1177 nt before B. subtilis NCIB 3610 TasA (forward orientation) | 12 |
| prGFF557 | ggtaagctcccctttattgaatga | 1 to 25 nt before B. subtilis NCIB 3610 TasA (rc) | 13 |
| prGFF558 | taacagcaaaaaaagagacggccca | 1 to 26 nt after end of B. subtilis NCIB 3610 TasA | 14 |
| prGFF559 | tattgtcactaggtcttcacctagtc | 1200 to 1175 nt after end of B. subtilis NCIB 3610 TasA (rc) | 15 |
| prGFF560 | CGATATAAAATCATTCAATAAAAGGGGAGCTTACCttcaacaaacgggattgacttttaaaaag | -35 to -1 upstream at B. subtilis NCIB 3610 TasA plus -106 to -77 nt at cat ORF in pNW33N | 16 |
| prGFF561 | TATGAATACTGGGCCGTCTCTTTTTTTTGCTGTTAgtcgggaaacctgtcgtgccag | 35 to 1 nt downstream of B. subtilis NCIB 3610 TasA ORF (rc) plus 100 to 78 nt after cat ORF in pNW33N (213 to 235 in pNW33N) | 17 |
| prGFF599 | ggcggttcctctcttggctgtcgcc | -1 to -25 nt at mucA in P stutzeri DSM 10701_well conserved | 18 |
| prGFF600 | TTAGGGAGAAACATGCGCGTA | 1 before end to 20 nt after mucA in P stutzeri A1501, DSM4166, ATCC17588, CCUG29243_note that stop differs from 10701, but this sequence conserved | 19 |
| prGFF605 | TTGCAGGATAGCTTGCTAGGA | CHECK_PRIMER_-725 to -705 at mucA in P stutzeri DSM 10701_Int difference from other stutzeri genomes | 20 |
| prGFF610 | GCTCGTGCGGCCAGCATGGAAGA | 29 to 6 nt before end of mucA in P stutzeri A1501, DSM4166, ATCC17588, CCUG29243 note that stop differs from 10701, but this sequence conserved | 21 |

TABLE 6-continued

DNA oligonucleotides

| Primer name | Sequence | Description | SEQ ID NO: |
|---|---|---|---|
| prGFF612 | TCCAGCGCAACGACCCGCCC | 997 to 978 nts after mucA in P stutzeri A1501, DSM4166, ATCC17588_note that this differs from 10701 | 22 |
| prGFF643 | ctggaagtttggctcatgtc | Forward primer at nt 5 in P. alcaliphila 34 sequence_mucA plus 1 kb flanks | 23 |
| prGFF644 | agtctatcaggcaagctgattc | Forward primer at nt 323 in P. alcaliphila 34 sequence_mucA plus 1 kb flanks | 24 |
| prGFF645 | gtgagttcgaaggctgagttac | Forward primer at nt 837 in P. alcaliphila 34 sequence_mucA plus 1 kb flanks | 25 |
| prGFF646 | gcttctccggtactctcggta | Forward primer at nt 1355 in P. alcaliphila 34 sequence_mucA plus 1 kb flanks | 26 |
| prGFF647 | gtgctgaaagtcgatggtcag | Forward primer at nt 1823 in P. alcaliphila 34 sequence_mucA plus 1 kb flanks | 27 |
| prGFF648 | tctgaaaggtcgcgtcgt | Forward primer at nt 2353 in P. alcaliphila 34 sequence_mucA plus 1 kb flanks | 28 |
| prGFF649 | taatcttatcgccgctcatttcc | Reverse primer at nt 222 in P. alcaliphila 34 sequence_mucA plus 1 kb flanks | 29 |
| prGFF650 | cgtcatagaactccgcgtcat | Reverse primer at nt 713 in P. alcaliphila 34 sequence_mucA plus 1 kb flanks | 30 |
| prGFF651 | gcttccattgcgctcatagatg | Reverse primer at nt 1735 in P. alcaliphila 34 sequence_mucA plus 1 kb flanks | 31 |
| prGFF652 | cggatcgccaggtaccttc | Reverse primer at nt 2228 in P. alcaliphila 34 sequence_mucA plus 1 kb flanks | 32 |
| prGFF653 | ctcgagcgccactacacg | Reverse primer at nt 2568 in P. alcaliphila 34 sequence_mucA plus 1 kb flanks | 33 |
| prGFF662 | CTTGCTGGCCGGGCGCATCGC | 9076 to 9096 in PelAtoG gene cluster in P. alcaliphila 34 (note that numbering is based on PAO1 sequence); 224 to 204 nt before PelF | 34 |
| prGFF663 | GGGCCGGAACTGATCAGGCCGGC | 10981 to 10959 (rc orientation) in PelAtoG in P. alcaliphila 34 (note that numbering is based on PAO1 sequence); 101 to nt 78 nt after end of PelF | 35 |

TABLE 6-continued

DNA oligonucleotides

| Primer name | Sequence | Description | SEQ ID NO: |
|---|---|---|---|
| prGFF664 | GAGGGAACCTGGCCCTATGT | 9355 to 9374 in PelAtoG gene cluster in *P. alcaliphila* 34 (note that numbering is based on PAO1 sequence); In PelF | 36 |
| prGFF665 | TTCGTCAATTACTTCTGGAC | 9766 to 9785 in PelAtoG in *P. alcaliphila* 34 (note that numbering is based on PAO1 sequence); In PelF | 37 |
| prGFF668 | TCGACCAGCTCGCGACACGAGCC | 10601 to 10578 (rc orientation) in PelAtoG in *P. alcaliphila* 34 (note that numbering is based on PAO1 sequence); In PelF | 38 |
| prGFF669 | TCGATGCCATTGGGGATCACC | 10202 to 10182 (rc orientation) in PelAtoG in *P. alcaliphila* 34 (note that numbering is based on PAO1 sequence); In PelF | 39 |
| prGFF672 | CTGTCGGTMGGGGAGTTCGACGGC | 289 to 312 in *P. aeruginosa* PelA; alignment with *P. protogens* matches was used to generate consensus sequence here | 40 |
| prGFF673 | CAGGGCTACGCCGGCCTGTTCCT | 454 to 476 in *P. aeruginosa* PelA; alignment with *P. protogens* matches was used to generate consensus sequence here | 41 |
| prGFF674 | AAGGCGAACGGRTCGAGGATCCAGCG | 1496 to 1471 (rc) in PAO1 PelA; alignment with *P. protogens* matches was used to generate consensus sequence here | 42 |
| prGFF675 | GGCCCGACYTCGCCTTCGAT | 1712 to 1693 (rc) in PAO1 PelA; alignment with *P. protogens* matches was used to generate consensus sequence here | 43 |
| prGFF676 | ATGGCGGGTATAGGCTTTGAACTG | 10826 to 10849 in PelAtoG in *P. alcaliphila* 34 (note that numbering is based on PAO1 sequence); Beginning of PelG | 44 |
| prGFF677 | ATGGCGGTGTTCCTGGTGCG | 11678 to 11697 in PelAtoG in *P. alcaliphila* 34 (note that numbering is based on PAO1 sequence); In PelG | 45 |

TABLE 6-continued

DNA oligonucleotides

| Primer name | Sequence | Description | SEQ ID NO: |
| --- | --- | --- | --- |
| prGFF678 | TCGAACTCGAGATCGTCCAGCGC | 12174 to 12152 (rc orientation) in PelAtoG in *P. alcaliphila* 34 (note that numbering is based on PAO1 sequence); In PelG | 46 |
| prGFF680 | TCAGCGATTGAGCATGAAGGTTTC | 12196 to 12173 (rc orientation) in PelAtoG in *P. alcaliphila* 34 (note that numbering is based on PAO1 sequence); Note that first 8 nts are from PAO1 sequence (missing in blast match sequence from Pa 34); End of PelG | 47 |
| prGFF681 | TTGATCTGCGCCCAGCCGGTGATG | 1286 to 1263 (rc) in PAO1 pslA | 48 |
| prGFF682 | TTCAAGTTCCGCTCGATGTAC | 1003 to 1023 in PAO1 pslA | 49 |
| prGFF683 | ATGCGTCAGCTTTTGCACGGTAG | 1 to 23 in *P. mendocina* pslA; ymp and DLHK sequences are identical | 50 |
| prGFF684 | TCAGTAGGCCTCGCGGGTGAAGA | 1434 to 1412 (rc) in *P. mendocina* pslA; ymp and DLHK sequences are identical | 51 |
| prGFF685 | GACGTGATCGGCAGCGAGGACGCCTA | In *P. mendocina* pslA-O blast match at 3431 to 3456, according to alignment with PAO1 *P. aeruginosa* numbering | 52 |
| prGFF686 | CCCGAGGACGTGATCGGCAGCGA | In *P. mendocina* pslA-O blast match at 3425 3447, according to alignment with PAO1 *P. aeruginosa* numbering | 53 |
| prGFF687 | CCATCTACGAGCTGACGCTGT | In *P. mendocina* pslA-O blast match at 4067 to 4087, according to alignment with PAO1 *P. aeruginosa* numbering; in PslD ORF | 54 |
| prGFF688 | AGATAGAGGTCGACGCCCTCGAT | In *P. mendocina* pslA-O blast match at 4544 to 4522 (rc), according to alignment with PAO1 *P. aeruginosa* numbering; in PslD ORF | 55 |
| prGFF689 | CGGAATGTACGAATTTCGATCATG | In *P. mendocina* pslA-O blast match at 4650 to 4528 (rc), according to alignment with PAO1 *P. aeruginosa* numbering; after PslD ORF | 56 |
| prGFF690 | CGAAAGGAACGAATTTCGATCATG | In *Pseudomonas pseudoalcaligenes* strain CECT 5344 pslA-O blast match at 4650 to 4528 (rc), according to alignment with PAO1 *P. aeruginosa* numbering; after PslD ORF | 57 |

TABLE 6-continued

DNA oligonucleotides

| Primer name | Sequence | Description | SEQ ID NO: |
|---|---|---|---|
| prGFF691 | ACAAGCTCGCCATCCCGC CCGCCTA | In *Pseudomonas alcaligenes* strain MRY13 pslA-O blast match at 17569 to 17593, according to alignment with PAO1 *P. aeruginosa* numbering; in PslN ORF | 58 |
| prGFF692 | CGCAAGCAGTACCGCTAC CACCCGC | In *Pseudomonas alcaligenes* strain MRY13 pslA-O blast match at 17661 to 17685, according to alignment with PAO1 *P. aeruginosa* numbering; in PslN ORF | 59 |
| prGFF693 | CGCAGGTGCTCCAGGGCC AG | In *Pseudornonas alcaligenes* strain MRY13 pslA-O blast match at 18196 to 18177 (rc), according to alignment with PAO1 *P. aeruginosa* numbering; in PslN ORF | 60 |
| prGFF694 | GCCCAGGTGCGGTAGTCC TTGGCG | In *Pseudomonas alcaligenes* strain MRY13 pslA-O blast match at 18166 to 18143 (rc), according to alignment with PAO1 *P. aeruginosa* numbering; in PslN ORF | 61 |
| prGFF695 | cctgttatccctacccgg gCAGCAAGCGCCTGGCCG AC | pslD upstream flank knockout primer; 19 nts from pEX100T (upstream) at SmaI site plus 3319 to 3337 in pslAtoO sequence (525 to 507 nt before pslD); based on Byrd 2009 knockout construct | 62 |
| prGFF696 | CAGGAAGTGCTCCCTCAT GAAAcgctgaggagcgac atcgccatgatag | pslD downstream flank knockout primer 22 nt before pslD and first 6 nt of pslD plus Last 6 nt of pslD and 21 nt after pslD | 63 |
| prGFF697 | ctatcatggcgatgtcgc tcctcagcgTTTCATGAG GGAGCACTTCCTG | pslD upstream flank knockout primer; Reverse complement of pslDOLF | 64 |
| prGFF698 | gataacagggtaatcccg ggGATCTCCATCACCGTC GAG | pslD downstream flank knockout primer; 20 nts from pEX100T (downstream) at SmaI site plus 5141 to 5123 in pslAtoO sequence (527 to 509 after pslD end) | 65 |
| prGFF699 | cctgttatccctacccgg gCGACGTCCGCCTGCTGG CCTAC | pelF upstream knockout primer; 19 nts from pEX100T (upstream) at SmaI site plus 8821 to 8842; 480 to 459 before start of pelF orf; based on Colvin '12 | 66 |

TABLE 6-continued

DNA oligonucleotides

| Primer name | Sequence | Description | SEQ ID NO: |
|---|---|---|---|
| prGFF700 | CATGCAATCTcggtgtgt tcggtcatgtcc | pelF upstream flank knockout primer; 1 to 10 nt before end of PelF (rc) plus +16 to -4 nt at PelF start (rc) | 67 |
| prGFF701 | cgaacacaccgAGATTGC ATGACATGGCCG | pelF downstream flank knockout primer; 6 to 16 nt after start of PelF plus last 11 nt of PelF and 8 nt after PelF | 68 |
| prGFF702 | gataacagggtaatcccg ggCCAGCAGGATGCGTTT GTAGG | pelF downstream knockout primer; 20 nts from pEX100T (downstream) at SmaI site plus 11321 to 11301 in pelAtoG; 497 to 477 after end of pelF orf | 69 |
| prGFF723 | ATCAGGCCGCCATACAGG TAGGC | 10914 to 10892 in PelAtoG (rc orientation) 89 to 67 in PelG in *P. alcaliphila* 34, GFF238, and GFF248 (match all three) based on numbering in PAO1 sequence PelAtoG | 70 |
| prGFF724 | AGCATCACGCTGATGATC GACA | 10956 to 10935 in PelAtoG (rc orientation) 131 to 1110 in PelG in *P. alcaliphila* 34, GFF238, and GFF248 (match all three) based on numbering in PAO1 sequence PelAtoG | 71 |
| prGFF725 | TCCTGGCCTACTCGATGC TCGA | 8832 to 8853 in PAO1 PelAtoG; 518 to 539 in PelE (Pao1): Matches *P. alcaliphila* 34 sequence | 72 |
| prGFF726 | CTGGCGCGTTGGTACTGG GAACT | 8948 to 8970 in *P. alcaliphila* 34 PelAtoG (numbering based on PAO1); 634 to 656 in PelE (numbering based on PAO1) | 73 |
| prGFF727 | GTCCAGAAGTAATTGACG AA | 9785 to 9766 in PelAtoG (rc orientation) 485 to 466 in PelF in PAO1; identical match to *P. alcaliphila* 34 | 74 |
| prGFF728 | TCCTTCTGACCGCCGATG AA | 9464 to 9445 in PelAtoG (rc orientation) in *P. alcaliphila* 34 (numbering based on PAO1); 164 to 145 in PelF; 1 nucleotide mismatch with PAO1 | 75 |
| prGFF729 | CAGCGTCTGCTGGAAGGC AGCCAG | 8044 to 8067 in PAO1 PelAtoG; 271 to 248 before PelE (Pao1); Matches *P. alcaliphila* 34 sequence | 76 |

TABLE 6-continued

DNA oligonucleotides

| Primer name | Sequence | Description | SEQ ID NO: |
|---|---|---|---|
| prGFF730 | TGAATGATCAGCAAGTGGCT | 8312 to 8331 in PAO1 PelAtoG; -3 to +17 at PelE; Matches P. alcaliphila 34 sequence | 77 |

TABLE 7

Summary of sequencing data

| Strain | gene/ locus | contig | SEQ ID NO: | Sequence |
|---|---|---|---|---|
| P. alcaliphila AL15-21; GFF238 | mucA | 1 | 78 | ctggaagtgttggctcatgtccgagttccgcgtgaaagcgagccctagtatatagagag gggcagcggcacaatagccagcttatgaccgaccgcggtgctcgggaacatcttagtca ttaaggttccatagagggtcgcccatataagggagagcgcatgcgcgtgcctgcatctg aagtcagcggagggtgtggaaatgagcggcgataagattatttgcgcgagcggaaaggt tccgctggcgccattccaggcagagggaagaaaactctgcgggattgcttgcttggagg ggagaacttttgcgtaagaccgagtctatcttggcaagctgattcgcttacgggcgct tagcctcctccaagcgttacgttggagaatgcatgctaacccaggaagatgatcagcaa ctggtcgagcgagtgcagcgtggtgacttagcgtgccttcgatctgttggtgctgaagt atcagcacaagatcctcggtctgatcgtgcgartcgtgcacgacacccacgaggctcag gatgtcgctcaggaggcgttcgtaaaagcctaccgagcgcaggattacatcgcggtgac agtgcgttctatacatggcgtaccgcatcgccatcaacacggcgaagaattatctggt gtcccgcggtcggcggccgccagatagtgatgtcagtagcgatgacgcggagttctatg atggcgatcacggcctcaaggacatcgagtcaccggagcgggcattgctgcgcgacgag atcgaagccaccgtgcatcgaaccatcgcccaactgccggatgatttgcgcacggccct gacccctgcgtgagttcgaaggcttgagttacgaggacattgcaggcgtcatgcaatgcc cggtaggcacggtgcgttcgcggatattccgtgcacgtgaggcaattggaagtccctgc aacctctgttgcaggaaacctaaggcagcggcgacagccaagagaggaacaccatgagt cgtgaaaccctgcaggaatcgctgtccgcggtgatggataacgaagcggacgaactgga actgcggcgtgtgctcgcagccagcgaggatggcgagctgcgtggcacctggcgcgtta ccaggtcgcccgtgcagccatgcatcgtgaactgttggtgccgcaactggacatcgcat ctgcggtctccgcggcgctggccgacgaagccgttccggcacgcaaggcgccgatctgg cgtagtgtcggtcgcgtagccgtggcagcatcggtgaccgttgcagtgctggcgggtgt gcgatctacaatcaggatgacctgagcggcgctcaactggcccagcaggagacttctcc ggtactctcggtacctcaggtccagggtcctgcactgctcgctggttacaacagcagcg aggaagccggcgaagccgccgaagcaggcactgccagctggcatgagcagcgcctgccg aactacctgcgtcaacatgcgcaggaagccgtgatgggtaccggtgaaaccgctctgcc ttatgctcgggctgcgagtctggattaaccgctaagcgctttaggagtcacatgcgcgc gattcccctctacatctcggtggtctgctggcgagccggacaggcctccgaggtgcagg acctgctcgggcgtctcgctgcggcggagcgccagcaaagcttccagggcacgttcatc tatgagcgtaatggagtattctacccatgccgtgtggcatcggtggaggaggggggc gcagttcgcgaacgccttctgcaactcgatgggcctgctcaggaagtgctgaaagtcga tggtcaggctcaggcgtcactggcgcgaggccgaccaggtcagtgaagggcaggcatgg cctgctcgccagctggatgccgagcaactgagcgactggtatgacattcgtgtcgctgg cttagtcgcgcattgccaatcgtccagcggtcgttctggtgttggccccccaaggaccttt gcatcgctacggcacgaattgcatctggatcgtgagaccgggagccgctgaagtccctg ctgttgaacgagcgcggccagcttctggaacgcttccagttcgcccaactggatacttc tgtaccggctgaaaatgccatgcagcctagctccagctgcaggccggtgcggttccgcg ctgccgacagcatgacgaaggcagttggcgatccgactggttgccgccgggtttcact ctgaccactgcgcaggtgcgtcgcgggcctgccgctgatgactccgtcacctatctgat gtacggcgatggcctggtgcgattctcggttttttctcgagcctcttaaaggtcgcgtcg tcgaagacgcgcgcagtcagttgggtccaaccgtcgccgtttcgcgacggatgagcacc gatgcggtgacgtgatggttaccgtggtcggtgagattcctctggggactgccgagcg catagccctgtcgatgcgcgccggagtgcctgaacaggctagccaatgatcgaagagca ggggcgtgtagtggcgctcga |
| P. toyotomiensis 1IT-3; GFF248 | mucA | 1 | 79 | tggctcatgtccgagttccgcgtgaaagcgagccctagtatatagagaggggcagcggc acaataggtggcttatgaccgaccgcggtgctcgggaactttcttagtcgttaaggttc catagagggtcgcccatataagggagagcgcagcgcgtgcctgcatctgaagtcagcgg agggtgtggaaatgagcggcgataagattatttgcgcgagcggaaaggttccgctggcg ccattccaggcagagggaagaaaactctgcgggaagcttgcttggaggggagaactatg cgtaagaccgagtctatcttggcaagctgattcgcttacgggcgcttgacctcctccg agcgttatgaggagagtgcggctaacccaggaagatgatcagcagctggtcgagcgagt gcagcgcggtgacaagcgtgccttcgatctgttggtgctgaagtatcagcacaagatcc tcggtttgatcgtgcgattcgtgcacgacacccacgaggctcaggatgtcgctcaggag gcttcgtaaaagcctaccgagcgcttggaaactttcggtgacagcgcgttctatac atggctgtaccgcatcgccatcaacacggcgaagaattatctggtgtcacgcggtcggc ggccgccagatagtgatgtcagtagcgatgacgcggagactatgacggcgaccacggcc tgaaggacatcgagtcaccggagcgggcattgctgcgcgacgagatcgaagccaccgtg catcgaaccatcgcccagttgccggatgatttgcgcacggccctgaccttgcgtgagtt |

TABLE 7-continued

Summary of sequencing data

| Strain | gene/locus | contig | SEQ ID NO: | Sequence |
|---|---|---|---|---|
| | | | | cgaaggcttgagttacgaggacattgccggcgtcatgcagtgtccggtaggtacggtgc<br>gttcgcggatcttccgtgcgcgtgaggcaattgataagtccctgcagcctagttgcagg<br>aaacctaaggcagcggcgacagccaagagaggaacaccatgagtcgtgaaaccctgcag<br>gaatcgctgtccgcggtgatggataacgaagcggacgaactggaactgcggcgtgtgct<br>cgcagccagcgatgatggcgagagcgcggcacctggtcgcgttaccagatcgcccgtgc<br>agccatgcatcgtgagctgtggtgccgcaactggacatcgcatctgcggtttccgcggc<br>gctggccgacgaagccgtcccggcacgcaaggcgccgatctggcgtagtgtcgggcgcg<br>tagccgtcgcagcatcggtgaccgttgcagtgctggcgggtgtgcgcactacaatcagg<br>atgacctgagcggcgcccaattggcacagcaggaggcactccggtactctctgtaccgc<br>aggtgcaaggtcctgcgctgctcgctggttacaacagcagcgaggaagccggcgaagcc<br>gccgaagcaggcactgccagctggcatgagcagcgtttgccgaactacctgcgtcaaca<br>tgcgcaggaagccgtgatgggtaccggtgaaaccgctctgccttatgacgggctgcaag<br>tctgaaaaccgctaagcgctaaggagtcacatgcgcgcgattcccctctaccttctcg<br>gtggtctgctggcgagccggttcaggccactgaggtgcaagacttgctcgggcgcctcg<br>ctgcggcagagcgccagcaaagcttccagggcacgttcatctatgagcgcaatggaagt<br>tatccacccatgccgtgtgcatcgggtagaggagggggggcgaagttcgcgagcgcctt<br>ctgcagctcgatgggcctgcccaggaggtgctgaaagtcgatggccaggctcagtgcgt<br>cactggcgcgttggctgaccaggtcagtgaagggcaggcttggcctgctcgtcagttgg<br>ctgtcgagcaattgagcaactggtatgacattcgtgtcgtgggtcagtcgcgcatagcc<br>aatcgtccggcagtcgttctggtgctggcgcccaaggaccagcatcgctacggcttcga<br>attgcatctggaccgggagaccggtctgccgttgaaatccctcctgttgaacgagcgtg<br>gccagctactggagcgcttccagttcgctcagctggataccctgtaccgttgaggat<br>gccatgcagccgagttcgagctgcaggccggtgcgttacgtgctgccgacagcatggcc<br>gaaggtacctggcgatccgactggctgccgccgggattactctgactactgcgcaggta<br>cgccgcgtgcctccgctgatgatcccgtcacctatctcatgtatggcgatggcctggc<br>gcgattctcggtttttctcgaaccctgaaaggtcgcgtcgtcgaggatgcacgcagcc<br>agctgggcccaaccgtcgcggtttcgcggcggatgagtaccgactctggtgacgtcatg<br>gtgaccgtggtgggtgagatccccttggggactgccgaacgcatcgcccgtccatgcg<br>cgccggagtgcctgaacaggctagccaatgatcgaggagcagggcgtg |
| P. stutzeri<br>PTA-8823;<br>GFF390 | mucA | 1 | 80 | ttgctaggaggggggagaacttagcgtaaagcccgggtctattaggcaggtcggttcgc<br>tggtgtgagcgacgctactccgctaccgaggaggagcgttcatgttgactcaggagcag<br>gaccagcagctggagaacgagtgcagcgtggtgacaagcgggcgtttgatctgaggtaa<br>tgaaataccapacaagatccttgggttgatcgtgcggttcgtgcatgactctcatgaag<br>ctcaggatgttgcccaagaggcttttatcaaagcctaccgtgcactagccaattttcgc<br>ggtgacagcgctttctacacctggctgtaccgcatcgccatcaatacggcgaagaatca<br>tctggtggcgcgcggcagacgcccgccggatagtgatgtgaaccgaggacgccgagtt<br>ttatgagggcgatcacgctctcaaggacatcgagtcaccggaacgctcgctgctcaggg<br>atgagattgaagataccgttcatcgaaccattcaacttagccagaagatttgcgtacgg<br>ctctaacactgcgtgaatttgatggtcttagttatgaagacattgcgagcgtcatgcag<br>tgtccggtgggcacagtgcgacccggatcttccgggcacgtgaagccatagataaagca<br>ttgcaacccttgttgcatgaatcctgagacagcggcgacagccaagagaggaaccgcca<br>tgagtcgtgaagccctgcatgaatcgctgtccgcggtgatggataacgaagcggacgag<br>aggaattacgtcgcatgctcgcangcgacaacccggagctacgtgctacctggtcgcgt<br>tatcaacttgcccgtgccgccatgcacaaggagttgatcgagccgcgcctggatatcgc<br>ttctgcgggtatcggctgcg |
| | | 2 | 81 | cagcatggaagaacgttagggagaaacatgcgcgtattaccgctgtatgtggtgatggg<br>gggaggctatcgatgccggcccttgctgctgatgccgggtcctggatggagcgacttgc<br>ggcggcagagcagaaacagagttataccggtacgttcgtctacgaaccgcaatggcagct<br>tttccagtcatgccgtttggcagcaggtcgaagaaggtcaagtgcaggagcgattgatc<br>agcttgacggagctccggctgaagttctgctggtaaatggtcagatgcaatgcgctacc<br>gatgacctcgccggcgcaagtgcgtgaagcgcaggcttggcacgggcagcgtctcgatcc<br>gaaagcactctccgagtggtacgaattccgtgagatcggggattcacgagttgctggcc<br>gccccgccgtgggctggctgtcgtgccgaaggatcagcaccgttacggcttcgaactct<br>gcatctcgaccaagataccgcattgccctcaagtcgctgatgctgaacgagaaagggc<br>agctgctcgagcgtaccaattcacccagttcacggctggcagtgtatctgccgagcaac<br>tgaagcccggcgccgattgcaatccagtgaccgtgaaccggcgcgaggcgaatcctaca<br>tcgccctggcgctccgactggttgccttccggcttcacgctactggatgccaacgaacg<br>acctagtcccgcctatccgaaactgtttcctggttgtcctacggtgatggtctagcgaa<br>gttttccgtgtttctggagccgctgcgcggcgccttggttgaggacgcgcgaagccaga<br>tggggcctaccgtcgcggtctctaagcgcatcagtactgcggatggcgatgtcatggtg<br>accgtggtgggcgagattccacttggtacggctgagcgggttgccctgtccatgcgagc<br>cagttcgaacaggcacaacgatgatcga |
| P. alcaliphila<br>AL15-21;<br>GFF238 | PelE to End of PelG | 1 | 82 | caggtacctcaggccgcgttgcatatcctcttctcatggcttgggaagcgccatgctgg<br>ctgcagggatctggctgctgctgccgcgccgctatcgctacccctttgccctgcagccc<br>tgttcattttcagcgtctcgacttcattccctttgattgggatgatcggcgtagcgctg<br>cgctgttccggccactactttgccgcgcaagcgcaaggtgcagtcctgggaggctactg<br>ccgttcccgagctgcctttccggccgcgcgagcgcaagcgtgagctgatgttcagcgat<br>ggcgggagcaggatgtgttacgccatgcgcgcgaccccgatcagcatcgtgacggccatc<br>ttcgcgacacgacgcatgcgcagcaaggaggccatcccgattctcaagctggcgctgcg<br>cgatccatctgacgatgttcgcctgctggcctattcgatctcgatcagcgtgaaagccg<br>aatcaaccagcgtatcgagcgtgcgaggcagatatggagagcgccagcacggaccgtaa<br>gttcgccctgcatgggcaactggcgcgctggtactgggagctcgcctatgtcggcctgg<br>cccagggcagtgtgttggagcacgtgctgcagcaggctggagccatgtgatggcggcgc |

TABLE 7-continued

Summary of sequencing data

| Strain | gene/ locus | contig | SEQ ID NO: | Sequence |
|---|---|---|---|---|
| | | | | tgcagggtggctcgggtggcgaactgcacttgcttgccgggcgcatcgccatggagcag ggcaatctcgatgaggcgttggcgcagttcgaccagtcggcgctggccgggatggatgc ggtgcaattggcgccgtatcgggctgaaatcgcgtattgcgtcaacgctatgaggaaat tccagaaatgctggcgacgatgccggccgaactgttgcaacgtcccccttcgcggcca ggctagatattggttatgagtgagaaatctgctgttcctgacgtgcagagcgtcgatgt ctgcctgttgctcgagggaacctggccgtacgtgcgcggggggtatcgagctggatca accaactgatcctggggctgccggaactgaccttctcggtgctgttcatcggcggtcag aagga |
| | | 2 | 83 | gcctacctgtatgccggcctgatcagttccggcccttgggtattgtcgatcatcagcgt gatgctcatcggcgtactgagcctgggggcggtgctgccggaaacgctgatcggtcagt tcctggtcaccgtgacgtacctgatggccacgtcgctgattctcaccggcggactgcag ctgttcttcacccgcttcgtctccgaccggctgttcgagcggccgctggacctgatcct cccaatctgatcgggatactgctgctggtgacgatcttctcggggctgctggccggtctg tgtgatgggcctgctgttcgatcagtcgtttacctatcgcctgctggtgatggccaact tcgtggtgctgtgcaacctctggctggtgatcatcttcctgtcggggatgaaggcttat aaccgcatcctcggggtgatgtttctcggctactcgtgatggtcgcctcggcctatct gctgcgctttctgaatatcgacgcttgctgctgggcctgctgatcggtcattccagcc tgctgttcatcttcctgttcgacatcctgcgcgagtaccggccgagcgcctggtcgcg ttcgattttctcaagcgtcgccaggtgttcggcagcctgctgctgacaggactttgcta caacctgggcatctggatcgacaagttcatcttctgtcaaccctcgacttccgaagc cgtgatcggccgttgcgggcctcgatcctctatgacctgccgatcttccttgcctacc tgtcgatcatcccggcatggcggtgttcctggtgcgtatcgaaacggacttcgccgaa tggtacgagcgggtctatgacgcgatccgcggcggtgaaaccctgcagcacatcggctg gctcaaggagcagatgatcctggcgattcgccagggcctgatggagatgtgcaaggttc agggctgaccctggttctgctattcctgctcgccgccagttgttgtcctggctgggc atctcgcactactacctgccgctgttctacatcgacgtgataggcgtgagcattcagt ggtgttcatggccttgctcaacgtgttcttctatctggacaagcgtgccatcgtcctcg aactctgcgttctcttcgtcctggcaaacggcgcgttgaccctgttcagccagatgctt ggcccgaccttcttcggctatggcttcaccctgtcgctgctgctgtgcgtactcctcgg gttgtatcgtctcaacgaggcgcttgatgatctcgagttcgaaaccttcatgctcaatc gctga |
| P. toyotomie nsis HT-3; GFF248 | PelE to End of PelG | 1 | 84 | atgatcagcaagtggctgtttagcggcgctgcgctgctcgaggtcgggagctgggccag tgcggtcagcgatctcccgattcatcaggccgcgttgctctatgcctccgcgcatggcc tgggcagtgcgatgctggctgccgggatctggctgctgctgccgcgccgctatcgctac cccttgccttggagcctgctgttcattttcagcatctcgttcttcatcccctgatcgg natgatcggcgtggctggcgttgtttcccgccctctacttgccgcgaaagggcaagg tgcagtatgggaggcgaccgccgacccgaactgcctttccgaccgcgtgagcgcaagca ggagttgatgacagcgatggtggccttcaggacgtgttgcgtcatgcgcgtgacccga tcagcgcctgacggcgatcttcgccacacgacgcatgcgcagcaaggaggccatcccga ttctcaagctggcgctgcgcgatccatcngacgacgtgcgtttgctggcntactcgatg ctcgatcagcgtgaaagccgaatcaaccagcgtatcgagcgcgctctggcagatatgga gagcgccagcacggaccgccagttcgccctgcatgggcaactggcgcgttggtactggg agcttgcctatgtcggcctggcccagggcagtgttctggagcacgtgctgcagcaggcc tggagccatgtgatggcggcgctgcagggcaactcgggtggtggagctgcacttgttggc cgggcgtatcgccatggagcagggcaatctcgacgaggcgttggcgcagttcgaccagt cggcacaggccgggatggatgcggtgcagttggcgccgtatcgggccgagatcgcgttt ttgcgtcaacgctatgaggattattccagacatgaggcgacgatgccggccgagctgtt gcaacgtcccccttcgcggctttggcaagatactggttatgagtgagaaatccgctgt tcctgacgtacagagcgtcgatgtctgtcgttgctgtagagggggacctggccctatgtgc gtgggggcggtctagctggatcaaccagctgatcctggggctgcctgagctgactttct cggtgctgttcatcggcggtcagaaggaggcctacggcaagcgccattacgctatcccg gacaacgtggtgcacattcaggagcatttcctcgaagactcctggagttcgattcccac caccagtacccgtgcgagcgctgagctgccgagctgatgctggatgtgcaccgttttcc tgcacaacccggaggaacccagcactgagcagggcgatgcattcgtcgatccctggct gccgacgcatcggccgtgaggccttcct |
| | | 2 | 85 | tcagctacatccgtagattgtggatccgcttcttcgagcgtattgggctgatcacctac cgatctgcgcactccatcatcgcgctgtacgagggcaacaggcggcgtcaggttctcga tggcgctcctgaggagcgtactagggtcattccaatggcatccgatctggccagttggg atcaggcgctgctcagccggccagttaggcgtgccgccggtggccggcctggttgggcg ggtggtaccgatcaaggacgtcaaaaccttcatccgcgccatccgtggtgtggtcagcg tcatacccgaagccgagggctggatcgtcgggccggaagaagaagatccggattacgcg gccgagtccacagcctggtggccagcctggggctgcaggacaaggtgcgttttctcgg cttccgccaggtgcgcgaagtcgtaccgcaactgggcgtgatggtgctgacgtcgatca gtgaggcgcagccgctggtggtacttgaggcctgggcggccggcacgccagtggtgacc agtgacgtcggctcgtgtcgcgagctggtcgaaggctccacgcaggaggatcgccagct cggtacggcggggaggtggtagcaattgccgacccgcaggccacctcgcgcgccattc tctcgctgttgcgcaacccggagcgctggaaggctgcgcaggctgtcggccttgagcgt gtgcggcgttactacaccgaagaactgatgctcgcgcgctatcgcgagagtatcgcgaa ggcacggagagcgtaatggcgggtatagctttgaactgaggaaggatcctgtccaagg |
| | | 3 | 86 | gatgcgcgcctacctgtatgccggcctgatcagaccggcccttgggtgttgtcgatcat cagcgtgatgctcatcggtgtactgagcctggggcggtgctgccggaaacgctgatcg gccagttcctggtcaccgtgacctacctgatggccacgtcgctgattctcaccggcggg ctgcagctgttcttcacccgcttcgtctccgaccggttgttcgagaaacgcctggacct gatcctgcccaacctggtgggcatactgctgctggtaacgatcgtctcggggctgctgg |

TABLE 7-continued

Summary of sequencing data

| Strain | gene/<br>locus | contig | SEQ<br>ID NO: | Sequence |
|---|---|---|---|---|
| | | | | caatctgcgtgttgggcttgctgttcgatcagtcgttttcctatcgcctgctggtgatg<br>gccaacttcgtggtgctgtgcaacctgtggctggtgatcatcttcctgtcggggatgaa<br>ggcctacaaccgcattctcggcgtgatgttcctcggctactcgctgatggtcgcctcgg<br>cctatctctgcgattctcaatatcgacggcctctgctgggcctgctgatcggtcactcc<br>agcctgctgttcatcttcctcttcgacatccttcgcgagtacccggccgagcgcctggt<br>cgcgttcgatttcctcaagcgccgtcaggtattcggcagcctgctgctgacagggctgt<br>gctacaacctgggtatctggatcgacaagttcatcttctggttcaacccctcgacttcc<br>gaagccgtgatcggcccattgcgcgcatcgatcctctatgacctgccgatatcctcgcc<br>tatctgtcgatcatccccggcatggcggtgtttctggtacgtatcgaaaccgacttcgc<br>cgagtggtacgagcgggtctatgacgcgatccgcggcggggaaaccctgcagcacatcg<br>gctggctcaaggagcagatgatcctggcgattcgccagggtctgatggaaatctgcaag<br>gtccaggggctgaccctggttctgctgtttctgctggcgcccagttgttgtcctggctc<br>ggcatctcgcactactacctgccgctgactatatcgacgtgatcggcgtgagcattcag<br>gtggtattcatggccttgctcaacgtgttcttctatctggacaagcgcgccatcgtcct<br>cgaactctcgttctatcgtcctggcaaacggtgcgctgaccctgttcagccagatgctt<br>ggcccgacattatcggctatggcttcaccctgtcgctgctgcigtgcgtgctcctgggg<br>ttgtatcgtct |

TABLE 8

DNA plasmid vectors

| Plasmid<br>Name | Alternative<br>name | Vector<br>backbone | Insert--Gene | Notes | E. coli<br>marker |
|---|---|---|---|---|---|
| pGFF80 | pBBR1MCS | pBBR1MCS | | Broad host plasmid; From CBS | Cam |
| pGFF93 | pNW33N;<br>BGSC<br>ECE136 | pNW33N | | From BGSC; Gram positive expression vector; E. coli; shuttle vector | Cam |
| pGFF155 | | pGFF80 | gumABCDEFGHIJKLM<br>(X. campestris) | cloned by isothermal assembly; construct I (generated with oligos prGFF533&534); verified by NGS sequencing | Cam |
| pGFF157 | ATCC<br>87436 | pEX100T | | From ATCC; Gram negative knockout vector; Amp, SacB, Ori (pMB1), OriT, LacZalpha | Amp |
| pGFF167 | | pGFF157 | mucAdelta<br>(P. stutzeri<br>GFF390) | knockout vector; cloned mucA seamless knockout construct (GFF390) into SmaI site in pGFF157 by isothermal assembly of partGFF27 (5prime 358 nt plus 3prime 358 nt); Orientation is forward in vector (reverse in LacZ gene) | Amp |
| pGFF170 | | pGFF157 | mucAdelta<br>(P. alcaliphila<br>GFF238) | knockout vector; cloned mucA seamless knockout construct (GFF238) into SmaI site in pGFF157 by isothermal assembly of partGFF30 & 31 (5prime 715 nt plus 3prime 714 nt); Orientation is forward in vector (reverse in LacZ gene) | Amp |
| pGFF171 | | pGFF157 | mucAdelta<br>(P. toyotomiensis<br>GFF248) | knockout vector; cloned mucA seamless knockout construct (GFF248) into SmaI site in pGFF157 by isothermal assembly of partGFF32 & 33 (5prime 715 nt plus 3prime 714 nt); Orientation is forward in vector (reverse in LacZ gene) | Amp |

TABLE 8-continued

DNA plasmid vectors

| Plasmid Name | Alternative name | Vector backbone | Insert--Gene | Notes | E. coli marker |
|---|---|---|---|---|---|
| pGFF173 | | pGFF157 | mucAdelta (*P. aeruginosa* PAO1) | knockout vector, cloned mucA seamless knockout construct (GFF233) into SmaI site in pGFF157 by isothermal assembly of partGFF28&29 product (5prime 716 nt plus 3prime 716 nt); Orientation is forward in vector (reverse in LacZ gene) | Amp |
| pGFF174 | | pGFF157 | pslDdelta (*P. aeruginosa* PAO1) | knockout vector; cloned pslD seamless knockout construct (GFF233) into SmaI site in pGFF157 by isothermal assembly of PCR products prGFF695/697 & prGFF696/698 (5prime 525 nt plus 3prime 527 nt); Orientation is forward in vector (reverse in LacZ gene) | Amp |
| pGFF175 | | pGFF157 | pelFdelta (*P. aeruginosa* PAO1) | knockout vector; cloned pelF seamless knockout construct (GFF233) into SmaI site in pGFF157 by isothermal assembly of PCR products prGFF699/700 & prGFF701/702 (5prime 480 nt plus 3prime 497 nt); Orientation is forward in vector (reverse in LacZ gene) | Amp |

TABLE 9

Strains

| Strain name | Species | Strain Background | Plasmid Name | Insert--Gene | Genotype |
|---|---|---|---|---|---|
| GFF233 | *Pseudomonas aeruginosa* PAO1 | ATCC BAA-47 | | | |
| GFF238 | *Pseudomonas alcaliphila* | DSM 17744; AL15-21 | | | |
| GFF248 | *Pseudomonas toyotomiensis* | JCM15604 | | | |
| GFF257 | *Pseudomonas toyotomiensis* | GFF248; JCM15604 | pGFF80 | | |
| GFF373 | *Bacillus subtilis* | BGSC 1A1; 168 | | | |
| GFF374 | *Bacillus subtilis* | BGSC 3A1; NCIB3610 | | | |
| GFF375 | *Pseudomonas alcaliphila* | GFF238; DSM17744 | pGFF155 | gumABCDEFGHIJKLM (*X. campestris*) | |
| GFF377 | *Pseudomonas toyotomiensis* | GFF248; JCM15604 | pGFF155 | gumABCDEFGHIJKLM (*X. campestris*) | |
| GFF390 | *Pseudomonas stutzeri* | ATCC PTA-8823; LH4:15 | | | |
| GFF419 | *Pseudomonas alcaliphila* | GFF238; DSM17744 | | | mucAdelta |

Example 9

Isolating and Screening Biosurfactant and Biopolymer Producing Alkaliphilic Microbes from Mono Lake 1. Isolation of Biosurfactant and Biopolymer Producing Microbes from Mono Lake Water samples were collected at Marina Beach, Navy Beach and South Tofa, as well as Hot Springs on Paoha Island of Mono Lake using plastic bottles, wrapped in foil and stored in an ice containing cooler. YCAB10, a pH 10 artificial medium similar to the chemistry of Mono Lake water, containing 0.7% boric acid, 5% NaCl, 2% NaHCO3 was prepared and filtered (0.2 µM) sterile. 100 µL of each Mono Lake water sample was spread on YCAB10 agar plates, incubated at 30-50 C for 16 hours. Large colonies formed by various fast growing microbes were transferred to new fresh plates for screening biosurfactant production microbes. After 16 hours' incubation at 30 C, a thin layer of Paraffin oil was sprayed onto the plates using an airbrush (Central Pneumatic Oil-less Air brush Compressor kit model

95630 sold by Harbor Freight Tools). A microbial colony surrounded by uniform round droplets of Paraffin oil suggested that the microbe secreted biosurfactant, which migrated outward from the colony and changed the chemistry around it on plate. Biosurfactant secreting colonies were chosen and cultured in YCAB10 liquid medium, surfactant production was further confirmed by oil spreading, i.e., a drop of culture on a thin layer of petroleum formed on top of water in a petri dish. A drop of surfactant containing culture would replace an area of the petroleum layer. In addition, biosurfactant was isolated from cultures by acid precipitation, i.e. the culture supernatant was adjust to pH2.0 by hydrochloric acid, the biosurfactant was precipitated by centrifugation at 12,000 g for 15 min, quantified, analyzed by HP LC-mass spectrometry.

In water flooding or MEOR, biosurfactant increases oil recovery by emulsifying petroleum components and enhancing the interaction of oil and water. Biopolymer is another critical component in microbial enhanced oil recovery (MEOR). Biopolymer increases oil recovery by increasing the viscosity of the flooding fluid. Therefore, an ideal microbe applied in microbial enhanced oil recovery should be able to produce either biosurfactant or biopolymer, or produce both of them in situ. Mucoid colony phenotype was typical for a microbe capable of producing biopolymer. To isolate microbes able to produce biosurfactant and biopolymer, biosurfactant producing colonies selected above were placed on YACB10 agar plates, mucoid colonies were biopolymer producing microbes and chosen for further characterization and penetration laboratory testing.

Biopolymer produced by microbes in culture can also increased the viscosity of the culture. To test microbial biopolymer production, candidate colonies were cultured in YCAB10 medium, the culture viscosity was measured using a No. 2 A627 viscometer tube, suggested those isolated alkaliphilic microbes from Mono Lake did produce biopolymer, increased the viscosity of the culture two to three fold. Biopolymers was isolated from the cultures, and dissolved in an appropriate solution, to quantitatively analyzed the viscosity of the biopolymer.

After a series of screening processes, more than a hundred microbial isolates were isolated from Mono Lake. Some of these isolates are facultative anaerobes, able to grow in the absence of oxygen if nitrate is supplied. Some of isolates from Hot Springs in Paoha Island were able to grow at 55 C.

16S rRNA gene sequences were PCR amplified and sequenced from these alkaliphilic microbes isolated from Mono Lake. Sequences analysis and BLAST search revealed that microbes isolated from Mono Lake beach belonged to *Halomonas* genus, while those isolated from hot springs of Paoha Island were in genus *Bacillus* such as *Caldalkalibacillus uzonensis* and *Bacillus halodurans*. The 16S rDNA gene sequences data is provided as FASTA format in Table 10.

TABLE 10

Alkaliphilic Isolates 16S rDNA

| Isolate | Species | SEQ ID NO: | Sequence |
|---|---|---|---|
| ML2-9 16S rDNA (1170 bp) | Halomonas campisalis | 87 | GGGGATAACCTGGGGAAACCCAGGCTAATACCGCATAC GTCCTACGGGAGAAAGCAGGGGATCTTCGGACCTTGCG CTATCGGATGAGCCCATGTCGGATTAGCTTGTTGGTGA GGTAATGGCTCACCAAGGCGACGATCCGTAGCTGGTCT GAGAGGATGATCAGCCACATCGGGACTGAGACACGGCC CGAACTCCTACGGGAGGCAGCAGTGGGGAATATTGGAC AATGGGCGAAAGCCTGATCCACTCCATGCCGCGTGTGT GAAGAAGGCCCTCGGGTTGTAAAGCAGTTTCAGTGGGG AAGAAAGCCTTGAGGTTAATACCTTCGAGGAAGGACAT GACCCACAGAAGAAGCACCGGCTAACTCCGTGCCAGCA GCCGCGGTAATACGGAGGGTGCGAGCGTTAATCGGAAT TACTGGGCGTAAAGCGCGCGTAGGCGGTCTGATAAGCC GGTTGTGAAAGCCCCGGGCTCAACCTGGGAACGGCATC CGGAACTGTCAGGCTAGAGTGCAGGAGAGGAAGGTAGA ATTCCCGGTGTAGCGGTGAAATGCGTAGAGATCGGGAG GAATACCAGTGGCGAAGGCGGCCTTCTGGACTGACACT GACGCTGAGGTGCGAAAGCGTGGGTAGCAAACAGGATT AGATACCCTGGTAGTCCACGCCGTAAACGATGTCGACT AGCCGTTGGGGTCCTTGAGACCTTTGTGGCGCAGTTAA CGCGATAAGTCGACCGCCUGGGGAGTACGGCCGCAAGG TTAAAACTCAAATGAATTGACGGGGGCCCGCACAAGCG GTGGAGCATGTGGTTTAATTCGATGCAACGCGAAGAAC CTTACCTACCCTTGACATCGAGAGAACTTGGCAGAGAT GCCTTGGTGCCTTCGGGAACTCTCAGACAGGTGCTCCA TCTGCTGTCGTCAGCTCGTGTTGTGAAATGTTGGGTTA AGTCCCGTAACGAGCGCAACCCTTGTCCTTATTTGCCA GCGCGTAATGGCGGGAACTCTAAGGAGACTGCCGGTGA CAAACCGGAGGAAGGTGGGGACGACGTCAAGTCATCAT GGCCCTTACGGGTAGGGCTACACACGTGCTACAATGGA CGGTACAAAGGGTTGCAAAGCCGCGAGGTGGAGCTAAT CCCATAAAGCTGTTCTCAGTCCGGATCGGAGT |
| HS2 16S rDNA (783 bp) | Caldalkalib acillus uzonensis | 88 | AGCCTGATGGAGCACGCCGCGTGAGCGAGGAAGGTCTT CGGATTGTAAAGCTCTGTTGTTAGGGAAGAACAAGTGT CGTTCGAATAGGGCGGCACCTTGACGGTACCTAACGAG AAAGCCCCGGCTAACTACGTGCCAGCAGCCGCGGTAAT ACGTAGGGGGTCGAGCGTTGTCCGGAATTATTGGGCGT AAACTCGCGCGCAGGCGGTCTCTTAAGTCTGATGTGAA AGCCCACGGCTCAACCGTGGAGGGTCATTGGAAACTGG GAGACTTGAGTGCAGGAGAGGGAAGCGGAATTCCACGT |

TABLE 10-continued

Alkaliphilic Isolates 16S rDNA

| Isolate | Species | SEQ ID NO: | Sequence |
|---|---|---|---|
| | | | GTAGCGGTGAAATGCGTAGAGATGTGGAGGAACACCAG TGGCGAAGGCGGCTTCCTGGCCTGTAACTGACGCTGAG GCGCGAAAGCGTGGGGAGCGAACAGGATTAGATACCCT GGTAGTCCACGCCGTAAACGATGAGTGCTAGGTGTTGG GGGTTTCAACACCCTCAGTGCTGAAGTTAACACATTAA GCACTCCGCCTGGGGAGTACGGCCGCAAGGCTGAAACT CAAAGGAATTGNCGGGGGCCCGCACAAGCGGTGGAGCA TGTGGTTTAATTCGAAGCAACGCGAAGAACCTTACCAG GACTTGACATCCTCTGACCGCCCTAGAGATAGGGTCTT CCCCTTCGGGGGACAGAGTGACAGGTGGTGCATGGTTG TCGTCAGCTCGTGTCGTGAGATGTTGGGTTAAGTCCCG CAACGACCGCAACCCTTGACCTTAGTTGCCAGCATTCA GTTGGGCACTCTAAGGTGACTGCC |
| HS9 16S rDNA (1168 bp) | Bacillus halodurans 99% match | 89 | TATACAAGGAAAGGCCGCTGAAAAGCGACCTCTTTTTT CATCAATCAATGTCCAGAGGCCTTGTACACNCCGCCCC NNGGTTTCGGCTATCACTTACAGATGGGCCCGCGGCGC ATTAGCTAGTTGGTGAGGTAACGGCTCACCAAGGCAAC GATGCGTAGCCGACCTGAGAGGGTGATCGGCCACACTG GGACTGAGACACGGCCCAGACTCCTACGGGAGGCAGCA GTAGGGAATCTTCCGCAATGGACGAAAGTCTGACGGAG CAACGCCGCGTGAGTGATGAACGTTTTCGGATCGTAAA ACTCTGTTGTTAGGGAAGAACAAGTGCCGTTCGAAAGG GCGGCACCTTGACGGTACCTAACGAGAAAGCCACGGCT AACTACGTGCCAGCAGCCGCGGTAATACGTAGGTGGCA AGCGTTGTCCGGAATTATTGGGCGTAAAGCGCGCGCAG GCGGTCTCTTAAGTCTGATGTGAAAGCCCCCGGCTCAA CCGGGGAGGGTCATTGGAAACTGGGAGACTTGAGTACA GAAGAGCAGAGTGGAATTCCACGTGTAGCGGTGAAATG CGTAGAGATGTGGAGGAACACCAGTGGCGAAGGCGACT CTCTGGTCTGTAACTGACGCTGAGGCGCGAAAGCGTGG GGAGCAAACAGGATTAGATACCCTGGTAGTCCACGCCG TAAACGATGAGTGCTAGGTGTTAGGGGTTTCGACGCCT TTAGTGCCGAAGTTAACACATTAAGCACTCCGCCTGGG GAGTACGACCGCAAGGTTGAAACTCAAAGGAATTGACG GGGGCCCGCACAAGCAGTGGAGCATGTGGTTTAATTCG AAGCAACGCGAAGAACCTTACCAGGTCTTGACATCCTT TGACCACCCTAGAGATAGGGCTTTCCCCTTCGGGGGAC AAAGTGACAGGTGGTCTCATGGTTGTCGTCAGCTCGTG TCGTGAGATGTTGGGTTAAGTCCCGCAACGAGCGCAAC CCTTGACCTTAGTTGCCAGCATTCAGTTGGGCACTCTA AGGTGACTGCCGGTGACAAACCGGAGGAAGGTGGGGAT GACGTCAAATCATCATGCCCCTTATGACCTGGGCTACA CACGTGCTNCTCNGGCNTAACACANGNANTCGAAGCCG CGAAGGNGCANCCGATACCTNAAAGCCCT |
| BF1 16S rDNA (1395 bp) | Idiomarin sp | 90 | GAGGGTTAAGCTATCTACTTCTGGTGCAGCCCACTCCC ATGGTGTGACGGGCGGTGTGTACAAGGCCCGGGAACGT ATTCACCGTGGCATTCTGATCCACGATTACTAGCGATT CCGACTTCACGGAGTCGAGTTGCAGACTCCGATCCGGA CTACGACGCGCTTTTTGAGATTCGCTTGCTATCGCTAG CTTGCTGCCCTTTGTGCGCGCCATTGTAGCACGTGTGT AGCCCATCCCGTAAGGGCCATGATGACTTGACGTCGTC CCCACCTTCCTCCGGTTTATCACCGGCAGTCTCCCTAG AGTTCCCACCATTACGTGCTGGCAACTAAGGATAAGGG TTGCGCTCGTTGCGGGACTTAACCCAACATCTCACAAC ACGAGCTGACGACAGCCATGCAGCACCTGTCTCAGAGT TCCCGAAGGCACTAATCCATCTCTGGAAAATTTTCTGG ATGTCAAGGGATGGTAACTGTTCTTCGCGTTGCATCGA ATTAAACCACATGCTCCACCGCTTGTGCGGGCCCCCGT CAATTCATTTGAGTTTTAACCTTGCGGCCGTACTCCCC AGGCCCTTCAACTTAGTGCGTTAGCTGCGTTACTCACA TCATAATGACACGAACAACTAGTTGACATCGTTTACGG CGTGGACTACCAGGGTATCTAATCCTGTTTGCTCCCCA CGCTTTCGCTCCTCAGCGTCAGTTTTTGACCAGGTGGC CGCCTTCGCCACTGGTATTCCTTCCAATATCTACGCAT TTCACCGCTACACTGGAAATTCTACCACCCTCTTCAAA ACTCTAGCCTGCCAGTTCAAAATGCTATTCCAAGGTTG AGCCCTGGGCTTTCACATCTTGCTTAACAGGCCGCCTA CGTGCGCTTTACGCCCAGTAATTCCGATTAACGCTCGC ACCCTCCGTATTACCGCGGCTGCTGGCACGGAGTTAGC CGGTGCTTCTTCTGTGGCTAACGTCAATCCTTTGCCGC TATTAACGACAACGCCTTCCTCACCACTGAAAGTGCTT TACAACCCGAAGGCCTTCTTCACACACGCGGCATGGCT GGATCAGGCTTGCGCCCATTGTCCAATATTCCCCACTG |

TABLE 10-continued

Alkaliphilic Isolates 16S rDNA

| Isolate | Species | SEQ ID NO: | Sequence |
|---|---|---|---|
| | | | CTGCCTCCCGTAGGAGTCTGGGCCGTGTCTCAGTCCCA |
| | | | GTCTTGGCTGATCATCCTCTCAGACCAGCTAGAGATCG |
| | | | TCGCCTTGGTGAGCCATTACCTCACCAACTAGCTAATC |
| | | | TCGCTTGGGTTCATCTGATGGCGTATGGCCCGAAGGTC |
| | | | CCATACTTTGCTCCGAAGAGATTATGCGGTATTAGCCA |
| | | | CCGTTTCCAGTGGTTGTCCCCGCCATCAGGCAGATCC |
| | | | CCAAGTATTACTCACCCGTCCGCCGCTCGTCATCATCT |
| | | | AGCAAGCTAGATATGTTACCGCTCGACTGCA |

2. Isolation of Alkaliphilic Ultramicrobacteria (≤0.2 µM) from Mono Lake

To isolate ultramicrobacteria (≤0.2 µM), Mono Lake water was collected in September from Marina Beach. The water was filtered by a 0.2 µM filter to remove any particles and microbes larger than 0.2 micron. The filtered water was spread on YCAB10 agar plates, and incubated at 30 C for 72 hours. Two types of colonies, mucoid and non-mucoid, were isolated. The 16S ribosomal RNA gene of mucoid ultramicrobe was amplified using universal primers, and 16 rRNA gene sequences were obtained. 16S RNA Gene sequences analysis using BLAST and BioEdit, identified the isolated ultramicrobacteria was similar to gamma-proteobacteria *Alteromonadales* bacterium and *Idiomarina* sp. To isolate additional ultramicrobacteria slightly larger than 0.2 micron, membrane filter with 0.45 µM pores was also used to filter Mono lake water, the same procedure described above was used and a number of colonies were isolated. However, 16S RNA sequences analysis suggested they were identical with those ultramicrobacteria isolated from 0.2 µM filtered Mono Lake water, belonged to genus *Idiomarina*.

3. Sandpack Column and Berea Sandstone Core Penetration of Microbes Isolated from Mono Lake The alkaliphilic microbes isolated from Mono Lake were cultured, and used for sand pack columns and Berea sandstone columns penetration tests. A number of strains of *Bacillus* and *Pseudomonas* obtained from microbial collection center were used as control, such as biosurfactant producing *Bacillus mojavensis* JF-2, biofilm producing *Bacillus subtilis* 3610, alkaliphilic *B. circulans*, and *P. stutzeri*. All these microbes were able to penetrate sand pack column, the recovery rate of these microbes varied, ranging from 5% (ML2-9) to 95% (*Bacillus mojavensis* JF-2).

Additionally, our penetration experiments showed that starved cells, vegetative cells or spores of these microbes were unable to penetrate low permeability Berea Sandstone Core (~50 mili Darcy). However, they were able to penetrate high permeability Berea Sandstone Core (>100 mili Darcy), viable cells were recovered at elute at 5% (*Bacillus* JF-2 starved cells) to 6% (*Bacillus mojavensis* JF-2 spores). The control Sand Stone Core penetration experiments showed that about 80% was recovered for ultramicrobacterium *Sphingomonas alaskensis*, and about 50% for Mono Lake isolate gamma-proteobacterium BF1 (*Idiomarin* sp).

The alkaliphilic microbial cultures were also used to recover the residual oils in sandpack cells and columns. In comparison with control microbe *Bacillus* and *Pseudomonas* culture, alkaliphilic microbial cultures recovered residual oil 15-50% more than that recovered by the control microbes.

The penetration of microbes through the formation or sandstones remains as an unsolved problem, a challenge and an obstacle for MEOR application. To test the penetration of ultramicrobacteria in sand stone cores, Berea Sandstone cores (purchased from Cleveland Quarries 5270 Devon Dr. Vermilion, Ohio 44089 with estimated permeability in the range of 50 to 1000 mD) and Stone Cores from oil field in New Mexico (a gift from HEYCO Energy Group Inc. permeability estimated less than 50 mD) were used for ultramicrobacterial penetration test. Three pore volumes of sterile water were flooded through the cores, followed by flooding Mono Lake Water filtered by 0.2 micron filter and untramicrobacteria cultures. To check untramicrobacterial capability to penetrate the stone cores, elutes were collected and spread on agar plates. Our results showed that after 10 to 12 pore volume flooding, the Alkaliphilic untramicrobacteria isolated from Mono Lake penetrated the stone cores, and the recovered rate of viable cells was around 2%, suggesting the untramicrobacteria was able to penetrate Berea sandstones and the formation from oil field.

The invention claimed is:

1. A method of enhancing oil recovery, the method comprising:
   (a) introducing into an oil reservoir a microorganism capable of growing in an environment of a waterflood drive fluid;
   wherein said oil reservoir comprises indigenous bioplug-forming microorganisms; and
   wherein said microorganism is genetically modified (i) to be deficient in its ability to produce a flow-restricting bioplug and (ii) to produce soluble cell free biopolymers in situ within the oil reservoir; and
   (b) water-flooding said reservoir with a waterflood drive fluid having a pH or a temperature that kills or suppresses the growth of said indigenous bioplug-forming microorganisms to reduce the concentration of said indigenous bioplug-forming microorganisms in the oil reservoir.

2. The method of claim 1 wherein the oil reservoir is selected from the group consisting of underground reservoirs, producing wells, non-producing wells, experimental wells, exploratory wells, oil sands and other sources of heavy oil.

3. The method of claim 1 wherein the microorganism is an archaeon or a bacterium.

4. The method of claim 1 wherein the microorganism is present in a culture of microorganisms comprising a plurality of microorganisms that are genetically modified to be deficient in their ability to produce said flow-restricting bioplug, and to produce said soluble cell free biopolymers in situ within the oil reservoir.

5. The method of claim 4 wherein said microorganism is present in a culture of microorganisms comprising a plurality of microorganisms that are able to produce surfactants.

6. The method of claim 1 wherein said microorganism is able to produce surfactants.

7. The method of claim 1 wherein said microorganism is able to utilize simple carbons selected from the group comprising glucose, sucrose, mannose, starch, glycerin, organic acids, and other simple sugars.

8. The method of claim 1 wherein said soluble cell free biopolymers comprise a polysaccharide.

9. The method of claim 1 wherein said microorganism is further characterized by (i) containing functional genes for carbohydrate metabolism and conversion of carbohydrates into high molecular weight polysaccharides; (ii) lacking functional genes for formation of a biofilm; (iii) containing functional genes for production of surfactants; and (iv) being regulated to express the functional genes of steps (i) and (iii), and grow in the waterflood drive fluid.

10. The method of claim 1 further comprising a step of injecting a nutrient mixture into said reservoir.

11. The method of claim 1, wherein said microorganism is further naturally deficient in its ability to produce said flow restricting bioplug.

12. The method of claim 1, wherein said microorganism is selected for its ability to penetrate 0.2 μm filters or sandstone cores of 50 mD or less permeability.

13. The method of claim 1, wherein the pH of the waterflood drive fluid is alkaline.

* * * * *

SEQUENCE LISTING

<160> NUMBER OF SEQ ID NOS: 90

<210> SEQ ID NO 1
<211> LENGTH: 749
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
cctgttatcc ctacccatc tggtggcgcg cggcagacgc ccgccggata gtgatgtgag    60
ttccgaggac gccgagtttt atgagggcga tcacgctctc aaggacatcg agtcaccgga   120
```

```
acgctcgctg ctcagggatg agattgaaga taccgttcat cgaaccattc aacttttgcc      180
agaagatttg cgtacggctc taacactgcg tgaatttgat ggtcttagtt atgaagacat      240
tgcgagcgtc atgcagtgtc cggtgggcac agtgcgttcc cggatcttcc gggcacgtga      300
agccatagat aaagcattgc aacccttgtt gcatgaatcc tgagacagcg cgacagcca       360 agagaggaac cgccggagaa acatgcgcgt attaccgctg tatgtggtga tgggggggctg     420 gctatcgatg ccggcccttg ctgctgatgc cgggtcctgg atggagcgac ttgcggcggc      480
agagcagaaa cagagttata ccggtacgtt cgtctacgaa cgcaatggca gcttttccag      540
tcatgccgtt tggcagcagg tcgaagaagg tcaagtgcag gagcgattgc ttcagcttga      600
cggagctccg gctgaagttc tgctggtaaa tggtcagatg caatgcgcta ccgatgacct      660
cgcggcgcaa gtgcgtgaag cgcaggcttg gcacgggcag cgtctcgatc cgaaaagcact    720 ctccgagtgg tagggattac cctgttatc                                        749

<210> SEQ ID NO 2
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
cctgttatcc ctacccgggc gcatgcttgg aggggagaac ttttgcaaga agcccgagtc      60
tatcttggca agacgattcg ctgggacgct cgaagctcct ccaggttcga agaggagctt      120
tcatgctaac ccaggaacag gatcagcaac tggttgaacg ggtacagcgc ggagacaagc      180
gggctttcga tctgctggta ctgaaatacc agcacaagat actgggattg atcgtgcggt      240
tcgtgcacga cgcccaggaa gcccaggacg tagcgcagga agccttcatc aaggcatacc      300
gtgcgctcgg caatttccgc ggcgatagtc ttttttatac ctggctgtat cggatcgcca      360
tcaacaccgc gaagaaccac ctggtcgctc gcgggcgtcg gccaccggac agcgatgtga     420
ccgcagagga tgcggagttc ttcgagggcg accacgccct gaaggacatc gagtcgccgg     480
aacgggcgat gttgcgggat gagatcgagg ccaccgtgca ccagaccatc cagcagttgc     540
ccgaggattt gcgcacggcc ctgaccctgc gcgagttcga aggtttgagt tacgaagata     600
tcgccaccgt gatgcagtgt ccggtgggga cggtacggtc gcggatcttc cgcgctcgtg     660
aagcaatcga caaagctctg cagcctttgt tgcgagaagc ctgacacagc ggcaaatgcc     720
aagagaggta tcgctggaga gacatgcgca                                      750

<210> SEQ ID NO 3
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
caagagaggt atcgctggag agacatgcgc accacctccc tgttgctttt gcttggcagc      60
ctgatggcgg ttcccgccac tcaggctgcc gacgcttccg actggctgaa tcgtctcgcc      120
gaggccgatc gccagaacag tttccaaggc accttcgtct acgagcgcaa tggcagcttc      180
tccacccatg agatctggca tcgcgtggag agcgatggtg cggttcgcga gcgcctgctc      240
```

| | |
|---|---|
| cagctcgacg gcgcgcgcca ggaagtggtc cgggtcgacg ggcgcaccca gtgcatcagc | 300 |
| ggcggccttg ccgaccaact ggccgatgcc cagctgtggc cggtgcgcaa gttcgatccc | 360 |
| tcccagctgg cttcctggta cgacctgcgc ctggtcggcg aatcccgtgt cgccggccgc | 420 |
| ccggcagtgg tccttgcggt gactccgcgc gaccagcatc gctacggctt cgagctgcac | 480 |
| ctggaccgcg acaccggcct gccgttgaag tcgctgctgc tgaacgagaa ggggcagttg | 540 |
| ctcgagcgct tccagttcac ccagttgaat accggcgcgg cacctgccga agaccagttg | 600 |
| caggcgggcg ccgaatgcca ggtcgtcggc ccggccaagg ccgacggcga agaccgtg | 660 |
| gcctggcgct cggaatggct gccgccaggt ttcaccctga cccgcagttt catgcgtcgc | 720 |
| agtccggtca cccgggatta ccctgttatc | 750 |

<210> SEQ ID NO 4
<211> LENGTH: 749
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---|
| cctgttatcc ctacccggga gcttgcttgg aggggagaac ttttgcgtaa gacccgagtc | 60 |
| tatcttggca agctgattcg cttacgggcg caagcctcct ccaagcgtta cgaggagaat | 120 |
| gcatgctaac ccaggaagat gatcagcaac tggtcgagcg agtgcagcgt ggtgacaagc | 180 |
| gtgccttcga tctgttggtg ctgaagtatc agcacaagat cctcggtctg atcgtgcgat | 240 |
| tcgtgcacga cacccacgag gctcaggatg tcgctcagga ggcgttcgta aaagcctacc | 300 |
| gagcgcttgg aaactttcgc ggtgacagtg cgttctatac atggctgtac cgcatcgcca | 360 |
| tcaacacggc gaagaattat ctggtgtccc gcggtcggcg gccgccagat agtgatgtca | 420 |
| gtagcgatga cgcggagttc tatgatggcg atcacggcct caaggacatc gagtcaccgg | 480 |
| agcgggcatt gctgcgcgac gagatcgaag ccaccgtgca tcgaaccatc gcccaactgc | 540 |
| cggatgattt cgcacggcc ctgaccctgc gtgagttcga aggcttgagt tacgaggaca | 600 |
| ttgcaggcgt catgcaatgc ccggtaggca cggtgcgttc gcggatattc cgtgcacgtg | 660 |
| aggcaattga taagtccctg caacctctgt tgcaggaaac ctaaggcagc ggcgacagcc | 720 |
| aagagaggaa caccgcgcta aggagtcac | 749 |

<210> SEQ ID NO 5
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---|
| ccaagagagg aacaccgcgc taaggagtca catgcgcgcg attcccctct accttctcgg | 60 |
| tggtctgctg gcgttgccgg ttcaggcctc cgaggtgcag gacctgctcg ggcgtctcgc | 120 |
| tgcggcggag cgccagcaaa gcttccaggg cacgttcatc tatgagcgta atgggagttt | 180 |
| ttctacccat gccgtgtggc atcgggtgga ggaggggggc gcagttcgcg aacgccttct | 240 |
| gcaactcgat gggcctgctc aggaagtgct gaaagtcgat ggtcaggctc agtgcgtcac | 300 |
| tggcgcgttg gccgaccagg tcagtgaagg gcaggcatgg cctgctcgcc agctggatgc | 360 |
| cgagcaactg agcgactggt atgacattcg tgtcgctggc aagtcgcgca ttgccaatcg | 420 |

```
tccagcggtc gttctggtgt tggcccccaa ggaccagcat cgctacggct tcgaattgca      480
tctggatcgt gagaccgggc tgccgctgaa gtccctgctg ttgaacgagc gcggccagct      540
tctggaacgc ttccagttcg cccaactgga tacttctgta ccggctgaaa atgccatgca      600
gcctagctcc agctgcaggc cggtgcggtt ccgcgctgcc gacagcatgg acgaaggcag      660
ttggcgatcc gactggttgc cgccgggttt cactctgacc actgcgcagg tgcgtcgcgg      720
gcctgccgct cccgggatta ccctgttatc                                      750
```

`<210>` SEQ ID NO 6
`<211>` LENGTH: 749
`<212>` TYPE: DNA
`<213>` ORGANISM: Artificial Sequence
`<220>` FEATURE:
`<223>` OTHER INFORMATION: Description of Artificial Sequence: Synthetic polynucleotide

`<400>` SEQUENCE: 6

```
cctgttatcc ctacccggga gcttgcttgg aggggagaac ttttgcgtaa gacccgagtc       60
tatcttggca agctgattcg cttacgggcg cagacctcct ccgagcgtta tgaggagagt      120
gcatgctaac ccaggaagat gatcagcagc tggtcgagcg agtgcagcgc ggtgacaagc      180
gtgccttcga tctgttggtg ctgaagtatc agcacaagat cctcggtttg atcgtgcgat      240
tcgtgcacga cacccacgag gctcaggatg tcgctcagga ggctttcgta aaagcctacc      300
gagcgcttgg aaactttcgc ggtgacagcg cgttctatac atggctgtac cgcatcgcca      360
tcaacacggc gaagaattat ctggtgtcac gcggtcggcg gccgccagat agtgatgtca      420
gtagcgatga cgcggagttc tatgacggcg accacggcct gaaggacatc gagtcaccgg      480
agcgggcatt gctgcgcgac gagatcgaag ccaccgtgca tcgaaccatc gcccagttgc      540
cggatgattt gcgcacggcc ctgaccttgc gtgagttcga aggcttgagt tacgaggaca      600
ttgccggcgt catgcagtgt ccggtaggta cggtgcgttc gcggatcttc cgtgcgcgtg      660
aggcaattga taagtccctg cagcctctgt tgcaggaaac ctaaggcagc ggcgacagcc      720
aagagaggaa caccgcgcta aggagtcac                                       749
```

`<210>` SEQ ID NO 7
`<211>` LENGTH: 750
`<212>` TYPE: DNA
`<213>` ORGANISM: Artificial Sequence
`<220>` FEATURE:
`<223>` OTHER INFORMATION: Description of Artificial Sequence: Synthetic polynucleotide

`<400>` SEQUENCE: 7

```
ccaagagagg aacaccgcgc taaggagtca catgcgcgcg attccctct accttctcgg        60 tggtctgctg gcgttgccgg ttcaggccac tgaggtgcaa gacttgctcg ggcgcctcgc      120
tgcggcagag cgccagcaaa gcttccaggg cacgttcatc tatgagcgca atggaagttt      180
ttccacccat gccgtgtggc atcgggtaga ggagggggc gaagttcgcg agcgccttct      240
gcagctcgat gggcctgccc aggaggtgct gaaagtcgat ggccaggctc agtgcgtcac      300
tggcgcgttg gctgaccagg tcagtgaagg gcaggcttgg cctgctcgtc agttggctgt      360
cgagcaattg agcaactggt atgacattcg tgtcgtgggt cagtcgcgca tagccaatcg      420
tccggcagtc gttctggtgc tggcgcccaa ggaccagcat cgctacggct tcgaattgca      480
tctggaccgg gagaccggtc tgccgttgaa atccctcctg ttgaacgagc gtggccagct      540
```

```
actggagcgc ttccagttcg ctcagctgga tacctctgta cccgttgagg atgccatgca        600
gccgagttcg agctgcaggc cggtgcgttt tcgtgctgcc gacagcatgg ccgaaggtac        660
ctggcgatcc gactggctgc cgccgggctt tactctgact actgcgcagg tacgccgcgt        720
gccttccgct cccgggatta ccctgttatc                                         750
```

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caggcctaac acatgaagtc                                                     20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggcggwgtg tacaaggc                                                       18

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaattcctgc agcccaaatg aggcggtaac aggggat                                  37

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcggtggcgg ccgctctaga ccttgctgac cttccacag                                39

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcagcatac agataaaaac tgcc                                                24

<210> SEQ ID NO 13
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 13
ggtaagctcc ccttttattg aatga                                        25

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
taacagcaaa aaaaagagac ggccca                                       26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tattgtcact aggtcttcac ctagtc                                       26

<210> SEQ ID NO 16
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgatataaaa tcattcaata aaggggagc ttaccttcaa caaacgggat tgacttttaa   60
aaaag                                                              65

<210> SEQ ID NO 17
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tatgaatact gggccgtctc tttttttgc tgttagtcgg gaaacctgtc gtgccag      57

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggcggttcct ctcttggctg tcgcc                                        25

<210> SEQ ID NO 19
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 19
ttagggagaa acatgcgcgt a                                                     21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttgcaggata gcttgctagg a                                                     21

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gctcgtgcgg ccagcatgga aga                                                   23

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tccagcgcaa cgacccgccc                                                       20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctggaagtgt tggctcatgt c                                                     21

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agtctatctt ggcaagctga ttc                                                   23

<210> SEQ ID NO 25
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 25
gtgagttcga aggcttgagt tac                                          23

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcttctccgg tactctcggt a                                            21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtgctgaaag tcgatggtca g                                            21

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctgaaaggt cgcgtcgt                                                18

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
taatcttatc gccgctcatt tcc                                          23

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgtcatagaa ctccgcgtca t                                            21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gcttccattg cgctcataga tg                                              22

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cggatcgcca ggtaccttc                                                  19

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctcgagcgcc actacacg                                                   18

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttgctggcc gggcgcatcg c                                               21

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gggccggaac tgatcaggcc ggc                                             23

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gagggaacct ggccctatgt                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttcgtcaatt acttctggac          20

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcgaccagct cgcgacacga gcc          23

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcgatgccat tggggatcac c          21

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctgtcggtmg gggagttcga cggc          24

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cagggctacg ccggcctgtt cct          23

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaggcgaacg grtcgaggat ccagcg          26

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 43
ggcccgacyt cgccttcgat                                                    20

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atggcgggta taggctttga actg                                               24

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atggcggtgt tcctggtgcg                                                    20

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tcgaactcga gatcgtccag cgc                                                23

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcagcgattg agcatgaagg tttc                                               24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ttgatctgcg cccagccggt gatg                                               24

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
```
ttcaagttcc gctcgatgta c                                            21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
atgcgtcagc ttttgcacgg tag                                          23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcagtaggcc tcgcgggtga aga                                          23

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gacgtgatcg gcagcgagga cgccta                                       26

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cccgaggacg tgatcggcag cga                                          23

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccatctacga gctgacgctg t                                            21

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
agatagaggt cgacgccctc gat                                            23

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cggaatgtac gaatttcgat catg                                           24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgaaaggaac gaatttcgat catg                                           24

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
acaagctcgc catcccgccc gccta                                          25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgcaagcagt accgctacca cccgc                                          25

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cgcaggtgct ccagggccag                                                20

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcccaggtgc ggtagtcctt ggcg                                           24

<210> SEQ ID NO 62
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cctgttatcc ctacccgggc agcaagcgcc tggccgac                              38

<210> SEQ ID NO 63
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
caggaagtgc tccctcatga aacgctgagg agcgacatcg ccatgatag                  49

<210> SEQ ID NO 64
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctatcatggc gatgtcgctc ctcagcgttt catgagggag cacttcctg                  49

<210> SEQ ID NO 65
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gataacaggg taatcccggg gatctccatc accgtcgag                             39

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cctgttatcc ctacccgggc gacgtccgcc tgctggccta c                          41

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
catgcaatct cggtgtgttc ggtcatgtcc                                       30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cgaacacacc gagattgcat gacatggccg                                       30

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gataacaggg taatcccggg ccagcaggat gcgtttgtag g                          41

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
atcaggccgg catacaggta ggc                                              23

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
agcatcacgc tgatgatcga ca                                               22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgctggccta ctcgatgctc ga                                               22

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctggcgcgtt ggtactggga act                                              23

```
<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gtccagaagt aattgacgaa                                                  20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tccttctgac cgccgatgaa                                                  20

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cagcgtctgc tggaaggcag ccag                                             24

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgaatgatca gcaagtggct                                                  20

<210> SEQ ID NO 78
<211> LENGTH: 2563
<212> TYPE: DNA
<213> ORGANISM: Pseudomonas alcaliphila

<400> SEQUENCE: 78
ctggaagtgt tggctcatgt ccgagttccg cgtgaaagcg agccctagta tatagagagg       60
ggcagcggca caatagccag cttatgaccg accgcggtgc tcgggaactt tcttagtcat      120
taaggttcca tagagggtcg cccatataag ggagagcgca tgcgcgtgcc tgcatctgaa      180
gtcagcggag ggtgtggaaa tgagcggcga taagattatt tgcgcgagcg gaaaggttcc      240
gctggcgcca ttccaggcag agggaagaaa actctgcggg aagcttgctt ggaggggaga      300
acttttgcgt aagacccgag tctatcttgg caagctgatt cgcttacggg cgcaagcctc      360
ctccaagcgt tacgaggaga atgcatgcta acccaggaag atgatcagca actggtcgag      420
cgagtgcagc gtggtgacaa gcgtgccttc gatctgttgg tgctgaagta tcagcacaag      480
atcctcggtc tgatcgtgcg attcgtgcac gacacccacg aggctcagga tgtcgctcag      540
gaggcgttcg taaaagccta ccgagcgctt ggaaactttc gcggtgacag tgcgttctat      600
```

| | |
|---|---|
| acatggctgt accgcatcgc catcaacacg gcgaagaatt atctggtgtc ccgcggtcgg | 660 |
| cggccgccag atagtgatgt cagtagcgat gacgcggagt tctatgatgg cgatcacggc | 720 |
| ctcaaggaca tcgagtcacc ggagcgggca ttgctgcgcg acgagatcga agccaccgtg | 780 |
| catcgaacca tcgcccaact gccggatgat ttgcgcacgg ccctgaccct gcgtgagttc | 840 |
| gaaggcttga gttacgagga cattgcaggc gtcatgcaat gcccggtagg cacggtgcgt | 900 |
| tcgcggatat tccgtgcacg tgaggcaatt gataagtccc tgcaacctct gttgcaggaa | 960 |
| acctaaggca gcggcgacag ccaagagagg aacaccatga gtcgtgaaac cctgcaggaa | 1020 |
| tcgctgtccg cggtgatgga taacgaagcg gacgaactgg aactgcggcg tgtgctcgca | 1080 |
| gccagcgagg atggcgagct gcgtggcacc tggtcgcgtt accaggtcgc ccgtgcagcc | 1140 |
| atgcatcgtg aactgttggt gccgcaactg gacatcgcat ctgcggtctc cgcggcgctg | 1200 |
| gccgacgaag ccgttccggc acgcaaggcg ccgatctggc gtagtgtcgg tcgcgtagcc | 1260 |
| gtggcagcat cggtgaccgt tgcagtgctg gcgggtgtgc gcttctacaa tcaggatgac | 1320 |
| ctgagcggcg ctcaactggc ccagcaggag acttctccgg tactctcggt acctcaggtc | 1380 |
| cagggtcctg cactgctcgc tggttacaac agcagcgagg aagccggcga agccgccgaa | 1440 |
| gcaggcactg ccagctggca tgagcagcgc ctgccgaact acctgcgtca acatgcgcag | 1500 |
| gaagccgtga tgggtaccgg tgaaaccgct ctgccttatg ctcgggctgc gagtctggaa | 1560 |
| aaccgctaag cgctaaggag tcacatgcgc gcgattcccc tctaccttct cggtggtctg | 1620 |
| ctggcgttgc cggttcaggc ctccgaggtg caggacctgc tcgggcgtct cgctgcggcg | 1680 |
| gagcgccagc aaagcttcca gggcacgttc atctatgagc gtaatgggag ttttctacc | 1740 |
| catgccgtgt ggcatcgggt ggaggagggg ggcgcagttc gcgaacgcct tctgcaactc | 1800 |
| gatgggcctg ctcaggaagt gctgaaagtc gatggtcagg ctcagtgcgt cactggcgcg | 1860 |
| ttggccgacc aggtcagtga agggcaggca tggcctgctc gccagctgga tgccgagcaa | 1920 |
| ctgagcgact ggtatgacat tcgtgtcgct ggcaagtcgc gcattgccaa tcgtccagcg | 1980 |
| gtcgttctgg tgttggcccc caaggaccag catcgctacg gcttcgaatt gcatctggat | 2040 |
| cgtgagaccg gctgccgct gaagtccctg ctgttgaacg agcgcggcca gcttctggaa | 2100 |
| cgcttccagt tcgcccaact ggatacttct gtaccggctg aaaatgccat gcagcctagc | 2160 |
| tccagctgca ggccggtgcg gttccgcgct gccgacagca tggacgaagg cagttggcga | 2220 |
| tccgactggt tgccgccggg tttcactctg accactgcgc aggtgcgtcg cgggcctgcc | 2280 |
| gctgatgact ccgtcaccta tctgatgtac ggcgatggcc tggtgcgatt ctcggttttt | 2340 |
| ctcgagcctc ttaaaggtcg cgtcgtcgaa gacgcgcgca gtcagttggg tccaaccgtc | 2400 |
| gccgtttcgc gacggatgag caccgatgcg ggtgacgtga tggttaccgt ggtcggtgag | 2460 |
| attcctctgg ggactgccga gcgcatagcc ctgtcgatgc gcgccggagt gcctgaacag | 2520 |
| gctagccaat gatcgaagag caggggcgtg tagtggcgct cga | 2563 |

<210> SEQ ID NO 79
<211> LENGTH: 2540
<212> TYPE: DNA
<213> ORGANISM: Pseudomonas toyotomiensis

<400> SEQUENCE: 79

| | |
|---|---|
| tggctcatgt ccgagttccg cgtgaaagcg agccctagta tatagagagg ggcagcggca | 60 |
| caataggtgg cttatgaccg accgcggtgc tcgggaactt tcttagtcgt taaggttcca | 120 |
| tagagggtcg cccatataag ggagagcgcc tgcgcgtgcc tgcatctgaa gtcagcggag | 180 |

```
ggtgtggaaa tgagcggcga taagattatt tgcgcgagcg gaaaggttcc gctggcgcca    240
ttccaggcag agggaagaaa actctgcggg aagcttgctt ggaggggaga acttttgcgt    300
aagacccgag tctatcttgg caagctgatt cgcttacggg cgcagacctc ctccgagcgt    360
tatgaggaga gtgcatgcta acccaggaag atgatcagca gctggtcgag cgagtgcagc    420
gcggtgacaa gcgtgccttc gatctgttgg tgctgaagta tcagcacaag atcctcggtt    480
tgatcgtgcg attcgtgcac gacacccacg aggctcagga tgtcgctcag gaggctttcg    540
taaaagccta ccgagcgctt ggaaactttc gcggtgacag cgcgttctat acatggctgt    600
accgcatcgc catcaacacg gcgaagaatt atctggtgtc acgcggtcgg cggccgccag    660
atagtgatgt cagtagcgat gacgcggagt tctatgacgg cgaccacggc ctgaaggaca    720
tcgagtcacc ggagcgggca ttgctgcgcg acgagatcga agccaccgtg catcgaacca    780
tcgcccagtt gccggatgat ttgcgcacgg ccctgacctt gcgtgagttc gaaggcttga    840
gttacgagga cattgccggc gtcatgcagt gtccggtagg tacggtgcgt tcgcggatct    900
tccgtgcgcg tgaggcaatt gataagtccc tgcagcctct gttgcaggaa acctaaggca    960
gcggcgacag ccaagagagg aacaccatga gtcgtgaaac cctgcaggaa tcgctgtccg   1020
cggtgatgga taacgaagcg gacgaactgg aactgcggcg tgtgctcgca gccagcgatg   1080
atggcgagct gcgcggcacc tggtcgcgtt accagatcgc ccgtgcagcc atgcatcgtg   1140
agctgttggt gccgcaactg gacatcgcat ctgcggtttc cgcggcgctg gccgacgaag   1200
ccgtcccggc acgcaaggcg ccgatctggc gtagtgtcgg gcgcgtagcc gtcgcagcat   1260
cggtgaccgt tgcagtgctg gcgggtgtgc gcttctacaa tcaggatgac ctgagcggcg   1320
cccaattggc acagcaggag gcttctccgg tactctctgt accgcaggtg caaggtcctg   1380
cgctgctcgc tggttacaac agcagcgagg aagccggcga agccgccgaa gcaggcactg   1440
ccagctggca tgagcagcgt ttgccgaact acctgcgtca acatgcgcag gaagccgtga   1500
tgggtaccgg tgaaaccgct ctgccttatg ctcgggctgc aagtctggaa aaccgctaag   1560
cgctaaggag tcacatgcgc gcgattcccc tctaccttct cggtggtctg ctggcgttgc   1620
cggttcaggc cactgaggtg caagacttgc tcgggcgcct cgctgcggca gagcgccagc   1680
aaagcttcca gggcacgttc atctatgagc gcaatggaag ttttttccacc catgccgtgt   1740 ggcatcgggt agaggagggg ggcgaagttc gcgagcgcct tctgcagctc gatgggcctg   1800
cccaggaggt gctgaaagtc gatggccagg ctcagtgcgt cactggcgcg ttggctgacc   1860
aggtcagtga agggcaggct tggcctgctc gtcagttggc tgtcgagcaa ttgagcaact   1920
ggtatgacat tcgtgtcgtg ggtcagtcgc gcatagccaa tcgtccggca gtcgttctgg   1980
tgctggcgcc caaggaccag catcgctacg gcttcgaatt gcatctggac cgggagaccg   2040
gtctgccgtt gaaatccctc ctgttgaacg agcgtggcca gctactggag cgcttccagt   2100
tcgctcagct ggatacctct gtaccgcgttg aggatgccat gcagccgagt tcgagctgca   2160
ggccggtgcg ttttcgtgct gccgacagca tggccgaagg tacctggcga tccgactggc   2220
tgccgccggg ctttactctg actactgcgc aggtacgccg cgtgccttcc gctgatgatc   2280
ccgtcaccta tctcatgtat ggcgatggcc tggcgcgatt ctcggttttt ctcgaacccc   2340
tgaaaggtcg cgtcgtcgag gatgcacgca gccagctggg cccaaccgtc gcggtttcgc   2400
ggcggatgag taccgactct ggtgacgtca tggtgaccgt ggtgggtgag atccccttgg   2460
ggactgccga acgcatcgcc ctgtccatgc gcgccggagt gcctgaacag gctagccaat   2520
```

```
gatcgaggag cagggscgtg                                              2540
```

<210> SEQ ID NO 80
<211> LENGTH: 913
<212> TYPE: DNA
<213> ORGANISM: Pseudomonas stutzeri
<220> FEATURE:
<221> NAME/KEY: modified_base
<222> LOCATION: (800)..(800)
<223> OTHER INFORMATION: a, c, t, g, unknown or other

<400> SEQUENCE: 80

```
ttgctaggag gggggagaac ttttgcgtaa agcccgggtc tattctggca ggtcggttcg    60
ctggtgtgag cgacgctact ccgctaccga ggaggagcgt tcatgttgac tcaggagcag   120
gaccagcagc tggttgaacg agtgcagcgt ggtgacaagc gggcgtttga tctgctggta   180
atgaaatacc agcacaagat ccttgggttg atcgtgcggt tcgtgcatga ctctcatgaa   240
gctcaggatt tgcccaaga ggcttttatc aaagcctacc gtgcactagc caattttcgc    300
ggtgacagcg ctttctacac ctggctgtac cgcatcgcca tcaatacggc gaagaatcat   360
ctggtggcgc gcggcagacg cccgccggat agtgatgtga gttccgagga cgccgagttt   420
tatgagggcg atcacgctct caaggacatc gagtcaccgg aacgctcgct gctcagggat   480
gagattgaag ataccgttca tcgaaccatt caacttttgc cagaagattt gcgtacggct   540
ctaacactgc gtgaatttga tggtcttagt tatgaagaca ttgcgagcgt catgcagtgt   600
ccggtgggca cagtgcgttc ccggatcttc cgggcacgtg aagccataga taaagcattg   660 caaccettgt tgcatgaatc ctgagacagc ggcgacagcc aagagaggaa ccgccatgag   720
tcgtgaagcc ctgcatgaat cgctgtccgc ggtgatggat aacgaagcgg acgagttgga   780
attacgtcgc atgctcgcan gcgacaaccc ggagctacg gctacctggt cgcgttatca    840
acttgcccgt gccgccatgc acaaggagtt gatcgagccg cgcctggata tcgcttctgc   900
ggtatcggct gcg                                                     913
```

<210> SEQ ID NO 81
<211> LENGTH: 976
<212> TYPE: DNA
<213> ORGANISM: Pseudomonas stutzeri

<400> SEQUENCE: 81

```
cagcatggaa gaacgttagg gagaaacatg cgcgtattac cgctgtatgt ggtgatgggg    60
ggctggctat cgatgccggc ccttgctgct gatgccgggt cctggatgga gcgacttgcg   120
gcggcagagc agaaacagag ttataccggt acgttcgtct acgaacgcaa tggcagcttt   180
tccagtcatg ccgtttggca gcaggtcgaa gaaggtcaag tgcaggagcg attgcttcag   240
cttgacggag ctccggctga agttctgctg gtaaatggtc agatgcaatg cgctaccgat   300
gacctcgcgg cgcaagtgcg tgaagcgcag gcttggcacg ggcagcgtct cgatccgaaa   360
gcactctccg agtggtacga attccgtgag atcggggatt cacgagttgc tggccgcccc   420
gccgtggcgc tggctgtcgt gccgaaggat cagcaccgtt acggcttcga actgcatctc   480
gaccaagata ccgcattgcc cctcaagtcg ctgatgctga acgagaaagg gcagctgctc   540 gagcgttttcc aattcaccca gttcacggct ggcagtgtat ctgccgagca actgaagccc   600
ggcgccgatt gcaatccagt gaccgtgaac cggcgcgagg cgaatcctac atcgccctgg   660
cgctccgact ggttgccttc cggcttcacg ctactggatg ccaacgaacg acctagtccc   720
gcctcttccg aaactgtttc ctggttgtcc tacggtgatg gtctagcgaa gttttccgtg   780
```

```
tttctggagc cgctgcgcgg cgccttggtt gaggacgcgc gaagccagat ggggcctacc    840
gtcgcggtct ctaagcgcat cagtactgcg gatggcgatg tcatggtgac cgtggtgggc    900
gagattccac ttggtacggc tgagcgggtt gccctgtcca tgcgagccag ttcggaacag    960
gcacaacgat gatcga                                                    976

<210> SEQ ID NO 82
<211> LENGTH: 1078
<212> TYPE: DNA
<213> ORGANISM: Pseudomonas alcaliphila

<400> SEQUENCE: 82
caggtacctc aggccgcgtt gctttatgcc tcttctcatg gcttgggaag cgccatgctg     60
gctgcaggga tctggctgct gctgccgcgc cgctatcgct acccccttgcc ctggagcccg    120 ctgttcattt tcagcgtctc gttcttcatt cccttgattg ggatgatcgg cgtagcgctg    180
gcgctgtttc cggccctcta cttgccgcgc aagcgcaagg tgcagtcctg ggaggctact    240
gccgttcccg agctgccttt ccggccgcgc gagcgcaagc gtgagctgat gttcagcgat    300
ggcgggctgc aggatgtgtt acgccatgcg cgcgaccccg atcagcgtct gacgccatc     360 ttcgcgacac gacgcatgcg cagcaaggag gccatcccga ttctcaagct ggcgctgcgc    420
gatccatctg acgatgttcg cctgctggcc tattcgatgc tcgatcagcg tgaaagccga    480
atcaaccagc gtatcgagcg tgcgctggca gatatggaga cgccagcac ggaccgtaag     540 ttcgccctgc atgggcaact ggcgcgctgg tactgggagc tcgcctatgt cggcctggcc    600
cagggcagtg tgttggagca cgtgctgcag caggcctgga gccatgtgat ggcggcgctg    660
cagggtggct cgggtggcga actgcacttg cttgccgggc gcatcgccat ggagcagggc    720
aatctcgatg aggcgttggc gcagttcgac cagtcggcgc tggccgggat ggatgcggtg    780
caattggcgc cgtatcgggc tgaaatcgcg ttttttgcgtc aacgctatga ggaaattcca    840
gaaatgctgg cgacgatgcc ggccgaactg ttgcaacgtc ccccttcgc ggccttggct     900 agatattggt tatgagtgag aaatctgctg ttcctgacgt gcagagcgtc gatgtctgcc    960
tgttgctcga gggaacctgg ccgtacgtgc gcgggggggt atcgagctgg atcaaccaac   1020
tgatcctggg gctgccggaa ctgaccttct cggtgctgtt catcggcggt cagaagga    1078

<210> SEQ ID NO 83
<211> LENGTH: 1305
<212> TYPE: DNA
<213> ORGANISM: Pseudomonas alcaliphila

<400> SEQUENCE: 83
gcctacctgt atgccggcct gatcagttcc ggcccttggg tattgtcgat catcagcgtg     60
atgctcatcg gcgtactgag cctgggggcg gtgctgccgg aaacgctgat cggtcagttc    120
ctggtcaccg tgacgtacct gatggccacg tcgctgattc tcaccggcgg actgcagctg    180
ttcttcaccc gcttcgtctc cgaccggctg ttcgagcggc gcctggacct gatcctgccc    240
aatctgatcg ggatactgct gctggtgacg atcttctcgg gctgctggcc ggtctgtgtg    300
atgggcctgc tgttcgatca gtcgtttacc tatcgcctgc tggtgatggc caacttcgtg    360
gtgctgtgca acctctggct ggtgatcatc ttcctgtcgg ggatgaaggc ttataaccgc    420
atcctgggcg tgatgtttct cggctactcg ctgatggtcg cctcggccta tctgctgcgc    480
tttctgaata tcgacggctt gctgctgggc ctgctgatcg gtcattccag cctgctgttc    540
```

| | |
|---|---|
| atcttcctgt tcgacatcct gcgcgagtac ccggccgagc gcctggtcgc gttcgatttt | 600 |
| ctcaagcgtc gccaggtgtt cggcagcctg ctgctgacag gactttgcta caacctgggc | 660 |
| atctggatcg acaagttcat cttctggttc aacccctcga cttccgaagc cgtgatcggc | 720 |
| ccgttgcggg cctcgatcct ctatgacctg ccgatcttcc ttgcctacct gtcgatcatc | 780 |
| cccggcatgg cggtgttcct ggtgcgtatc gaaacggact tcgccgaatg gtacgagcgg | 840 |
| gtctatgacg cgatccgcgg cggtgaaacc ctgcagcaca tcggctggct caaggagcag | 900 |
| atgatcctgg cgattcgcca gggcctgatg gagatctgca aggttcaggg gctgaccctg | 960 |
| gttctgctat tcctgctcgc gccgcagttg ttgtcctggc tgggcatctc gcactactac | 1020 |
| ctgccgctgt tctacatcga cgtgataggc gtgagcattc aggtggtgtt catggccttg | 1080 |
| ctcaacgtgt tcttctatct ggacaagcgt gccatcgtcc tcgaactctg cgttctcttc | 1140 |
| gtcctggcaa acggcgcgtt gaccctgttc agccagatgc ttggcccgac cttcttcggc | 1200 |
| tatggcttca ccctgtcgct gctgctgtgc gtactcctcg ggttgtatcg tctcaacgag | 1260 |
| gcgcttgatg atctcgagtt cgaaaccttc atgctcaatc gctga | 1305 |

<210> SEQ ID NO 84
<211> LENGTH: 1390
<212> TYPE: DNA
<213> ORGANISM: Pseudomonas toyotomiensis
<220> FEATURE:
<221> NAME/KEY: modified_base
<222> LOCATION: (237)..(237)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (525)..(525)
<223> OTHER INFORMATION: a, c, t, g, unknown or other

<400> SEQUENCE: 84

| | |
|---|---|
| atgatcagca agtggctgtt tagcggcgct gcgctgctcg aggtcgggag ctgggccagt | 60 |
| gcggtcagcg atctcccgat tcatcaggcc gcgttgctct atgcctccgc gcatggcctg | 120 |
| ggcagtgcga tgctggctgc cgggatctgg ctgctgctgc cgcgccgcta tcgctacccc | 180 |
| ttgccttgga gcctgctgtt cattttcagc atctcgttct tcatcccct gatcggnatg | 240 |
| atcggcgtgg cgctggcgtt gtttcccgcc ctctacttgc cgcgaaaggg caaggtgcag | 300 |
| tcttgggagg cgaccgccgt tcccgaactg cctttccgac cgcgtgagcg caagcaggag | 360 |
| ttgatgttca gcgatggtgg ccttcaggac gtgttgcgtc atgcgcgtga ccccgatcag | 420 |
| cgcctgacgg cgatcttcgc cacacgacgc atgcgcagca aggaggccat cccgattctc | 480 |
| aagctggcgc tgcgcgatcc atcngacgac gtgcgtttgc tggcntactc gatgctcgat | 540 |
| cagcgtgaaa gccgaatcaa ccagcgtatc gagcgcgctc tggcagatat ggagagcgcc | 600 |
| agcacggacc gccagttcgc cctgcatggg caactggcgc gttggtactg ggagcttgcc | 660 |
| tatgtcggcc tggcccaggg cagtgttctg gagcacgtgc tgcagcaggc ctggagccat | 720 |
| gtgatgcgg cgctgcaggg caactcgggt ggtgagctgc acttgttggc cgggcgtatc | 780 |
| gccatggagc agggcaatct cgacgaggcg ttggcgcagt tcgaccagtc ggcacaggcc | 840 |
| gggatggatg cggtgcagtt ggcgccgtat cgggccgaga tcgcgttttt gcgtcaacgc | 900 |
| tatgaggaaa ttccagacat gttggcgacg atgccggccg agctgttgca acgtcccccc | 960 |
| ttcgcggctt tggcaagata ctggttatga gtgagaaatc cgctgttcct gacgtacaga | 1020 |

| | |
|---|---|
| gcgtcgatgt ctgtctgttg ctagagggga cctggcccta tgtgcgtggg ggcgtgtcta | 1080 |
| gctggatcaa ccagctgatc ctggggctgc ctgagctgac tttctcggtg ctgttcatcg | 1140 |
| gcggtcagaa ggaggcctac ggcaagcgcc attacgctat cccggacaac gtggtgcaca | 1200 |
| ttcaggagca tttcctcgaa gactcctgga gttcgattcc caccaccagt acccgtcgca | 1260 |
| gcgctgagct ggccgagctg atgctggatg tgcaccgttt cctgcacaac ccggaggaac | 1320 |
| ccagcactga gcagggcgat gcattcgtcg ataccctggc tgccggacgc atcggccgtg | 1380 |
| aggccttcct | 1390 |

<210> SEQ ID NO 85
<211> LENGTH: 827
<212> TYPE: DNA
<213> ORGANISM: Pseudomonas toyotomiensis

<400> SEQUENCE: 85

| | |
|---|---|
| tcagctacat ccgtagattg tggatccgct tcttcgagcg tattgggctg atcacctacc | 60 |
| gatctgcgca ctccatcatc gcgctgtacg agggcaacag gcggcgtcag gttctcgatg | 120 |
| gcgctcctga ggagcgtact agggtcattc ccaatggcat cgatctggcc agttgggatc | 180 |
| aggcgctgct cagccggcca gaaggcgtgc cgccggtggc cggcctggtt gggcgggtgg | 240 |
| taccgatcaa ggacgtcaaa accttcatcc gcgccatccg tggtgtggtc agcgtcatac | 300 |
| ccgaagccga gggctggatc gtcgggccgg aagaagaaga tccggattac gcggccgagt | 360 |
| gccacagcct ggtggccagc ctggggctgc aggacaaggt gcgttttctc ggcttccgcc | 420 |
| aggtgcgcga agtcgtaccg caactgggcg tgatggtgct gacgtcgatc agtgaggcgc | 480 |
| agccgctggt ggtacttgag gcctggggcg ccggcacgcc agtggtgacc agtgacgtcg | 540 |
| gctcgtgtcg cgagctggtc gaaggctcca cgcaggagga tcgccagctc ggtacggcgg | 600 |
| gggaggtggt agcaattgcc gacccgcagg ccacctcgcg cgccattctc tcgctgttgc | 660 |
| gcaacccgga gcgctggaag gctgcgcagg ctgtcggcct tgagcgtgtg cggcgttact | 720 |
| acaccgaaga actgatgctc gcgcgctatc gcgagttgta tcgcgaaggc acggagagcg | 780 |
| cgtaatggcg ggtataggct ttgaactgag gaagatcctg tccaagg | 827 |

<210> SEQ ID NO 86
<211> LENGTH: 1260
<212> TYPE: DNA
<213> ORGANISM: Pseudomonas toyotomiensis

<400> SEQUENCE: 86

| | |
|---|---|
| gatgcgcgcc tacctgtatg ccggcctgat cagttccggc ccttgggtgt tgtcgatcat | 60 |
| cagcgtgatg ctcatcggtg tactgagcct ggggcggtg ctgccggaaa cgctgatcgg | 120 |
| ccagttcctg gtcaccgtga cctacctgat ggccacgtcg ctgattctca ccggcgggct | 180 |
| gcagctgttc ttcacccgct tcgtctccga ccggttgttc gagaaacgcc tggacctgat | 240 |
| cctgcccaac ctggtgggca tactgctgct ggtaacgatc gtctcggggc tgctggcaat | 300 |
| ctgcgtgttg ggcttgctgt tcgatcagtc gttttcctat cgcctgctgg tgatggccaa | 360 |
| cttcgtggtc ctgtgcaacc tgtggctggt gatcatcttc ctgtcgggga tgaaggccta | 420 |
| caaccgcatt tcggcgtga tgttcctcgg ctactcgctg atggtcgcct cggcctatct | 480 |
| gctgcgcttt ctcaatatcg acggcctgct gctgggcctg ctgatcggtc actccagcct | 540 |
| gctgttcatc ttcctcttcg acatccttcg cgagtacccg gccgagcgcc tggtcgcgtt | 600 |

| | |
|---|---|
| cgatttcctc aagcgccgtc aggtattcgg cagcctgctg ctgacagggc tgtgctacaa | 660 |
| cctgggtatc tggatcgaca agttcatctt ctggttcaac ccctcgactt ccgaagccgt | 720 |
| gatcggccca ttgcgcgcat cgatcctcta tgacctgccg atcttcctcg cctatctgtc | 780 |
| gatcatcccc ggcatggcgg tgtttctggt acgtatcgaa accgacttcg ccgagtggta | 840 |
| cgagcgggtc tatgacgcga tccgcggcgg ggaaaccctg cagcacatcg gctggctcaa | 900 |
| ggagcagatg atcctggcga ttcgccaggg tctgatggaa atctgcaagg tccaggggct | 960 |
| gaccctggtt ctgctgtttc tgctggcgcc gcagttgttg tcctggctcg gcatctcgca | 1020 |
| ctactacctg ccgctgttct atatcgacgt gatcggcgtg agcattcagg tggtattcat | 1080 |
| ggccttgctc aacgtgttct tctatctgga caagcgcgcc atcgtcctcg aactctgcgt | 1140 |
| tctcttcgtc ctggcaaacg gtgcgctgac cctgttcagc cagatgcttg cccgacatt | 1200 |
| cttcggctat ggcttcaccc tgtcgctgct gctgtgcgtg ctcctggggt tgtatcgtct | 1260 |

<210> SEQ ID NO 87
<211> LENGTH: 1170
<212> TYPE: DNA
<213> ORGANISM: Halomonas campisalis

<400> SEQUENCE: 87

| | |
|---|---|
| ggggataacc tggggaaacc caggctaata ccgcatacgt cctacgggag aaagcagggg | 60 |
| atcttcggac cttgcgctat cggatgagcc catgtcggat tagcttgttg gtgaggtaat | 120 |
| ggctcaccaa ggcgacgatc cgtagctggt ctgagaggat gatcagccac atcgggactg | 180 |
| agacacggcc cgaactccta cgggaggcag cagtggggaa tattggacaa tgggcgaaag | 240 |
| cctgatccag ccatgccgcg tgtgtgaaga aggccctcgg gttgtaaagc actttcagtg | 300 |
| gggaagaaag ccttgaggtt aataccttcg aggaaggaca tcacccacag aagaagcacc | 360 |
| ggctaactcc gtgccagcag ccgcggtaat acggagggtg cgagcgttaa tcggaattac | 420 |
| tgggcgtaaa gcgcgcgtag gcggtctgat aagccggttg tgaaagcccc gggctcaacc | 480 |
| tgggaacggc atccggaact gtcaggctag agtgcaggag aggaaggtag aattcccggt | 540 |
| gtagcggtga atgcgtaga gatcgggagg aataccagtg gcgaaggcgg ccttctggac | 600 |
| tgacactgac gctgaggtgc gaaagcgtgg gtagcaaaca ggattagata ccctggtagt | 660 |
| ccacgccgta aacgatgtcg actagccgtt ggggtccttg agacctttgt ggcgcagtta | 720 |
| acgcgataag tcgaccgcct ggggagtacg gccgcaaggt taaaactcaa atgaattgac | 780 |
| gggggcccgc acaagcggtg gagcatgtgg tttaattcga tgcaacgcga agaaccttac | 840 |
| ctacccttga catcgagaga acttggcaga gatgccttgg tgccttcggg aactctcaga | 900 |
| caggtgctgc atggctgtcg tcagctcgtg ttgtgaaatg ttgggttaag tcccgtaacg | 960 |
| agcgcaaccc ttgtccttat ttgccagcgc gtaatggcgg gaactctaag gagactgccg | 1020 |
| gtgacaaacc ggaggaaggt ggggacgacg tcaagtcatc atggccctta cgggtagggc | 1080 |
| tacacacgtg ctacaatgga cggtacaaag ggttgcaaag ccgcgaggtg gagctaatcc | 1140 |
| cataaagctg ttctcagtcc ggatcggagt | 1170 |

<210> SEQ ID NO 88
<211> LENGTH: 783
<212> TYPE: DNA
<213> ORGANISM: Caldalkalibacillus uzonensis
<220> FEATURE:
<221> NAME/KEY: modified_base
<222> LOCATION: (543)..(543)
<223> OTHER INFORMATION: a, c, t, g, unknown or other

<400> SEQUENCE: 88

```
agcctgatgg agcacgccgc gtgagcgagg aaggtcttcg gattgtaaag ctctgttgtt      60
agggaagaac aagtgtcgtt cgaatagggc ggcaccttga cggtacctaa cgagaaagcc     120
ccggctaact acgtgccagc agccgcggta atacgtaggg ggtcgagcgt tgtccggaat     180
tattgggcgt aaagcgcgcg caggcggtct cttaagtctg atgtgaaagc ccacggctca     240
accgtggagg gtcattggaa actgggagac ttgagtgcag gagagggaag cggaattcca     300
cgtgtagcgg tgaaatgcgt agagatgtgg aggaacacca gtggcgaagg cggcttcctg     360
gcctgtaact gacgctgagg cgcgaaagcg tggggagcga acaggattag ataccctggt     420
agtccacgcc gtaaacgatg agtgctaggt gttgggggtt caacaccct cagtgctgaa      480
gttaacacat taagcactcc gcctggggag tacggccgca aggctgaaac tcaaaggaat     540
tgncggggc ccgcacaagc ggtggagcat gtggtttaat tcgaagcaac gcgaagaacc      600
ttaccaggac ttgacatcct ctgaccgccc tagagatagg gtcttcccct tcggggggaca    660
gagtgacagg tggtgcatgg ttgtcgtcag ctcgtgtcgt gagatgttgg gttaagtccc     720
gcaacgagcg caaccttga ccttagttgc cagcattcag ttgggcactc taaggtgact      780
gcc                                                                   783
```

```
<210> SEQ ID NO 89
<211> LENGTH: 1168
<212> TYPE: DNA
<213> ORGANISM: Unknown
<220> FEATURE:
<223> OTHER INFORMATION: Description of Unknown:
      16S rDNA sequence
<220> FEATURE:
<221> NAME/KEY: modified_base
<222> LOCATION: (69)..(69)
<223> OTHER INFORMATION: a, c, t, g, unknown or other
<220> FEATURE:
<221> NAME/KEY: modified_base
<222> LOCATION: (77)..(78)
<223> OTHER INFORMATION: a, c, t, g, unknown or other
<220> FEATURE:
<221> NAME/KEY: modified_base
<222> LOCATION: (1110)..(1110)
<223> OTHER INFORMATION: a, c, t, g, unknown or other
<220> FEATURE:
<221> NAME/KEY: modified_base
<222> LOCATION: (1114)..(1114)
<223> OTHER INFORMATION: a, c, t, g, unknown or other
<220> FEATURE:
<221> NAME/KEY: modified_base
<222> LOCATION: (1118)..(1118)
<223> OTHER INFORMATION: a, c, t, g, unknown or other
<220> FEATURE:
<221> NAME/KEY: modified_base
<222> LOCATION: (1126)..(1126)
<223> OTHER INFORMATION: a, c, t, g, unknown or other
<220> FEATURE:
<221> NAME/KEY: modified_base
<222> LOCATION: (1128)..(1128)
<223> OTHER INFORMATION: a, c, t, g, unknown or other
<220> FEATURE:
<221> NAME/KEY: modified_base
<222> LOCATION: (1130)..(1130)
<223> OTHER INFORMATION: a, c, t, g, unknown or other
<220> FEATURE:
<221> NAME/KEY: modified_base
<222> LOCATION: (1146)..(1146)
<223> OTHER INFORMATION: a, c, t, g, unknown or other
<220> FEATURE:
<221> NAME/KEY: modified_base
<222> LOCATION: (1150)..(1150)
<223> OTHER INFORMATION: a, c, t, g, unknown or other
```

<220> FEATURE:
<221> NAME/KEY: modified_base
<222> LOCATION: (1160)..(1160)
<223> OTHER INFORMATION: a, c, t, g, unknown or other

<400> SEQUENCE: 89

| | | | | | |
|---|---|---|---|---|---|
| tatacaagga | aaggccgctg | aaaagcgacc | tcttttttca | tcaatcaatg | tccagaggcc | 60 |
| ttgtacacnc | cgccccnngg | tttcggctat | cacttacaga | tgggcccgcg | gcgcattagc | 120 |
| tagttggtga | ggtaacggct | caccaaggca | acgatgcgta | gccgacctga | gagggtgatc | 180 |
| ggccacactg | ggactgagac | acggcccaga | ctcctacggg | aggcagcagt | agggaatctt | 240 |
| ccgcaatgga | cgaaagtctg | acggagcaac | gccgcgtgag | tgatgaaggt | tttcggatcg | 300 |
| taaaactctg | ttgttaggga | agaacaagtg | ccgttcgaaa | gggcggcacc | ttgacggtac | 360 |
| ctaacgagaa | agccacggct | aactacgtgc | cagcagccgc | ggtaatacgt | aggtggcaag | 420 |
| cgttgtccgg | aattattggg | cgtaaagcgc | gcgcaggcgg | tctcttaagt | ctgatgtgaa | 480 |
| agcccccggc | tcaaccgggg | agggtcattg | gaaactggga | gacttgagta | cagaagagga | 540 |
| gagtggaatt | ccacgtgtag | cggtgaaatg | cgtagagatg | tggaggaaca | ccagtggcga | 600 |
| aggcgactct | ctggtctgta | actgacgctg | aggcgcgaaa | gcgtggggag | caaacaggat | 660 |
| tagataccct | ggtagtccac | gccgtaaacg | atgagtgcta | ggtgttaggg | gtttcgacgc | 720 |
| ccttagtgcc | gaagttaaca | cattaagcac | tccgcctggg | gagtacgacc | gcaaggttga | 780 |
| aactcaaagg | aattgacggg | ggcccgcaca | agcagtggag | catgtggttt | aattcgaagc | 840 |
| aacgcgaaga | accttaccag | gtcttgacat | cctttgacca | ccctagagat | agggctttcc | 900 |
| ccttcggggg | acaaagtgac | aggtggtgca | tggttgtcgt | cagctcgtgt | cgtgagatgt | 960 |
| tgggttaagt | cccgcaacga | gcgcaaccct | tgaccttagt | tgccagcatt | cagttgggca | 1020 |
| ctctaaggtg | actgccggtg | acaaaccgga | ggaaggtggg | gatgacgtca | aatcatcatg | 1080 |
| ccccttatga | cctgggctac | acacgtgctn | ctcnggcnta | acacangnan | tcgaagccgc | 1140 |
| gaaggngcan | ccgatacctn | aaagccct | | | | 1168 |

<210> SEQ ID NO 90
<211> LENGTH: 1395
<212> TYPE: DNA
<213> ORGANISM: Idiomarina sp.

<400> SEQUENCE: 90

| | | | | | |
|---|---|---|---|---|---|
| gagggttaag | ctatctactt | ctggtgcagc | ccactcccat | ggtgtgacgg | gcggtgtgta | 60 |
| caaggcccgg | gaacgtattc | accgtggcat | tctgatccac | gattactagc | gattccgact | 120 |
| tcacggagtc | gagttgcaga | ctccgatccg | gactacgacg | cgctttttga | gattcgcttg | 180 |
| ctatcgctag | cttgctgccc | tttgtgcgcg | ccattgtagc | acgtgtgtag | cccatcccgt | 240 |
| aagggccatg | atgacttgac | gtcgtcccca | ccttcctccg | gtttatcacc | ggcagtctcc | 300 |
| ctagagttcc | caccattacg | tgctggcaac | taaggataag | ggttgcgctc | gttgcgggac | 360 |
| ttaacccaac | atctcacaac | acgagctgac | gacagccatg | cagcacctgt | ctcagagttc | 420 |
| ccgaaggcac | taatccatct | ctggaaaatt | ctctggatgt | caagggatgg | taaggttctt | 480 |
| cgcgttgcat | cgaattaaac | cacatgctcc | accgcttgtg | cgggccccg | tcaattcatt | 540 |
| tgagttttaa | ccttgcggcc | gtactcccca | ggcggtcaac | ttagtgcgtt | agctgcgtta | 600 |
| ctcacatcat | aatgacacga | acaactagtt | gacatcgttt | acggcgtgga | ctaccagggt | 660 |
| atctaatcct | gtttgctccc | cacgctttcg | ctcctcagcg | tcagtttttg | accaggtggc | 720 |

```
cgccttcgcc actggtattc cttccaatat ctacgcattt caccgctaca ctggaaattc    780
taccaccctc ttcaaaactc tagcctgcca gttcaaaatg ctattccaag gttgagccct    840
gggctttcac atcttgctta acaggccgcc tacgtgcgct ttacgcccag taattccgat    900
taacgctcgc accctccgta ttaccgcggc tgctggcacg gagttagccg gtgcttcttc    960
tgtggctaac gtcaatcgtt gccgctatta acgacaacgc cttcctcacc actgaaagtg   1020
ctttacaacc cgaaggcctt cttcacacac gcggcatggc tggatcaggc ttgcgcccat   1080
tgtccaatat tccccactgc tgcctcccgt aggagtctgg gccgtgtctc agtcccagtg   1140
tggctgatca tcctctcaga ccagctagag atcgtcgcct tggtgagcca ttacctcacc   1200
aactagctaa tctcgcttgg gttcatctga tggcgtatgg cccgaaggtc ccatactttg   1260
ctccgaagag attatgcggt attagccacc gtttccagtg gttgtccccc gccatcaggc   1320
agatccccaa gtattactca cccgtccgcc gctcgtcatc atctagcaag ctagatatgt   1380
taccgctcga ctgca                                                    1395
```